（12) United States Patent
Rahl et al.

(10) Patent No.: US 9,155,724 B2
(45) Date of Patent: Oct. 13, 2015

(54) COMBINATION METHODS FOR TREATMENT OF DISEASE

(75) Inventors: Peter B. Rahl, Natick, MA (US); Richard A. Young, Weston, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 514 days.

(21) Appl. No.: 13/577,098

(22) PCT Filed: Feb. 4, 2011

(86) PCT No.: PCT/US2011/023804
§ 371 (c)(1),
(2), (4) Date: Nov. 15, 2012

(87) PCT Pub. No.: WO2011/097522
PCT Pub. Date: Aug. 11, 2011

(65) Prior Publication Data
US 2013/0053415 A1    Feb. 28, 2013

Related U.S. Application Data

(60) Provisional application No. 61/302,061, filed on Feb. 5, 2010, provisional application No. 61/301,978, filed on Feb. 5, 2010.

(51) Int. Cl.
| A61K 31/435 | (2006.01) |
| A61K 31/426 | (2006.01) |
| C12Q 1/18 | (2006.01) |
| C12N 5/071 | (2010.01) |
| A61K 31/4025 | (2006.01) |
| A61K 31/445 | (2006.01) |
| A61K 31/453 | (2006.01) |
| A61K 45/06 | (2006.01) |
| G01N 33/50 | (2006.01) |

(52) U.S. Cl.
CPC ........... *A61K 31/4025* (2013.01); *A61K 31/426* (2013.01); *A61K 31/445* (2013.01); *A61K 31/453* (2013.01); *A61K 45/06* (2013.01); *G01N 33/5011* (2013.01); *G01N 2333/4704* (2013.01)

(58) Field of Classification Search
CPC ... A61K 31/4433; A61K 31/426; C12Q 1/18; C12N 5/071; C12N 5/09
USPC ...................... 514/320, 369; 435/32, 366, 375
See application file for complete search history.

(56) References Cited

U.S. PATENT DOCUMENTS

| 2004/0034060 A1 | 2/2004 | Prochownik et al. |
| 2004/0152651 A1 | 8/2004 | Rana |
| 2005/0277680 A1 | 12/2005 | Priebe et al. |
| 2007/0238745 A1 | 10/2007 | Mohapatra et al. |

FOREIGN PATENT DOCUMENTS

| WO | WO 97/42949 A1 | 11/1997 |
| WO | WO 2006/101846 A1 | 9/2006 |
| WO | WO 2007/098010 A2 | 8/2007 |
| WO | WO 2007/148158 A1 | 12/2007 |
| WO | WO 2009/047359 A1 | 4/2009 |
| WO | WO 2010/003133 A2 | 1/2010 |

OTHER PUBLICATIONS

Extended European Search Report, mailed May 28, 2013 for EP 11740458.2.
International Search Report and Written Opinion for PCT/US2011/023804, mailed Oct. 13, 2011.
International Preliminary Report on Patentability for PCT/US2011/023804, mailed Aug. 16, 2012.
Adelman et al., Drosophila Paf1 modulates chromatin structure at actively transcribed genes. Mol Cell Biol. Jan. 2006;26(1):250-60.
Ahn et al., Phosphorylation of serine 2 within the RNA polymerase II C-terminal domain couples transcription and 3' end processing. Mol Cell. Jan. 16, 2004;13(1):67-76.
Ali et al., Identification of flavopiridol analogues that selectively inhibit positive transcription elongation factor (P-TEFb) and block HIV-1 replication. Chembiochem. Aug. 17, 2009;10(12):2072-80.
Andrulis et al., High-resolution localization of Drosophila SptS and Spt6 at heat shock genes in vivo: roles in promoter proximal pausing and transcription elongation. Genes Dev. Oct. 15, 2000;14(20):2635-49.
Arabi et al., c-Myc associates with ribosomal DNA and activates RNA polymerase I transcription. Nat Cell Biol. 2005;7:303-10.
Balkwill et al., Inflammation and cancer: back to Virchow? Lancet. Feb. 17, 2001;357(9255):539-45.
Barboric et al., 7SK snRNP/P-TEFb couples transcription elongation with alternative splicing and is essential for vertebrate development. Proc Natl Acad Sci U S A. May 12, 2009;106(19):7798-803. Epub Apr. 27, 2009.
Barboric et al., A new paradigm in eukaryotic biology: HIV Tat and the control of transcriptional elongation. PLoS Biol. Feb. 2005;3(2):e76.
Barboric et al., NF-kappaB binds P-TEFb to stimulate transcriptional elongation by RNA polymerase II. Mol Cell. Aug. 2001;8(2):327-37.
Barski et al., High-resolution profiling of histone methylations in the human genome. Cell. May 18, 2007;129(4):823-37.
Baugh et al., RNA Pol II accumulates at promoters of growth genes during developmental arrest. Science. Apr. 3, 2009;324(5923):92-4. Epub Feb. 26, 2009.
Baumli et al., The structure of P-TEFb (CDK9/cyclin T1), its complex with flavopiridol and regulation by phosphorylation. EMBO J. Jul. 9, 2008;27(13):1907-18. Epub Jun. 19, 2008.
Benson et al., A phase I trial of the selective oral cyclin-dependent kinase inhibitor seliciclib (CYC202; R-Roscovitine), administered twice daily for 7 days every 21 days. Br J Cancer. Jan. 15, 2007;96(1):29-37.

(Continued)

*Primary Examiner* — Raymond Henley, III
(74) *Attorney, Agent, or Firm* — Wolf, Greenfield & Sacks, P.C.

(57) ABSTRACT

In some aspects, the invention provides compositions and methods of use for treating a variety of diseases. In some aspect, the compositions and methods involve combined modulation of transcriptional modulators.

33 Claims, 20 Drawing Sheets

(56) References Cited

OTHER PUBLICATIONS

Bentley et al., A block to elongation is largely responsible for decreased transcription of c-myc in differentiated HL60 cells. Nature. Jun. 12-18, 1986;321(6071):702-6.

Berg et al., Small-molecule antagonists of Myc/Max dimerization inhibit Myc-induced transformation of chicken embryo fibroblasts. Proc Natl Acad Sci USA. 2002;99:3830-5.

Berg, Inhibition of transcription factors with small organic molecules. Curr Opin Chem Biol. Aug. 2008;12(4):464-71. Epub Aug. 13, 2008.

Bilodeau et al., SetDB1 contributes to repression of genes encoding developmental regulators and maintenance of ES cell state. Genes Dev. Nov. 1, 2009; 23(21): 2484-2489.

Boettiger et al., Synchronous and stochastic patterns of gene activation in the Drosophila embryo. Science. Jul. 24, 2009;325(5939):471-3.

Boyer et al., Core Transcriptional Regulatory Circuitry in Human Embryonic Stem Cells. Cell. Sep. 23, 2005; 122(6): 947-956.

Byrd et al., Flavopiridol administered using a pharmacologically derived schedule is associated with marked clinical efficacy in refractory, genetically high-risk chronic lymphocytic leukemia. Blood. Jan. 15, 2007; 109(2): 399-404.

Cartwright et al., LIF/STAT3 controls ES cell self-renewal and pluripotency by a Myc-dependent mechanism. Development. Mar. 2005;132(5):885-96. Epub Jan. 26, 2005.

Chao et al., Flavopiridol inactivates P-TEFb and blocks most RNA polymerase II transcription in vivo. J Biol Chem. Aug. 24, 2001;276(34):31793-9. Epub Jun. 28, 2001.

Chao et al., Flavopiridol inhibits P-TEFb and blocks HIV-1 replication. J Biol Chem. Sep. 15, 2000;275(37):28345-8.

Chen et al., Integration of external signaling pathways with the core transcriptional network in embryonic stem cells. Cell. Jun. 13, 2008;133(6):1106-17.

Cheng et al., Properties of RNA polymerase II elongation complexes before and after the P-TEFb-mediated transition into productive elongation. J Biol Chem. Jul. 27, 2007;282(30):21901-12. Epub Jun. 4, 2007.

Cho et al., Modulation of the Brd4/P-TEFb interaction by the human T-lymphotropic virus type 1 tax protein. J Virol. Oct. 2007;81(20):11179-86. Epub Aug. 8, 2007.

Chopra et al., Regulation of Hox gene activity by transcriptional elongation in Drosophila. Curr Biol. Apr. 28, 2009;19(8):688-93. doi: 10.1016/j.cub.2009.02.055. Epub Apr. 2, 2009.

Christian et al., Flavopiridol in the treatment of chronic lymphocytic leukemia. Curr Opin Oncol. Nov. 2007;19(6):573-8.

Core et al., Nascent RNA sequencing reveals widespread pausing and divergent initiation at human promoters. Science. Dec. 19, 2008;322(5909):1845-8. Epub Dec. 4, 2008.

Core et al., Transcription regulation through promoter-proximal pausing of RNA polymerase II. Science. Mar. 28, 2008;319(5871):1791-2.

Eberhardy et al., c-Myc mediates activation of the cad promoter via a post-RNA polymerase II recruitment mechanism. J Biol Chem. Dec. 21, 2001;276(51):48562-71. Epub Oct. 22, 2001.

Eberhardy et al., Myc recruits P-TEFb to mediate the final step in the transcriptional activation of the cad promoter. J Biol Chem. Oct. 18, 2002;277(42):40156-62. Epub Aug. 9, 2002.

Eilers et al., Myc's broad reach. Genes Dev. Oct. 15, 2008;22(20):2755-66.

Espinosa et al., p53 functions through stress- and promoter-specific recruitment of transcription initiation components before and after DNA damage. Mol Cell. Oct. 2003;12(4):1015-27.

Fang et al., Transcriptional regulation of survivin by c-Myc in BCR/ABL-transformed cells: implications in anti-leukaemic strategy. J Cell Mol Med. Aug. 2009;13(8B):2039-52.

Faumont et al., c-Myc and Rel/NF-κB are the Two Master Transcriptional Systems Activated in the Latency III Program of Epstein-Barr Virus-Immortalized B Cells. J Virol. May 2009; 83(10):5014-5027. Epub Mar. 2009.

Follis et al., Structural rationale for the coupled binding and unfolding of the c-Myc oncoprotein by small molecules. Chem Biol. 2008;15:1149-55.

Fuda et al., Defining mechanisms that regulate RNA polymerase II transcription in vivo. Nature. Sep. 10, 2009;461(7261):186-92.

Gargano et al., P-TEFb is a crucial co-factor for Myc transactivation. Cell Cycle. Aug. 15, 2007;6(16):2031-7. Epub Jun. 5, 2007.

Ghosh et al., Inhibition of transcription by the Caenorhabditis elegans germline protein PIE-1: genetic evidence for distinct mechanisms targeting initiation and elongation. Genetics. Jan. 2008;178(1):235-43.

Gilmore et al., Inhibitors of NF-kappaB signaling: 785 and counting. Oncogene. Oct. 30, 2006;25(51):6887-99.

Gilmour et al., RNA polymerase II interacts with the promoter region of the noninduced hsp70 gene in Drosophila melanogaster cells. Mol Cell Biol. Nov. 1986;6(11):3984-9.

Glover-Cutter et al., RNA polymerase II pauses and associates with pre-mRNA processing factors at both ends of genes. Nat Struct Mol Biol. Jan. 2008;15(1):71-8. Epub Dec. 23, 2007.

Guenther et al., A chromatin landmark and transcription initiation at most promoters in human cells. Cell. Jul. 13, 2007;130(1):77-88.

Guenther et al., Aberrant chromatin at genes encoding stem cell regulators in human mixed-lineage leukemia. Genes Dev. Dec. 15, 2008; 22(24): 3403-3408.

Hailesellasse Sene et al., Gene function in early mouse embryonic stem cell differentiation. BMC Genomics. 2007;8:85.

Hall et al., Oct4 and LIF/Stat3 additively induce Krüppel factors to sustain embryonic stem cell self-renewal. Cell Stem Cell. Dec. 4, 2009;5(6):597-609.

Hammoudeh et al., Multiple independent binding sites for small-molecule inhibitors on the oncoprotein c-Myc. J Am Chem Soc. Jun. 3, 2009;131(21):7390-401.

Hanyu-Nakamura et al., Drosophila Pgc protein inhibits P-TEFb recruitment to chromatin in primordial germ cells. Nature. Feb. 7, 2008;451(7179):730-3. Epub Jan. 16, 2008.

Hayden et al., Shared principles in NF-kappaB signaling. Cell. Feb. 8, 2008;132(3):344-62.

Hochheimer et al., Diversified transcription initiation complexes expand promoter selectivity and tissue-specific gene expression. Genes Dev. Jun. 1, 2003;17(11):1309-20.

Hoffmann et al., the IkappaB-NF-kappaB signaling module: temporal control and selective gene activation. Science. Nov. 8, 2002;298(5596):1241-5.

Hoffmann et al., Transcriptional regulation via the NF-kappaB signaling module. Oncogene. Oct. 30, 2006;25(51):6706-16.

Innocenti et al., Flavopiridol metabolism in cancer patients is associated with the occurrence of diarrhea.Clin Cancer Res. 2000;6(9):3400-5.

International Hapmap Consortium et al., A second generation human haplotype map of over 3.1 million SNPs. Nature. Oct. 18, 2007;449(7164):851-61.

Kadonaga, Regulation of RNA polymerase II transcription by sequence-specific DNA binding factors. Cell. Jan. 23, 2004;116(2):247-57.

Kanazawa et al., c-Myc recruits P-TEFb for transcription, cellular proliferation and apoptosis. Oncogene. Aug. 28, 2003;22(36):5707-11.

Khanna et al., MYC-dependent regulation and prognostic role of CIP2A in gastric cancer. J Natl Cancer Inst. 2008;101:793-805.

Kidder et al., Stat3 and c-Myc genome-wide promoter occupancy in embryonic stem cells. PLoS One. 2008;3(12):e3932. Epub Dec. 11, 2008.

Kiessling et al., Selective inhibition of c-Myc/Max dimerization and DNA binding by small molecules. Chem Biol. Jul. 2006;13(7):745-51.

Kiessling et al., Selective inhibition of c-Myc/Max dimerization by a pyrazolo[1,5-a]pyrimidine. ChemMedChem. May 2007;2(5):627-30.

Kim et al., A high-resolution map of active promoters in the human genome. Nature. Aug. 11, 2005;436(7052):876-80. Epub Jun. 29, 2005.

Kim et al., An extended transcriptional network for pluripotency of embryonic stem cells. Cell. Mar. 21, 2008;132(6):1049-61.

(56) References Cited

OTHER PUBLICATIONS

Kim et al., Positive transcription elongation factor B phosphorylates hSPT5 and RNA polymerase II carboxyl-terminal domain independently of cyclin-dependent kinase-activating kinase. J Biol Chem. Apr. 13, 2001;276(15):12317-23. Epub Jan. 5, 2001.
Kim et al., Transitions in RNA polymerase II elongation complexes at the 3' ends of genes. EMBO J. Jan. 28, 2004;23(2):354-64. Epub Jan. 22, 2004.
Komarnitsky et al., Different phosphorylated forms of RNA polymerase II and associated mRNA processing factors during transcription. Genes Dev. Oct. 1, 2000;14(19):2452-60.
Krogan et al., the Paf1 complex is required for histone H3 methylation by COMPASS and Dot1p: linking transcriptional elongation to histone methylation. Mol Cell. Mar. 2003;11(3):721-9.
Lee et al., Chromatin immunoprecipitation and microarray-based analysis of protein location. Nat Protoc. 2006; 1(2): 729-748.
Lee et al., Control of developmental regulators by Polycomb in human embyonic stem cells. Cell. 2006;125:301-13.
Lee et al., JAK pathway induction of c-Myc critical to IL-5 stimulation of cell proliferation and inhibition of apoptosis. J Cell Biochem. 2009;106:929-36.
Lis et al., P-TEFb kinase recruitment and function at heat shock loci. Genes Dev. Apr. 1, 2000;14(7):792-803.
Lu et al., Disruption of the MYC transcriptional function by a small-molecule antagonist of MYC/MAX dimerization.Oncol Rep. 2008;19:825-30.
Maherali et al., Directly reprogrammed fibroblasts show global epigenetic remodeling and widespread tissue contribution. Cell Stem Cell. Jun. 7, 2007;1(1):55-70.
Mandal et al., Functional interactions of RNA-capping enzyme with factors that positively and negatively regulate promoter escape by RNA polymerase II. Proc Natl Acad Sci U S A. May 18, 2004;101(20):7572-7. Epub May 10, 2004.
Margaritis et al., Poised RNA polymerase II gives pause for thought. Cell. May 16, 2008;133(4):581-4.
Marshall et al., Control of RNA polymerase II elongation potential by a novel carboxyl-terminal domain kinase. J Biol Chem. Oct. 25, 1996;271(43):27176-83.
Marshall et al., Purification of P-TEFb, a transcription factor required for the transition into productive elongation. J Biol Chem. May 26, 1995;270(21):12335-8.
Marson et al., Connecting microRNA genes to the core transcriptional regulatory circuitry of embryonic stem cells. Cell. Aug. 8, 2008;134(3):521-33.
Matoba et al., Dissecting Oct3/4-regulated gene networks in embryonic stem cells by expression profiling. PLoS One. Dec. 20, 2006;1:e26.
McCracken et al., 5'-Capping enzymes are targeted to pre-mRNA by binding to the phosphorylated carboxy-terminal domain of RNA polymerase II. Genes Dev. Dec. 15, 1997;11(24):3306-18.
McCracken et al., The C-terminal domain of RNA polymerase II couples mRNA processing to transcription. Nature. Jan. 23, 1997;385(6614):357-61.
Meyer et al., Reflecting on 25 years with MYC. Nat Rev Cancer. Dec. 2008;8(12):976-90.
Mikkelsen et al., Genome-wide maps of chromatin state in pluripotent and lineage-committed cells. Nature. Aug. 2, 2007;448(7153):553-60. Epub Jul. 1, 2007.
Miller et al., Identification of known drugs that act as inhibitors of NF-kappaB signaling and their mechanism of action. Biochem Pharmacol. May 1, 2010;79(9):1272-80. Epub Jan. 11, 2010.
Mo et al, Myc overexpression enhances apoptosis induced by small molecules.Cell Cycle. 2006;5:2191-4.
Mo et al., Identification of small molecules that induce apoptosis in a Myc-dependent manner and inhibit Myc-driven transformation. Proc Natl Acad Sci U S A. Apr. 18, 2006;103(16):6344-9. Epub Apr. 10, 2006.
Moore et al., Pre-mRNA processing reaches back to transcription and ahead to translation. Cell. Feb. 20, 2009;136(4):688-700.
Morillon et al., Dynamic lysine methylation on histone H3 defines the regulatory phase of gene transcription. Mol Cell. Jun. 10, 2005;18(6):723-34.
Murthi et al., Structure-activity relationship studies of flavopiridol analogues. Bioorg Med Chem Lett. May 15, 2000;10(10):1037-41.
Muse et al., RNA polymerase is poised for activation across the genome. Nat Genet. Dec. 2007;39(12):1507-11. Epub Nov. 11, 2007.
Nam, Naturally occurring NF-kappaB inhibitors. Mini Rev Med Chem. Aug. 2006;6(8):945-51.
Naugler et al., NF-kappaB and cancer-identifying targets and mechanisms. Curr Opin Genet Dev. Feb. 2008;18(1):19-26. Epub Apr. 24, 2008.
Neil et al., Widespread bidirectional promoters are the major source of cryptic transcripts in yeast. Nature. Feb. 19, 2009;457(7232):1038-42. Epub Jan. 25, 2009.
Ni et al., Coordination of transcription, RNA processing, and surveillance by P-TEFb kinase on heat shock genes. Mol Cell. Jan. 16, 2004;13(1):55-65.
Ni et al., P-TEFb is critical for the maturation of RNA polymerase II into productive elongation in vivo. Mol Cell Biol. Feb. 2008;28(3):1161-70. Epub Dec. 10, 2007.
Niwa et al., Quantitative expression of Oct-3/4 defines differentiation, dedifferentiation or self-renewal of ES cells. Nat Genet. Apr. 2000;24(4):372-6.
O'Brien et al., RNA polymerase II pauses at the 5' end of the transcriptionally induced *Drosophila* hsp70 gene. Mol Cell Biol. Oct. 1991;11(10):5285-90.
Peng et al., Identification of multiple cyclin subunits of humanP-TEFb. Genes Dev. Mar. 1, 1998; 12(5): 755-762.
Peterlin et al., Controlling the elongation phase of transcription with P-TEFb. Mol Cell. Aug. 4, 2006;23(3):297-305.
Pokholok et al., Exchange of RNA polymerase II initiation and elongation factors during gene expression in vivo. Mol Cell. Apr. 2002;9(4):799-809.
Pokholok et al., Genome-wide map of nucleosome acetylation and methylation in yeast. Cell. Aug. 26, 2005;122(4):517-27.
Pomerantz et al., The 8q24 cancer risk variant rs6983267 demonstrates long-range interaction with MYC in colorectal cancer. Nat Genet. Aug. 2009; 41(8): 882-884.
Price, Poised polymerases: on your mark . . .get set . . .go! Mol Cell. Apr. 11, 2008;30(1):7-10.
Rahl et al., c-Myc regulates transcriptional pause release. Cell. Apr. 30, 2010;141(3):432-45.
Reppas et al., The transition between transcriptional initiation and elongation in *E. coli* is highly variable and often rate limiting. Mol Cell. Dec. 8, 2006;24(5):747-57.
Roeder, Transcriptional regulation and the role of diverse coactivators in animal cells. FEBS Lett. Feb. 7, 2005;579(4):909-15.
Rougvie et al., The RNA polymerase II molecule at the 5' end of the uninduced hsp70 gene of *D. melanogaster* is transcriptionally engaged. Cell. Sep. 9, 1988;54(6):795-804.
Sampson et al., MicroRNA let-7a down-regulates MYC and reverts MYC-induced growth in Burkitt lymphoma cells. Cancer Res. 2007;67:9762-70.
Saunders et al., Breaking barriers to transcription elongation. Nat Rev Mol Cell Biol. Aug. 2006;7(8):557-67.
Sawado et al., The beta-globin locus control region (LCR) functions primarily by enhancing the transition from transcription initiation to elongation. Genes Dev. Apr. 15, 2003;17(8):1009-18. Epub Apr. 2, 2003.
Schones et al., Dynamic regulation of nucleosome positioning in the human genome. Cell. Mar. 7, 2008;132(5):887-98.
Schreiber et al., Coordinated binding of NF-kappaB family members in the response of human cells to lipopolysaccharide. Proc Natl Acad Sci U S A. Apr. 11, 2006;103(15):5899-904. Epub Apr. 4, 2006.
Schubeler et al., The histone modification pattern of active genes revealed through genome-wide chromatin analysis of a higher eukaryote. Genes Dev. Jun. 1, 2004;18(11):1263-71.
Seila et al., Divergent transcription from active promoters. Science. Dec. 19, 2008;322(5909):1849-51. Epub Dec. 4, 2008.
Seydoux et al., Transcriptionally repressed germ cells lack a subpopulation of phosphorylated RNA polymerase II in early

(56) References Cited

OTHER PUBLICATIONS embryos of *Caenorhabditis elegans* and *Drosophila melanogaster*. Development. Jun. 1997;124(11):2191-201.

Sharova et al., Database for mRNA half-life of 19 977 genes obtained by DNA microarray analysis of pluripotent and differentiating mouse embryonic stem cells. DNA Res. Feb. 2009;16(1):45-58. Epub Nov. 11, 2008.

Sims et al., Elongation by RNA polymerase II: the short and long of it. Genes Dev. Oct. 15, 2004;18(20):2437-68.

Soucek et al., Modelling Myc inhibition as a cancer therapy. Nature. Oct. 2, 2008;455(7213):679-83. Epub Aug. 17, 2008.

Srinivasan et al., Structure-activity relationship studies of chalcone leading to 3-hydroxy-4,3',4',5'-tetramethoxychalcone and its analogues as potent nuclear factor kappaB inhibitors and their anticancer activities. J Med Chem. Nov. 26, 2009;52(22):7228-35.

Stock et al., Ring1-mediated ubiquitination of H2A restrains poised RNA polymerase II at bivalent genese in mouse ES cells. Nat Cell Biol. 2007;9:1428-35. Supplementary Information 19 pages.

Takada et al., Flavopiridol suppresses tumor necrosis factor-induced activation of activator protein-1, c-Jun N-terminal kinase, p38 mitogen-activated protein kinase (MAPK), p44/p42 MAPK, and Akt, inhibits expression of antiapoptotic gene products, and enhances apoptosis through cytochrome c release and caspase activation in human myeloid cells. Mol Pharmacol. May 2008;73(5):1549-57. doi: 10.1124/mol.107.041350. Epub Feb. 20, 2008.

Takahashi et al., Induction of pluripotent stem cells from adult human fibroblasts by defined factors. Cell. Nov. 30, 2007;131(5):861-72.

Takahashi et al., Induction of pluripotent stem cells from mouse embryonic and adult fibroblast cultures by defined factors. Cell. Aug. 25, 2006;126(4):663-76. Epub Aug. 10, 2006.

Trova et al., Biaryl purine derivatives as potent antiproliferative agents: inhibitors of cyclin dependent kinases. Part I. Bioorg Med Chem Lett. 2009;19(23):6608-12.

Wada et al., DSIF, a novel transcription elongation factor that regulates RNA polymerase II processivity, is composed of human Spt4 and Spt5 homologs. Genes Dev. Feb. 1, 1998;12(3):343-56.

Wada et al., Evidence that P-TEFb alleviates the negative effect of DSIF on RNA polymerase II-dependent transcription in vitro. EMBO J. Dec. 15, 1998;17(24):7395-403.

Wade et al., the transition from transcriptional initiation to elongation. Curr Opin Genet Dev. Apr. 2008;18(2):130-6. Epub Feb. 20, 2008.

Wang et al., Improved low molecular weight Myc-Max inhibitors. Mol Cancer Ther. Sep. 2007;6(9):2399-408.

Wei et al., A novel CDK9-associated C-type cyclin interacts directly with HIV-1 Tat and mediates its high-affinity, loop-specific binding to TAR RNA. Cell. Feb. 20, 1998;92(4):451-62.

Wen et al., Transcription elongation factor hSPT5 stimulates mRNA capping. Genes Dev. Jul. 15, 1999;13(14):1774-9.

Wernig et al., In vitro reprogramming of fibroblasts into a pluripotent ES-cell-like state. Nature. Jul. 19, 2007;448(7151):318-24. Epub Jun. 6, 2007.

Wilson et al., DBD—taxonomically broad transcription factor predictions: new content and functionality. Nucleic Acids Res. Jan. 2008;36(Database issue):D88-92. Epub Dec. 11, 2007.

Wright et al., Upregulation of c-MYC in cis through a Large Chromatin Loop Linked to a Cancer Risk-Associated Single-Nucleotide Polymorphism in Colorectal Cancer Cells. Mol Cell Biol. Jan. 2010;30(6): 1411-1420.

Wu et al., NELF and DSIF cause promoter proximal pausing on the hsp70 promoter in *Drosophila*. Genes Dev. Jun. 1, 2003;17(11):1402-14.

Xu et al., A credit-card library approach for disrupting protein-protein interactions. Bioorg Med Chem. Apr. 15, 2006;14(8):2660-73. Epub Dec. 27, 2005.

Xu et al., Bidirectional promoters generate pervasive transcription in yeast. Nature. Feb. 19, 2009;457(7232):1033-7. Epub Jan. 25, 2009.

Yamada et al., P-TEFb-mediated phosphorylation of hSpt5 C-terminal repeats is critical for processive transcription elongation. Mol Cell. Jan. 20, 2006;21(2):227-37.

Yamaguchi et al., NELF, a multisubunit complex containing RD, cooperates with DSIF to repress RNA polymerase II elongation. Cell. Apr. 2, 1999;97(1):41-51.

Yin et al., Low molecular weight inhibitors of Myc-Max interaction and function. Oncogene. Sep. 18, 2003;22(40):6151-9.

Yoshida et al., Multiple viral strategies of HTLV-1 for dysregulation of cell growth control. Annu Rev Immunol. 2001;19:475-96.

Zeitlinger et al., RNA polymerase stalling at developmental control genes in the *Drosophila melanogaster* embryo. Nat Genet. Dec. 2007;39(12):1512-6. Epub Nov. 11, 2007.

Zhang et al., Model-based analysis of ChIP-Seq (MACS). Genome Biol. 2008;9(9):R137. Epub Sep. 17, 2008.

Zhang et al., A model of repression: CTD analogs and PIE-1 inhibit transcriptional elongation by P-TEFb. Genes Dev. Mar. 15, 2003;17(6):748-58.

Zhou et al., Tax interacts with P-TEFb in a novel manner to stimulate human T-lymphotropic virus type 1 transcription. J Virol. May 2006;80(10):4781-91.

Zhu et al., the human PAF complex coordinates transcription with events downstream of RNA synthesis. Genes Dev. Jul. 15, 2005;19(14):1668-73.

RNA Pol II (all) ChIP-seq

FIG. 8A

Top 200 cMyc target genes

| chrom | ID1 | ID2 |
|---|---|---|
| chr1 | NM_008972 | Ptma |
| chr6 | NM_011865 | Pcbp1 |
| chr4 | NM_130889 | Anp32b |
| chr7 | NM_023133 | Rps19 |
| chr1 | NM_133819 | Ppp1r15b |
| chr19 | NM_177420 | Psat1 |
| chr1 | NM_010880 | Ncl |
| chr2 | NM_001134869 | ENSMUSG00000069682 |
| chr2 | NM_009076 | Rpl12 |
| chr2 | NM_199302 | Lrsam1 |
| chr15 | NM_010447 | Hnrnpa1 |
| chr15 | NM_001039129 | Hnrnpa1 |
| chr7 | NM_009438 | Rpl13a |
| chr15 | NM_001076789 | Cbx5 |
| chr17 | NM_011287 | Rpl10a |
| chr18 | NM_010481 | Hspa9 |
| chr7 | NM_013725 | Rps11 |
| chr11 | NM_023743 | Eif4enif1 |
| chr17 | NM_010238 | Brd2 |
| chr17 | NM_001025387 | Brd2 |
| chr2 | NM_028984 | 8430406I07Rik |
| chr2 | NM_024225 | Snx5 |
| chr13 | NM_172015 | Iars |
| chr7 | NM_007527 | Bax |
| chr14 | NM_001081251 | Pbrm1 |
| chr14 | NM_153547 | Gnl3 |
| chr10 | NM_001077363 | Ptbp1 |
| chr10 | NM_008956 | Ptbp1 |
| chr8 | NM_019883 | Uba52 |
| chr8 | NM_001105157 | OTTMUSG00000004411 |
| chr8 | NM_001039514 | Dhps |
| chr4 | NM_134151 | Yars |

200 non-cMyc target genes

| chrom | ID1 | ID2 |
|---|---|---|
| chrX | NM_009530 | Atrx |
| chr9 | NM_030730 | Rad54l2 |
| chr13 | NM_021886 | Cenph |
| chr15 | NM_028003 | Rpap3 |
| chr8 | NM_172754 | AI449175 |
| chr9 | NM_009945 | Cox7a2 |
| chr18 | NM_013594 | Mbd1 |
| chr10 | NM_001081346 | Rtkn2 |
| chr8 | NM_001045553 | AI449175 |
| chr12 | NM_206534 | Churc1 |
| chr7 | NM_028031 | Zdhhc13 |
| chr1 | NM_023884 | Ralgps2 |
| chr4 | NM_008228 | Hdac1 |
| chr16 | NM_029090 | Nat15 |
| chr14 | NM_025550 | Psmd6 |
| chrX | NM_013898 | Timm8a1 |
| chr18 | NM_015805 | Atp9b |
| chrX | NM_026662 | Prps2 |
| chr6 | NM_023547 | Ino80b |
| chr15 | NM_011653 | Tuba1a |
| chr9 | NM_153799 | Edc3 |
| chrX | NM_019443 | Ndufa1 |
| chr7 | NM_001008549 | BC043301 |
| chr9 | NM_001110309 | Zfp426 |
| chr7 | NM_016978 | Oat |
| chr5 | NM_020570 | Xrcc2 |
| chr4 | NM_172871 | Klhl9 |
| chr9 | NM_146221 | Zfp426 |
| chr18 | NM_026302 | Dctn4 |
| chr1 | NM_009418 | Tpp2 |
| chr12 | NM_001110239 | Acp1 |
| chr11 | NM_011343 | Sec61g |

FIG. 8B

| | | | | | |
|---|---|---|---|---|---|
| chr4 | NM_029036 | S100pbp | chr4 | NM_133707 | 1810019J16Rik |
| chr11 | NM_134011 | Tbrg4 | chr4 | NM_025849 | 3110001D03Rik |
| chr11 | NM_001130457 | Tbrg4 | chr4 | NM_001083916 | 1810019J16Rik |
| chr8 | NM_145412 | 5830457O10Rik | chr1 | NM_001013779 | Aim2 |
| chr8 | NM_011574 | Cirh1a | chrX | NM_018794 | Atp6ap1 |
| chr16 | NM_001080999 | Trmt2a | chr4 | NM_152812 | Otud6b |
| chr16 | NM_001081000 | Trmt2a | chr12 | NM_021330 | Acp1 |
| chr16 | NM_008307 | Trmt2a | chr2 | NM_021335 | Snrpb2 |
| chr8 | NM_001111116 | OTTMUSG00000021609 | chr11 | NM_134189 | Galnt10 |
| chr16 | NM_011239 | Ranbp1 | chr16 | NM_001025615 | Ccdc50 |
| chr8 | NM_029751 | Rpl18a | chr11 | NM_001109972 | Sec61g |
| chr5 | NM_009391 | Ran | chr11 | NM_001109971 | Sec61g |
| chr16 | NM_031182 | Tcfap4 | chr3 | NM_028136 | Dhx36 |
| chr8 | NM_010499 | Ier2 | chr10 | NM_001109747 | 2610036L11Rik |
| chr19 | NM_025463 | 1810009A15Rik | chrX | NM_001105196 | Tcfe3 |
| chr17 | NM_016660 | Hmga1 | chr2 | NM_021526 | Psmd14 |
| chr17 | NM_001025427 | Hmga1 | chrX | NM_025703 | Tceal8 |
| chr17 | NM_001039356 | Hmga1 | chrX | NM_172472 | Tcfe3 |
| chr6 | NM_145569 | Mat2a | chr7 | NM_026734 | Tmem126b |
| chr4 | NM_173867 | Rcc2 | chrX | NM_001082412 | Mcart6 |
| chr15 | NM_033074 | Tars | chr17 | NM_009547 | Zfp101 |
| chr7 | NM_009516 | Wee1 | chr14 | NM_001029990 | Mett11d1 |
| chr3 | NM_008303 | Hspe1 | chr16 | NM_026202 | Ccdc50 |
| chr19 | NM_176843 | Ints5 | chr18 | NM_018821 | Socs6 |
| chr17 | NM_011296 | Rps18 | chr17 | NM_026417 | Yipf4 |
| chr1 | NM_010477 | Hspd1 | chrX | NM_021463 | Prps1 |
| chr11 | NM_181582 | Eif5a | chr12 | NM_026327 | 1810048J11Rik |
| chr11 | NM_008143 | Gnb2l1 | chr12 | NM_145442 | Mbip |
| chr9 | NM_011029 | Rpsa | chr11 | NM_198936 | Slu7 |
| chr11 | NM_016776 | Mybbp1a | chrX | NM_152822 | Las1l |
| chr11 | NM_022891 | Rpl23 | chr10 | NM_025418 | Vta1 |
| chr11 | NM_001048057 | Rpl38 | chrX | NM_018798 | Ubqln2 |
| chr11 | NM_023372 | Rpl38 | chrX | NM_133987 | Slc6a8 |
| chr6 | NM_172086 | Rpl32 | chr6 | NM_007604 | Capza2 |
| chr11 | NM_001048058 | Rpl38 | chrX | NM_010273 | Gdi1 |

FIG. 8C

| | | | | | | |
|---|---|---|---|---|---|---|
| chr11 | NM_026708 | Ticd1 | | chr1 | NM_016716 | Cul3 |
| chr8 | NM_022331 | Herpud1 | | chr4 | NM_001113412 | Fggy |
| chr11 | NM_133796 | Arhgdia | | chr6 | NM_024260 | Ccdc132 |
| chr10 | NM_181423 | Supv3l1 | | chr14 | NM_026936 | Oxa1l |
| chr11 | NM_011192 | Psme3 | | chr15 | NM_027212 | Med30 |
| chr6 | NM_007624 | Cbx3 | | chr8 | NM_198308 | 4930402E16Rik |
| chr12 | NM_001013372 | Nrp | | chr6 | NM_009748 | Bet1 |
| chr6 | NM_016806 | Hnrnpa2b1 | | chr7 | NM_011746 | Mkrn3 |
| chr6 | NM_182650 | Hnrnpa2b1 | | chr10 | NM_153395 | Mon2 |
| chr9 | NM_026507 | Zwilch | | chr2 | NM_153405 | Rbm45 |
| chr12 | NM_026958 | 1810035L17Rik | | chr14 | NM_016700 | Mapk8 |
| chr19 | NM_008577 | Slc3a2 | | chr12 | NM_007861 | Dld |
| chr12 | NM_001102565 | Alkbh1 | | chr3 | NM_201638 | G430022H21Rik |
| chr1 | NM_018868 | Nol5 | | chrX | NM_008222 | Hccs |
| chr2 | NM_024193 | Nol5a | | chrX | NM_016783 | Pgrmc1 |
| chr9 | NM_024212 | Rpl4 | | chr11 | NM_148673 | Slu7 |
| chr17 | NM_021322 | Wdr4 | | chr8 | NM_013522 | Frg1 |
| chr5 | NM_019647 | Rpl21 | | chr6 | NM_026490 | Mrpl19 |
| chr4 | NM_009098 | Rps8 | | chrX | NM_177592 | Tmem164 |
| chr1 | NM_173424 | Zbtb37 | | chr4 | NM_026534 | Ubxn2b |
| chr7 | NM_009081 | Rpl28 | | chr7 | NM_009989 | Cyct |
| chr3 | NM_009517 | Zmat3 | | chr15 | NM_019635 | Stk3 |
| chr7 | NM_020011 | Sphk2 | | chrX | NM_011276 | Rnf12 |
| chr10 | NM_001081056 | Xpot | | chr3 | NM_020007 | Mbnl1 |
| chr8 | NM_026904 | Anapc10 | | chrX | NM_173376 | Rbmx2 |
| chr11 | NM_207523 | Rpl23a | | chrX | NM_001081979 | Mecp2 |
| chr8 | NM_015751 | Abce1 | | chr18 | NM_025581 | 2810433K01Rik |
| chr7 | NM_203280 | Sphk2 | | chrX | NM_010788 | Mecp2 |
| chr7 | NM_009077 | Rpl18 | | chr10 | NM_008517 | Lta4h |
| chr11 | NM_144958 | Elf4a1 | | chr16 | NM_133752 | Opa1 |
| chr15 | NM_012053 | Rpl8 | | chr17 | NM_001081071 | Lycat |
| chr15 | NM_026069 | Rpl37 | | chrX | NM_023132 | Renbp |
| chr9 | NM_027261 | Taf1d | | chr2 | NM_030234 | Wdr76 |
| chr8 | NM_016738 | Rpl13 | | chr5 | NM_019824 | Arpc3 |
| chr9 | NM_029248 | Taf1d | | chrX | NM_172441 | Shroom2 |

FIG. 8D

| | | | | | |
|---|---|---|---|---|---|
| chr7 | NM_029384 | 2210411K11Rik | chr10 | NM_198021 | Scyl2 |
| chr2 | NM_009883 | Cebpb | chr12 | NM_029825 | Scfd1 |
| chr11 | NM_008722 | Npm1 | chr18 | NM_181414 | Pik3c3 |
| chr7 | NM_011975 | Rpl27a | chr11 | NM_026576 | Etaa1 |
| chr10 | NM_172308 | Mthfd1l | chrX | NM_025437 | Eif1ay |
| chr8 | NM_007918 | Eif4ebp1 | chr16 | NM_026254 | Tbc1d23 |
| chr6 | NM_001113566 | Serbp1 | chr6 | NM_019879 | Suclg1 |
| chr6 | NM_001113565 | Serbp1 | chr1 | NM_010633 | Uhmk1 |
| chr6 | NM_001113564 | Serbp1 | chrX | NM_007927 | Emd |
| chr9 | NM_010106 | Eef1a1 | chr6 | NM_009443 | Tgoln1 |
| chr6 | NM_008084 | Gapdh | chr7 | NM_198613 | Ap2s1 |
| chr15 | NM_013762 | Rpl3 | chr6 | NM_175277 | Bola3 |
| chr6 | NM_025814 | Serbp1 | chr13 | NM_001081058 | Cdc2l5 |
| chr17 | NM_011690 | Vars | chr2 | NM_026220 | Mfap1a |
| chr15 | NM_009083 | Rpl30 | chrX | NM_010685 | Lamp2 |
| chr9 | NM_021789 | Trappc4 | chr14 | NM_021328 | Bin3 |
| chr7 | NM_009201 | Slc1a5 | chrX | NM_001017959 | Lamp2 |
| chr9 | NM_024266 | Rps25 | chr13 | NM_027118 | Cdc2l5 |
| chr6 | NM_180678 | Gars | chr13 | NM_133905 | Papd4 |
| chr8 | NM_197982 | Ddx39 | chrX | NM_011712 | Wbp5 |
| chr6 | NM_013493 | Cnbp | chr10 | NM_172784 | Lrp11 |
| chr6 | NM_001109745 | Cnbp | chrX | NM_181516 | Taz |
| chr6 | NM_001109746 | Cnbp | chr12 | NM_178392 | Snapc1 |
| chr3 | NM_009836 | Cct3 | chr10 | NM_001033474 | ENSMUSG00000007 |
| chr7 | NM_022654 | Lrdd | chr6 | NM_133939 | Lsm8 |
| chr10 | NM_011295 | Rps12 | chr6 | NM_009444 | Tgoln2 |
| chr17 | NM_016844 | Rps28 | chr14 | NM_027045 | Gcap14 |
| chr14 | NM_207635 | Rps24 | chr2 | NM_012032 | Serinc3 |
| chr14 | NM_207634 | Rps24 | chr12 | NM_001014973 | Snx13 |
| chr18 | NM_020600 | Rps14 | chr18 | NM_172627 | Pggt1b |
| chr14 | NM_011297 | Rps24 | chr5 | NM_001081422 | A230054D04Rik |
| chr17 | NM_023202 | Ndufa7 | chr13 | NM_019671 | Net1 |
| chr10 | NM_028230 | Shmt2 | chrX | NM_019791 | Maged1 |
| chr11 | NM_177325 | Tsr1 | chrX | NM_012005 | Med14 |
| chr7 | NM_026270 | Akt1s1 | chr19 | NM_029648 | D19Ertd737e |

FIG. 8E

| | | | | | |
|---|---|---|---|---|---|
| chr10 | NM_025317 | Mrpl54 | chrX | NM_009481 | Usp9x |
| chr11 | NM_019574 | Patz1 | chrX | NM_009173 | Siah1b |
| chr10 | NM_007907 | Eef2 | chrX | NM_001077712 | Stag2 |
| chr7 | NM_001042655 | Tbc1d17 | chrX | NM_001048208 | Med14 |
| chr6 | NM_133928 | Chchd4 | chr13 | NM_146231 | Zfp825 |
| chr7 | NM_026020 | Rplp2 | chrX | NM_007451 | Slc25a5 |
| chr7 | NM_030693 | Atf5 | chr6 | NM_009169 | Shfm1 |
| chr10 | NM_013595 | Mbd3 | chr7 | NM_022985 | Zfand6 |
| chr17 | NM_028244 | Rrp1b | chr17 | NM_176962 | 6330416L07Rik |
| chr7 | NM_053074 | NupG2 | chr10 | NM_026482 | Atp2b1 |
| chr8 | NM_145390 | Tnpo2 | chrX | NM_178794 | Zrsr2 |
| chr8 | NM_001122843 | Tnpo2 | chr8 | NM_030254 | Tusc3 |
| chr8 | NM_133255 | Hook2 | chrX | NM_009453 | Zrsr2 |
| chr8 | NM_025465 | 1810029B16Rik | chr17 | NM_028543 | 1700065O13Rik |
| chr17 | NM_008302 | Hsp90ab1 | chrX | NM_173747 | Gpkow |
| chr6 | NM_133834 | Hnrnpf | chr9 | NM_027448 | Lca5 |
| chr15 | NM_011654 | Tuba1b | chr7 | NM_026112 | Zfp606 |
| chr10 | NM_134003 | Zc3h10 | chr7 | NM_080443 | Asb7 |
| chr9 | NM_145610 | Ppan | chr1 | NM_023284 | Nuf2 |
| chr6 | NM_028766 | Tmem43 | chrX | NM_021465 | Stag2 |
| chr15 | NM_026468 | Atp5g2 | chr9 | NM_029434 | Lca5 |
| chr8 | NM_024214 | Tomm20 | chr8 | NM_027171 | 2310057J16Rik |
| chr17 | NM_019693 | Bat1a | chr7 | NM_001039951 | Zfp606 |
| chr4 | NM_025334 | Txndc12 | chr12 | NM_177806 | Prpf39 |
| chr8 | NM_001111066 | Fkbp8 | chrX | NM_008853 | Pja1 |
| chr2 | NM_001111292 | Caprin1 | chrX | NM_011081 | Piga |
| chr2 | NM_001111290 | Caprin1 | chr17 | NM_177359 | Zfp799 |
| chr11 | NM_008907 | Ppia | chrX | NM_001083110 | Pja1 |
| chr8 | NM_010223 | Fkbp8 | chr12 | NM_028314 | 2700097O09Rik |
| chr2 | NM_001111289 | Caprin1 | chrX | NM_019736 | Acot9 |
| chr11 | NM_009423 | Traf4 | chr8 | NM_011369 | Shcbp1 |
| chr2 | NM_016739 | Caprin1 | chr8 | NM_001080930 | Atxn1l |
| chr2 | NM_001111291 | Caprin1 | chrX | NM_009483 | Utx |
| chr10 | NM_018860 | Rpl41 | chrX | NM_146235 | Ercc6l |
| chr7 | NM_170669 | Rps15a | chrX | NM_009767 | Chic1 |

FIG. 8F

| | | | | | | |
|---|---|---|---|---|---|---|
| chr8 | NM_029768 | Use1 | chr3 | NM_018877 | Setdb1 |
| chr4 | NM_027453 | Btf3l4 | chrX | NM_027181 | Pin4 |
| chr19 | NM_053086 | Nolc1 | chr2 | NM_026045 | Prpf18 |
| chr19 | NM_001039352 | Nolc1 | chr13 | NM_134063 | BC016423 |
| chr8 | NM_025917 | Use1 | chrX | NM_025932 | Syap1 |
| chr19 | NM_001039353 | Nolc1 | chrX | NM_010833 | Msn |
| chr19 | NM_001039351 | Nolc1 | chr1 | NM_026367 | Gpatch2 |
| chr12 | NM_177374 | 6720458F09Rik | chr2 | NM_001081975 | Mfap1b |
| chr8 | NM_026014 | Cdt1 | chrX | NM_025937 | Nkap |
| chr12 | NM_001099793 | 6720458F09Rik | chrX | NM_175044 | Bcor |
| chr12 | NM_001099792 | 6720458F09Rik | chrX | NM_175045 | Bcor |
| chr9 | NM_011099 | Pkm2 | chrX | NM_175046 | Bcor |
| chr8 | NM_010322 | Gnpat | chrX | NM_029510 | Bcor |
| chr8 | NM_001081164 | Otud4 | chrX | NM_207625 | Acsl4 |
| chr18 | NM_027350 | Nars | chrX | NM_001033600 | Acsl4 |
| chr8 | NM_025615 | 2810004N23Rik | chrX | NM_019477 | Acsl4 |
| chr15 | NM_025536 | Commd5 | chrX | NM_001110142 | Cul4b |
| chr17 | NM_008503 | Rps2 | chrX | NM_001033422 | Thoc2 |
| chr19 | NM_026007 | Eef1g | chrX | NM_028288 | Cul4b |
| chr12 | NM_010480 | Hsp90aa1 | chrX | NM_011692 | Vbp1 |
| chr19 | NM_009032 | Rbm4 | chrX | NM_019773 | Rab9 |
| chr2 | NM_026499 | Sfrs6 | chrX | NM_001098723 | Yy2 |
| chr2 | NM_001081005 | 1500012F01Rik | chrX | NM_030066 | Armcx1 |
| chr5 | NM_172722 | C330023M02Rik | chrX | NM_008150 | Gpc4 |
| chr2 | NM_001033196 | Znfx1 | chr14 | NM_013632 | Pnp1 |
| chr17 | NM_175934 | Ppp1r10 | chr7 | NM_001034893 | EG435970 |
| chr18 | NM_053261 | Impa2 | chrX | NM_013556 | Hprt1 |
| chr7 | NM_019830 | Prmt1 | chr7 | NM_023363 | 2810426N06Rik |

Average gene binding

FIG. 13A
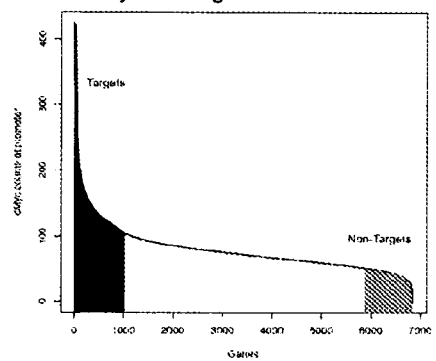
c-Myc binding at Active Genes
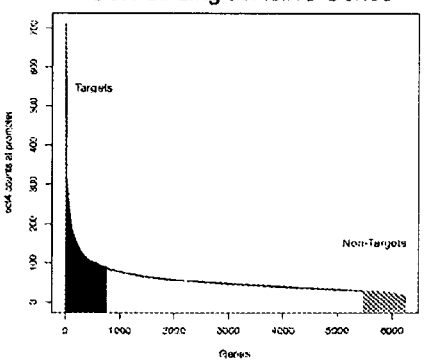
Oct4 binding at Active Genes
FIG. 13B
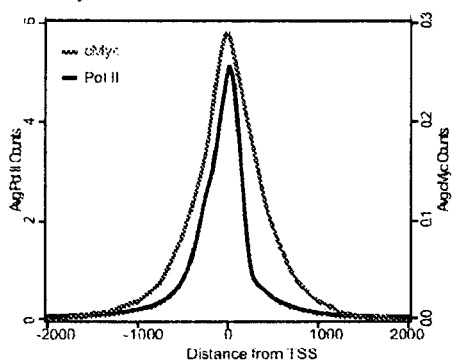
cMyc binds at the TSS
FIG. 13C
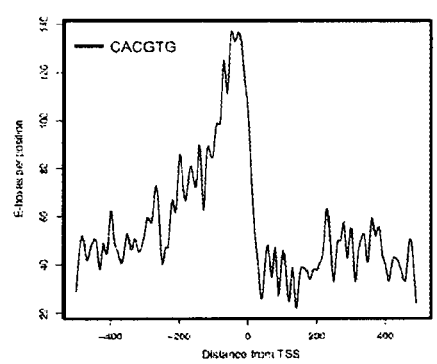
E-box distribution is near the TSS

SEQUENCE LISTING

```
<160> NUMBER OF SEQ ID NOS: 17

<210> SEQ ID NO 1
<211> LENGTH: 10
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
```

```
<222> LOCATION: (5)..(5)
<223> OTHER INFORMATION: n is a, c, g, or t

<400> SEQUENCE: 1 gggrnwyycc                                                              10

<210> SEQ ID NO 2
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 2
ttagttcccg gacctgttg                                                    19

<210> SEQ ID NO 3
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 3
acaaactcgt cccaccaag                                                    19

<210> SEQ ID NO 4
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 4
cctggagggc gtttttagt                                                    19

<210> SEQ ID NO 5
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 5
accctttcgg aacgtaacc                                                    19

<210> SEQ ID NO 6
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 6
gatcactcag aacggacacc                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 7
acacgctagg cgtaaagttg                                                   20
```

<210> SEQ ID NO 8
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 8
ctgggtctcc attgtctgg                                                19

<210> SEQ ID NO 9
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 9
agttccacca acctgctca                                                19

<210> SEQ ID NO 10
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 10
ggctccgaaa agatgtgaa                                                19

<210> SEQ ID NO 11
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 11
agcagaggtc gccctaaat                                                19

<210> SEQ ID NO 12
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 12
gtctccgaag gtcccatct                                                19

<210> SEQ ID NO 13
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 13
tgaaggctaa agggcatgt                                                19

<210> SEQ ID NO 14
<211> LENGTH: 19
<212> TYPE: DNA
<213> ORGANISM: Artificial Sequence
<220> FEATURE:
<223> OTHER INFORMATION: Synthetic Polynucleotide

```
<400> SEQUENCE: 14
agatcctgga ccgacttcc                                                19

<210> SEQ ID NO 15
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 15
gttcccaaaa ccttcgttg                                                19

<210> SEQ ID NO 16
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 16
agagcctaaa aggtcctcca                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 17
caccttctcc ctcctcttc                                                20
```

US 9,155,724 B2

COMBINATION METHODS FOR TREATMENT OF DISEASE

RELATED APPLICATIONS

This application is a national stage filing under 35 U.S.C. §371 of international PCT application, PCT/US2011/023804, file Feb. 4, 2011, which claims priority under 35 U.S.C. §119(e) to U.S. provisional application Ser. No. 61/302,061, filed Feb. 5, 2010, and U.S. provisional application Ser. No. 61/301,978, filed on Feb. 5, 2010, the entire contents of each of which are incorporated by reference herein.

GOVERNMENT FUNDING

This invention was made at least in part with government support from National Institute of Health grant RO1-HG002668. The government has certain rights in the invention.

BACKGROUND OF THE INVENTION

Many genetic and epigenetic changes that cause defects in the regulation of cell survival, proliferation, or differentiation and contribute to the development or progression of cancer have been identified. Although some notable successes in applying this knowledge to develop new treatments have been achieved, there remains a need in the art for advances in therapy for cancer and other proliferative diseases.

SUMMARY OF THE INVENTION

The invention provides a method of inhibiting proliferation or survival of a cell comprising contacting the cell with a P-TEFb inhibitor and a c-Myc inhibitor. In some embodiments, the P-TEFb inhibitor is a CDK9 inhibitor, e.g., flavopiridol or a flavopiridol analog. In some embodiments, the c-Myc inhibitor is a compound that inhibits interaction between c-Myc and Max. In some embodiments, the cell is a mammalian cell, e.g., a human cell. In some embodiments the cell is a tumor cell.

In another aspect, the invention provides a method of inhibiting pause release at a plurality of Myc target genes in a cell comprising contacting the cell with a P-TEFb inhibitor and a c-Myc inhibitor. In some embodiments the P-TEFb inhibitor is a CDK9 inhibitor.

In some embodiments the P-TEFb inhibitor is flavopiridol or a flavopiridol analog. In some embodiments the c-Myc inhibitor is a compound that inhibits interaction between c-Myc and Max. In some embodiments the cell is a mammalian cell, e.g., a human cell. In some embodiments the cell is a human cell. In some embodiments the cell is a tumor cell. In some embodiments the cell is a stem cell. In some embodiments the cell is contacted with a P-TEFb inhibitor at a concentration that does not substantially inhibit pause release at non-c-Myc target genes when contacted with the cell in the absence of a c-Myc inhibitor.

The invention further provides a method of treating a subject suffering from a proliferative disease comprising administering therapeutically effective amounts of a P-TEFb inhibitor and a c-Myc inhibitor to the subject. In some embodiments the amount of the P-TEFb inhibitor, the c-Myc inhibitor, or both, is sub-therapeutic when administered as a single agent, and/or when administered in the absence of the other compound. In some embodiments the proliferative disease is a tumor. In some embodiments the P-TEFb inhibitor is a CDK9 inhibitor. In some embodiments the P-TEFb inhibitor is flavopiridol or a flavopiridol analog. In some embodiments the c-Myc inhibitor is a compound that inhibits interaction between c-Myc and Max. In some embodiments the P-TEFb inhibitor is administered at a reduced dose relative to a standard dosing regimen. In some embodiments the subject is a human.

The invention further provides a composition comprising a P-TEFb inhibitor and a c-Myc inhibitor. In some embodiments the P-TEFb inhibitor is a CDK9 inhibitor. In some embodiments the P-TEFb inhibitor is flavopiridol or a flavopiridol analog. In some embodiments the c-Myc inhibitor is a compound that inhibits interaction between c-Myc and Max. In some embodiments the composition is a pharmaceutical composition. In some embodiments the compostion further comprises cells.

The invention further provides a method for testing the ability of a compound combination to inhibit cell survival or proliferation, comprising (a) contacting one or more test cells with a P-TEFb inhibitor and a c-Myc inhibitor; and (b) assessing survival or proliferation of the one or more test cells. In some embodiments the one or more test cell(s) comprise tumor cell(s). In some embodiments the one or more test cell(s) comprise mammalian cells. In some embodiments the method comprises comparing the effect of the compound combination on one or more tumor cells with the effect of the compound combination on one or more non-tumor cells. In some embodiments the method further comprises: (c) comparing the ability of the compound combination to inhibit cell survival or proliferation with the ability of the P-TEFb inhibitor to inhibit cell survival or proliferation when used as a single agent at the same concentration; and (d) selecting the c-Myc inhibitor as an enhancer of the P-TEFb inhibitor if the compound combination inhibits cell survival or proliferation to a greater extent than does the P-TEFb inhibitor when used as a single agent at the same concentration.

The invention provides a method of inhibiting proliferation or survival of a cell comprising contacting the cell with a P-TEFb inhibitor and a NF-kB inhibitor. In some embodiments, the P-TEFb inhibitor is a CDK9 inhibitor, e.g., flavopiridol or a flavopiridol analog. In some embodiments the NF-kB inhibitor is a compound that inhibits interaction between NF-kB transcription factor family members (homodimerization or heterodimerization). In some embodiments, the cell is a mammalian cell, e.g., a human cell. In some embodiments the cell is a tumor cell.

In another aspect, the invention provides a method of inhibiting pause release at a plurality of Myc target genes in a cell comprising contacting the cell with a P-TEFb inhibitor and a NF-kB inhibitor. In some embodiments the P-TEFb inhibitor is a CDK9 inhibitor.

In some embodiments the P-TEFb inhibitor is flavopiridol or a flavopiridol analog. In some embodiments the NF-kB inhibitor is a compound that inhibits interaction between NF-kB transcription factor family members (homodimerization or heterodimerization). In some embodiments the cell is a mammalian cell, e.g., a human cell. In some embodiments the cell is a human cell. In some embodiments the cell is a tumor cell. In some embodiments the cell is a stem cell. In some embodiments the cell is contacted with a P-TEFb inhibitor at a concentration that does not substantially inhibit pause release at non-NF-kB target genes when contacted with the cell in the absence of a NF-kB inhibitor.

The invention further provides a method of treating a subject suffering from a proliferative disease comprising administering therapeutically effective amounts of a P-TEFb inhibitor and a NF-kB inhibitor to the subject. In some embodiments the amount of the P-TEFb inhibitor, the NF-kB inhibitor, or both, is sub-therapeutic when administered as a single agent, and/or when administered in the absence of the other compound. In some embodiments the proliferative disease is a tumor. In some embodiments the P-TEFb inhibitor is a CDK9 inhibitor. In some embodiments the P-TEFb inhibitor is flavopiridol or a flavopiridol analog. In some embodiments the NF-kB inhibitor is a compound that inhibits interaction between NF-kB transcription factor family members (homodimerization or heterodimerization). In some embodiments the P-TEFb inhibitor is administered at a reduced dose relative to a standard dosing regimen. In some embodiments the subject is a human.

The invention further provides a composition comprising a P-TEFb inhibitor and a NF-kB inhibitor. In some embodiments the P-TEFb inhibitor is a CDK9 inhibitor. In some embodiments the P-TEFb inhibitor is flavopiridol or a flavopiridol analog. In some embodiments the NF-kB inhibitor is a compound that inhibits interaction between NF-kB transcription factor family members (homodimerization or heterodimerization). In some embodiments the composition is a pharmaceutical composition. In some embodiments the composition further comprises cells.

The invention further provides a method for testing the ability of a compound combination to inhibit cell survival or proliferation, comprising (a) contacting one or more test cells with a P-TEFb inhibitor and a NF-kB inhibitor; and (b) assessing survival or proliferation of the one or more test cells. In some embodiments the one or more test cell(s) comprise tumor cell(s). In some embodiments the one or more test cell(s) comprise mammalian cells. In some embodiments the method comprises comparing the effect of the compound combination on one or more tumor cells with the effect of the compound combination on one or more non-tumor cells. In some embodiments the method further comprises: (c) comparing the ability of the compound combination to inhibit cell survival or proliferation with the ability of the P-TEFb inhibitor to inhibit cell survival or proliferation when used as a single agent at the same concentration; and (d) selecting the NF-kB inhibitor as an enhancer of the P-TEFb inhibitor if the compound combination inhibits cell survival or proliferation to a greater extent than does the P-TEFb inhibitor when used as a single agent at the same concentration.

The invention further provides a method for testing the ability of a compound combination to inhibit inflammation, comprising (a) contacting one or more test cells with a P-TEFb inhibitor and a NF-kB inhibitor; and (b) assessing an inflammatory or immune response of the one or more test cells. In some embodiments the one or more test cell(s) comprise immune system cell(s). In some embodiments the one or more test cell(s) comprise mammalian cells. In some embodiments the method comprises comparing the effect of the compound combination on one or more immune system cells with the effect of the compound combination on one or more non-immune system cells. In some embodiments the method further comprises: (c) comparing the ability of the compound combination to inhibit an inflammatory or immune response with the ability of the P-TEFb inhibitor to inhibit an inflammatory or immune response when used as a single agent at the same concentration; and (d) selecting the NF-kB inhibitor as an enhancer of the P-TEFb inhibitor if the compound combination inhibits an inflammatory or immune response to a greater extent than does the P-TEFb inhibitor when used as a single agent at the same concentration. In some embodiments, an inflammatory or immune response comprises secretion of one or more cytokines, chemokines, prostaglandins, TNF alpha, or other inflammatory mediators, e.g., in response to a stimulus. In some embodiments, an inflammatory or immune response comprises a change in gene expression.

The practice of the present invention will typically employ, unless otherwise indicated, conventional techniques of molecular biology, cell culture, recombinant nucleic acid (e.g., DNA) technology, immunology, nucleic acid and polypeptide synthesis, detection, manipulation, and quantification, and RNA interference that are within the skill of the art. See, e.g., Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2008; Sambrook, Russell, and Sambrook, *Molecular Cloning: A Laboratory Manual*, $3^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988. Further information on cancer may be found in Cancer: Principles and Practice of Oncology (V. T. De Vita et al., eds., J. B. Lippincott Company, 7th ed., 2004 or 8th ed., 2008) and Weinberg, R A, The Biology of Cancer, Garland Science, 2006. All patents, patent applications, publications, references, databases, websites, etc., cited in the instant patent application are incorporated by reference in their entirety. In the event of a conflict or inconsistency with the specification, the specification shall control. The Applicants reserve the right to amend the specification based on any of the incorporated references and/or to correct obvious errors. None of the content of the incorporated references shall limit the invention.

BRIEF DESCRIPTION OF THE DRAWINGS

FIGS. 8A to 8F are a table showing the top 200 c-Myc target genes and 200 non-c-Myc target genes as determined by c-Myc binding using ChIP-Seq in mES cells.

FIGs. 13A to 13C. c-Myc occupies regions close to the TSS. (A) c-Myc and Oct4 binding at active genes ordered by amount of binding at the promoter (c-Myc+/−1 kb, Oct4 +/−5 kb). Target (black) and non-target (grey) gene sets are demarcated, which were used for subsequent analysis on Pol II ChIP-seq occupancy. (B) c-Myc (red) ChIP-seq occupancy is close to the TSS and the average Pol II promoter proximal peak (black). (C) Distribution of the canonical E-Box core sequence motif (CACGTG), which is recognized by c-Myc, near the TSS.

DETAILED DESCRIPTION OF CERTAIN EMBODIMENTS OF THE INVENTION

Figure 1A:
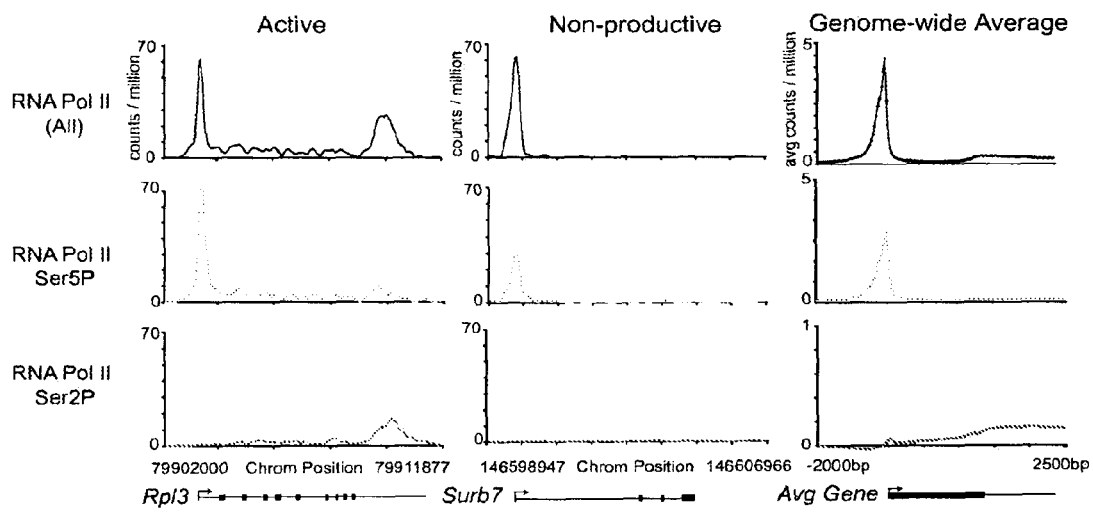
FIGS. 1A to 1C. Genome-wide occupancy of Pol II. (A) Occupancy of RNA Pol II (all), RNA Pol II Ser5P and RNA Pol II Ser2P in mES cells, as determined by ChIP-seq analysis. Enrichment at a representative active gene (Rpl3;chromosomal coordinates Refer to Chromosome 15) and non-productive gene (Surb7; chromosomal coordinates refer to Chromosome 6) is shown. Genome-wide binding averages (introns are not depicted in this representation), in 50 bp bins, are shown for each Pol II form to display the general binding patterns along the transcription unit from 2 kb upstream of the transcriptional start site to 2.5 kb downstream of the end of each annotated gene. The occupancy pattern shown for Ser5P and Ser2P is similar to previously reported ChIP analysis in other cell types (Glover-Cutter et al., 2008; Schones et al., 2008). (B) Schematic representation describing the calculation used to determine the traveling ratio (TR) at each Pol II bound gene in mES cells. The promoter proximal bin is defined using a fixed window from −30 bp to +300 bp around the annotated start site. The transcribed region (gene body) bin is from +300 bp to the annotated end. The TR is then calculated as the ratio of Pol II density in the promoter proximal bin by the Pol II density in the transcribed region bin. (C) Distribution of the percent of Pol II bound genes with a given TR. Approximately 91% of genes have a TR greater than 2, indicating the vast majority of Pol II bound genes have more Pol II in the promoter proximal region compared to the downstream transcribed region. See also FIG. 9.

I. Widespread Promoter-Proximal Pausing and its Regulation by c-Myc

Regulation of transcription is fundamental to the control of cellular gene expression programs. Recruitment of the RNA polymerase II (Pol II) transcription initiation apparatus to promoters by specific DNA binding transcription factors is generally recognized as a key regulatory step in selective transcription at most eukaryotic genes. Additional regulatory steps can occur subsequent to recruitment of the transcription apparatus, and these are known to play important roles in controlling the expression of a subset of genes.

For example, elongation is regulated at least in part by interactions between Pol II and transcription elongation factors. The largest subunit of Pol II contains a C-terminal domain (CTD) that is modified at various stages of the transcription process. Pol II is recruited into the preinitiation complex with a hypophosphorylated CTD, the CTD is phosphorylated on Serine 5 (Ser5) during initiation and then on Serine 2 (Ser2) during elongation. Positive elongation factor b (P-TEFb) is an enzyme complex containing cyclin-dependent kinase 9 (CDK9) and a cyclin (cyclin T1, T2a, T2b, or K). P-TEFb is responsible for phosphorylating the Pol II CTD on Ser2. Ser2-phosphorylated Pol II predominates in the body of a gene during productive elongation.

Promoter-proximal pausing of Pol II is a post-initiation regulatory event that has been well-studied at a small number of genes. "Promoter-proximal pausing" is used herein to refer to a state in which Pol II is bound to a promoter-proximal region but such binding does not result in productive elongation effective to generate a full length transcript. Promoter-proximal pausing can include events such as attenuation, stalling, poising, abortive elongation and promoter-proximal termination. In some aspects, promoter-proximal pausing refers to a state in which the forward movement of elongation-competent transcription complexes is temporarily blocked.

The *Drosophila* heat shock protein 70 (Hsp70) gene is regulated through both recruitment of the initiation apparatus and promoter-proximal pausing prior to the transition to elongation (Gilmour and L is, 1986; O'Brien and L is, 1991; Rougvie and L is, 1988). Paused Pol II molecules can also be detected in some human genes, including Myc, p21, β-globin and cad, in the absence of transcriptional activation (Bentley and Groudine, 1986; Eberhardy and Farnham, 2001, 2002; Espinosa et al., 2003; Sawado et al., 2003). At genes regulated through promoter-proximal pausing, the DRB-sensitivity inducing factor (DSIF) and negative elongation factor (NELF) generate a Pol II pause just downstream of the transcription start site (TSS) prior to elongation (Peterlin and Price, 2006; Wada et al., 1998a; Wu et al., 2003; Yamaguchi et al., 1999).

As described herein, using murine ES cells as a model system, the inventors have shown that promoter-proximal Pol II pausing occurs at a large population of genes, including at genes that are actively and fully transcribed. Further, it was discovered that the proto-oncogene c-Myc binds to approximately a third of actively transcribed genes and plays a key role in pause release at these genes via binding to and recruitment of P-TEFb. c-Myc is a transcription factor that is expressed in proliferating cells in response to mitogenic stimulation and becomes rapidly down regulated during cellular senescence or differentiation (Eilers and Eisenman, 2008; Meyer and Penn, 2008). Upon stimulation of proliferation, c-Myc is quickly re-expressed and stimulates cell growth. This tightly coupled regulation of c-Myc expression becomes deregulated in many cancers. c-Myc can also substantially enhance the efficiency of reprogramming of fibroblasts to induced pluripotent stem cells (Maherali et al., 2007; Takahashi et al., 2007; Takahashi and Yamanaka, 2006; Wernig et al., 2007). In ES cells, c-Myc occupies genes involved in these processes, similar to its target genes in other cell types (Chen et al., 2008; Kidder et al., 2008; Kim et al., 2008).

The invention encompasses the recognition that c-Myc binds to P-TEFb and plays a key role in Pol II pause release in proliferating cells, including at genes that are likely to play important roles in driving cell proliferation in diseases such as cancer that are characterized by aberrant or unwanted cell proliferation. The inventors' results suggest, among other things, that tumor cells that overexpress c-Myc, and cells that have experienced forced expression of c-Myc in reprogramming experiments, have enhanced expression of proliferation and metabolic genes due to the role of c-Myc in regulation of Pol II pause release at these target genes. The invention provides new insight into the mechanisms by which cell proliferation is controlled and identifies release of Pol II from promoter-proximal pausing ("pause release") as an important step in gene expression that can be modulated, e.g., inhibited, through the use of various agents such as small molecules and short interfering siRNA (siRNA), for a variety of purposes. For example, and without limitation, drugs that reduce the rate of Pol II pause release may help counteract the effects of c-Myc overexpression. In some aspects, the invention relates to targeting promoter-proximal pause release for treatment of disease, e.g., proliferative disease.

The invention provides a new approach to modulating, e.g., inhibiting, expression of c-Myc target genes, e.g., for inhibiting cell proliferation or survival or for other purposes. In some embodiments, expression of c-Myc target genes is inhibited for therapeutic purposes. In one aspect, the invention provides a method of inhibiting a c-Myc target gene in a cell comprising contacting the cell with a c-Myc inhibitor and a second compound, wherein the second compound inhibits pause release. In some embodiments, the second compound inhibits pause release by inhibiting P-TEFb. The methods may be used in vitro or in vivo, e.g., as described elsewhere herein, e.g., for treatment of disease, e.g., treatment of disease associated with aberrant c-Myc function, e.g., deviation of c-Myc function in a cell or subject relative to that found in a control, e.g., a normal, healthy cell or subject, which deviation contributes to a disease. In some embodiments, aberrant c-Myc function comprises increased c-Myc function. In some embodiments, aberrant c-Myc function comprises c-Myc-mediated transcription in cells wherein such transcription does not normally occur.

In some aspects, the invention relates to nuclear factor-kappa B (NF-kB). In some aspects, the invention relates to the role of NF-kB in regulating, e.g., promoting, pause release at its target gene(s), e.g., by recruiting a positive elongation factor, e.g., p-TEFb to such genes. The invention encompasses the recognition that inhibiting the ability of NF-kB to recruit P-TEFb to target genes would provide a means to maintain these genes in a nonproductive state. In some aspects, the invention relates to stimulus-induced NF-kB. NF-kB comprises a highly conserved family of dimeric transcription factors which act to broadly influence gene expression events associated with innate and adaptive immune responses, inflammation, cell growth, proliferation, and survival (Hayden, M. S, and S. Ghosh, Cell, 2008, 132(3):344-62). NF-kB is the nuclear effector of a network of proteins (sometimes termed the NF-kB signaling module) that respond to a wide range of extracellular stimuli in most, if not in all, cells (Hoffmann, A., et al., Science, 2002, 298(5596): 1241-5). The core components of NF-kB pathway include the IkB kinases (IKKs), the inhibitory κB proteins (IkBs), and the NF-kB family of transcription factors. The NF-kB transcription factor family consists of five members, p50, p52, p65 (RelA), c-Rel, and RelB, encoded by NF-kB1, NF-kB2, RELA, REL, and RELB, respectively, which share an N-terminal Rel homology domain (RHD) responsible for DNA binding and homo- and heterodimerization. The NF-kB1 and NF-kB2 proteins are synthesized as large precursors, p105, and p100, which undergo processing to generate the mature NF-kB subunits, p50 and p52. NF-kB dimers bind to kB consensus sequences 5' GGGRNWYYCC 3' (N—any base; R—purine; W—adenine or thymine; and Y—pyrimidine) (SEQ ID NO: 1) within the promoters and enhancers of target genes and regulate transcription through the recruitment of coactivators and corepressors (Hoffmann, A., G. Natoli, and G. Ghosh, 2006. 25(51): p. 6706-16). In unstimulated cells, NF-kB dimers are sequestered in the cytoplasm by a family of inhibitors, called IkBs (Inhibitor of kB). There proteins mask the nuclear localization signals (NLS) of NF-kB proteins and thereby keep them sequestered in an inactive state in the cytoplasm. The IkB family includes IkBα, IkBβ, IkBε, and Bc1-3, of which the major IkB protein is IkBα. The C-terminal halves of p105 and p100 can also function as IkB proteins. Activation of the NF-kB pathway is often initiated by the stimulus-induced degradation of IκB proteins. This occurs often via activation of IkB kinase (IKK). IKK is composed of a heterodimer of the catalytic IKK alpha and IKK beta subunits and a regulatory protein often referred to as NEMO (NF-kB essential modulator) or IKK gamma. When activated by signals, usually coming from the outside of the cell, the IKK phosphorylates two serine residues located in an IkB regulatory domain. When phosphorylated on these serines (e.g., serines 32 and 36 in human IkBα), the IkB inhibitor molecules are modified by ubiquitination, which leads to their degradation by the proteasome. The NF-kB complex is then able to enter the nucleus where it can activate the expression of genes that have appropriate DNA-binding sites. NF-kB target genes include a wide variety of cytokines and chemokines and their modulators, immunoreceptors, proteins involved in antigen presentation, cell adhesion molecules, acute phase proteins, stress response genes, cell-surface receptors, regulators of apoptosis, growth factors, ligands and their modulators, early response genes, transcription factors and regulators thereof, and others. The particular genes activated may differ, e.g., in different cell types or cell states. Activation of the genes then leads to the one or more physiological responses, e.g., an inflammatory or immune response, a cell survival response, and/or cellular proliferation. NF-kB signaling is involved in a wide variety of diseases in which inflammatory or immune responses are a contributing factor.

In some aspects, the invention provides a new approach to modulating, e.g., inhibiting, expression of NF-kB target genes, e.g., for inhibiting cell proliferation or survival, inhibiting inflammation, or for other purposes. In some embodiments, expression of NF-kB target genes is inhibited for therapeutic purposes, e.g., to treat any disease or disorder in which NF-kB activation plays a role, such as an inflammatory disease, autoimmune disease, or proliferative disease, e.g., cancer. In one aspect, the invention provides a method of inhibiting an NF-kB target gene in a cell comprising contacting the cell with a NF-kB inhibitor and a second compound, wherein the second compound inhibits pause release. In some embodiments, the second compound inhibits pause release by inhibiting P-TEFb. The methods may be used in vitro or in vivo, e.g., as described elsewhere herein, e.g., for treatment of disease, e.g., treatment of disease associated with aberrant NF-kB function, e.g., deviation of NF-kB function in a cell or subject relative to that found in a control, e.g., a normal, healthy cell or subject, which deviation contributes to a disease. In some embodiments, aberrant NF-kB function comprises increased NF-kB function. In some embodiments, aberrant NF-kB function comprises NF-kB-mediated transcription in cells wherein such transcription does not normally occur. In some embodiments, NF-kB function is activated by exposure to a stimulus, e.g., a pathogen, particle or environmental component (e.g, in dust or cigarette smoke), pharmaceutical agent, biological or chemical agent, pollutant, stress, etc. In some embodiments, an individual who has been exposed to such stimulus is treated according to the invention In some embodiments, the invention provides methods of modifying cell type. In various embodiments, a cell type can be any of the distinct forms of cell found in the body of a normal, healthy adult vertebrate, e.g., a mammal (e.g., a mouse of human) or avian. Typically, different cell types are distinguishable from each other based on one or more structural characteristics, functional characteristics, gene expression profile, proteome, secreted molecules, cell surface marker (and/or other marker) expression (e.g., CD molecules), or a combination of any of these. In general, members of a particular cell type display at least one characteristic not displayed by cells of other types or display a combination of characteristics that is distinct from the combination of characteristics found in other cell types. Members of the cell type are typically more similar to each other than they are to cells of different cell types. See, e.g., Young, B., et al., *Wheater's Functional Histology: A Text and Colour Atlas,* 5th ed. Churchill Livingstone, 2006, or Alberts, B., et al, *Molecular Biology of the Cell,* 4th ed, (2002) or 5th edition (2007), Garland Science, Taylor & Francis Group, for exemplary cell types and characteristic features thereof.

In some embodiments, a cell is of a cell type that is typically classified as a component of one of the four basic tissue types, i.e., connective, epithelial, muscle, and nervous tissue. In some embodiments of the invention, a cell is a connective tissue cell. Connective tissue cells include storage cells (e.g., brown or white adipose cells, liver lipocytes), extracellular matrix (ECM)-secreting cells (e.g., fibroblasts, chondrocytes, osteoblasts), and blood/immune system cells such as lymphocytes (e.g., T lymphocytes, B lymphocytes, or plasma cells), granulocytes (e.g., basophils, eosinophils, neutrophils), and monocytes. In some embodiments of the invention, a cell is an epithelial cell. Epithelial cell types include, e.g., gland cells specialized for secretion such as exocrine and endocrine glandular epithelial, and surface epithelial cells such as keratinizing and non-keratinizing surface epithelial cells. Nervous tissue cells include glia cells and neurons of the central or peripheral nervous system. Muscle tissue cells include skeletal, cardiac, and smooth muscle cells. Many of these cell types can be further divided. For example, T lymphocytes include helper, regulatory, and cytotoxic T cells. Cell types can be classified based on the germ layer from which they originate. In some embodiments, a cell is of endodermal origin. In some embodiments, a cell is of mesodermal origin. In some embodiments, a cell is of ectodermal origin. Cell types can be classified based on the germ layer from which they originate. In some embodiments, a cell is of endodermal origin. In some embodiments, a cell is of mesodermal origin. In some embodiments, a cell is of ectodermal origin. In some embodiments, a cell type is a stem cell, e.g., an adult stem cell. Exemplary adult stem cells include hematopoietic stem cells, neural stem cells, and mesenchymal stem cells. In some embodiments, a cell type is a mature, differentiated cell type. In some embodiments a cell is an adipocyte (e.g., white fat cell or brown fat cell), cardiac myocyte, chondrocyte, endothelial cell, exocrine gland cell, fibroblast, hair follicle cell, hepatocyte, keratinocyte, macrophage, monocyte, melanocyte, neuron, neutrophil, osteoblast, osteoclast, pancreatic islet cell (e.g., a beta cell), skeletal myocyte, smooth muscle cell, B cell, plasma cell, T lymphocyte (e.g., regulatory, cytotoxic, helper), or dendritic cell.

In some embodiments, the invention provides methods of modifying cell state. In some aspects, cell state reflects the fact that cells of a particular type can exhibit variability with regard to one or more features and/or can exist in a variety of different conditions, while retaining the features of their particular cell type and not gaining features that would cause them to be classified as a different cell type. The different states or conditions in which a cell can exist may be characteristic of a particular cell type (e.g., they may involve properties or characteristics exhibited only by that cell type and/or involve functions performed only or primarily by that cell type) or may occur in multiple different cell types. Sometimes a cell state reflects the capability of a cell to respond to a particular stimulus or environmental condition (e.g., whether or not the cell will respond, or the type of response that will be elicited) or is a condition of the cell brought about by a stimulus or environmental condition. Cells in different cell states may be distinguished from one another in a variety of ways. For example, they may express, produce, or secrete one or more different genes, proteins, or other molecules ("markers"), exhibit differences in protein modifications such as phosphorylation, acetylation, etc., or may exhibit differences in appearance. Thus a cell state may be a condition of the cell in which the cell expresses, produces, or secretes one or more markers, exhibits particular protein modification(s), has a particular appearance, or will or will not exhibit one or more biological response(s) to a stimulus or environmental condition. Markers can be assessed using methods well known in the art, e.g., gene expression can be assessed at the mRNA level using Northern blots, cDNA or oligonucleotide microarrays, or sequencing (e.g., RNA-Seq), or at the level of protein expression using protein microarrays, Western blots, flow cytometry, immunohistochemistry, etc. Modifications can be assessed, e.g., using antibodies that are specific for a particular modified form of a protein, e.g., phospho-specific antibodies, or mass spectrometry.

One example of cell state reflects the condition of cell (e.g., a muscle cell or adipose cell) as either sensitive or resistant to insulin. Insulin resistant cells exhibit decreased response to circulating insulin; for example insulin-resistant skeletal muscle cells exhibit markedly reduced insulin-stimulated glucose uptake and a variety of other metabolic abnormalities that distinguish these cells from cells with normal insulin sensitivity.

Another example of a cell state is proliferation state. For example, a cell could be in a state of proliferation or a state of arrest. In the case of proliferation, modifying cell state can refer to causing a cell in a state of arrest to start proliferating or causing a cell that is proliferating to enter a state of arrest or apoptosis or necrosis. In one aspect, inhibition of cell proliferation may refer to the prevention of proliferation of a non-proliferating cell (maintenance of a non-proliferating state) and/or the process of inhibiting the proliferation of a proliferating cell (process of effecting a proliferation state change). In other aspects, a cell state is a disease-associated state or a normal state.

Another example of cell state is "activated" state as compared with "resting" or "non-activated" state. Many cell types in the body have the capacity to respond to a stimulus by modifying their state to an activated state. The particular alterations in state may differ depending on the cell type and/or the particular stimulus. A stimulus could be any biological, chemical, or physical agent to which a cell may be exposed. A stimulus could originate outside an organism (e.g., a pathogen such as virus, bacteria, or fungi (or a component or product thereof such as a protein, carbohydrate, or nucleic acid, cell wall constituent such as bacterial lipopolysaccharide, etc) or may be internally generated (e.g., a cytokine, chemokine, growth factor, or hormone produced by other cells in the body or by the cell itself). For example, stimuli can include interleukins, interferons, or TNF alpha. Immune system cells, for example, can become activated upon encountering foreign (or in some instances host cell) molecules. Cells of the immune adaptive immune system can become activated upon encountering a cognate antigen (e.g., containing an epitope specifically recognized by the cell's T cell or B cell receptor) and, optionally, appropriate co-stimulating signals. Activation can result in changes in gene expression, production and/or secretion of molecules (e.g., cytokines, inflammatory mediators), and a variety of other changes that, for example, aid in defense against pathogens but can, e.g., if excessive, prolonged, or directed against host cells or host cell molecules, contribute to diseases. Fibroblasts are another cell type that can become activated in response to a variety of stimuli (e.g., injury (e.g., trauma, surgery), exposure to certain compounds including a variety of pharmacological agents, radiation, etc.) leading them, for example, to secrete extracellular matrix components. In the case of response to injury, such ECM components can contribute to wound healing. However, fibroblast activation, e.g., if prolonged, inappropriate, or excessive, can lead to a range of fibrotic conditions affecting diverse tissues and organs (e.g., heart, kidney, liver, intestine, blood vessels, skin) and/or contribute to cancer. The presence of abnormally large amounts of ECM components can result in decreased tissue and organ function, e.g., by increasing stiffness and/or disrupting normal structure and connectivity.

In some embodiments, the method is of use to treat, e.g., a metabolic, neurodegenerative, inflammatory, auto-immune, proliferative, infectious, cardiovascular, musculoskeletal, or other disease. It will be understood that diseases can involve multiple pathologic processes and mechanisms and/or affect multiple body systems. Discussion herein of a particular disease in the context of a particular pathologic process, mechanism, cell state, cell type, or affected organ, tissue, or system, should not be considered limiting. For example, a number of different tumors (e.g., hematologic neoplasms such as leukemias) arise from undifferentiated progenitor cells and/or are composed largely of undifferentiated or poorly differentiated cells that retain few if any distinctive features characteristic of differentiated cell types. These tumors, which are sometimes termed undifferentiated or anaplastic tumors, may be particularly aggressive and/or difficult to treat. In some embodiments of the invention, a method of the invention is used to modify such cells to a more differentiated state, which may be less highly proliferative and/or more amenable to a variety of therapies, e.g., chemotherapeutic agents. In another embodiment, an inventive method is used to treat insulin resistance which occurs, for example, in individuals suffering from type II diabetes and pre-diabetic individuals. It would be beneficial to modify the state of insulin-resistant cells towards a more insulin-sensitive state, e.g., for purposes of treating individuals who are developing or have developed insulin resistance. In another embodiment, an inventive method is used to treat obesity.

Many inflammatory and/or autoimmune conditions may occur at least in part as a result of excessive and/or inappropriate activation of immune system cells. Autoimmune diseases include, e.g., Graves disease, Hashimoto's thyroiditis, myasthenia gravis, rheumatoid arthritis, sarcoidosis, Sjögren's syndrome, scleroderma, ankylosing spondylitis, type I diabetes, vasculitis, and lupus erythematosus. Furthermore, immune-mediated rejection is a significant risk in organ and tissue transplantation. Inflammation plays a role in a large number of diseases and conditions. Inflammation can be acute (and may be recurrent) or chronic. In general, inflammation can affect almost any organ, tissue, or body system. For example, inflammation can affect the cardiovascular system (e.g., heart), musculoskeletal system, respiratory system (e.g., bronchi, lungs), renal system, (e.g., kidneys), eyes, nervous system, gastrointestinal system (e.g., colon), integumentary system (e.g., skin), musculoskeletal system (e.g., joints, muscles), resulting in a wide variety of conditions and diseases. Chronic inflammation is increasingly recognized as an important factor contributing to atherosclerosis and degenerative diseases of many types. Inflammation influences the microenvironment around tumours and contributes, e.g., to tumor cell proliferation, survival and migration. Epidemiological studies have demonstrated that chronic inflammation predisposes individuals to various types of cancer and an estimated 15-20% of all cancer deaths can be attributed to sustained infections and inflammatory responses (Balkwill, F. and A. Mantovani, Lancet, 2001, 357(9255): 539-45). Likewise, many non-infectious conditions of chronic inflammation increase the risk and accelerate the progression of tumor development (Naugler, W. E. and M. Karin, Curr Opin Genet Dev, 2008, 18(1): p. 19-26). Hallmarks of cancer-related inflammation include the presence of inflammatory cells and inflammatory mediators (chemokines, cytokines and prostaglandins) in tumour tissues, tissue remodeling and angiogenesis similar to that seen in chronic inflammatory responses, and tissue repair. Furthermore, chronic inflammation can eventually lead to fibrosis.

Exemplary inflammatory diseases include, e.g., adult respiratory distress syndrome (ARDS), atherosclerosis (e.g., coronary artery disease, cerebrovascular disease), allergies, asthma, cancer, demyleinating diseases, dermatomyositis, inflammatory bowel disease (e.g., Crohn's disease, ulcerative colitis), inflammatory myopathies, multiple sclerosis, glomerulonephritis, psoriasis, pancreatitis, rheumatoid arthritis, sepsis, vasculitis (including phlebitis and arteritis, e.g., polyarteritis nodosa, Wegener's granulomatosis, Buerger's disease, Takayasu's arteritis, etc.). In some embodiments, a method of the invention is used to modify immune cell state to reduce activation of immune system cells involved in such conditions and/or render immune system cells tolerant to one or more antigens. In one embodiment, dendritic cell state is altered. Promoting immune system activation using a method of the invention (e.g., in individuals who have immunodeficiencies or have been treated with drugs that deplete or damage immune system cells), potentially for limited periods of time, may be of benefit in the treatment of infectious diseases.

In other embodiments, activated fibroblasts are modified to a less activated cell state to reduce or inhibit fibrotic conditions or treat cancer.

Post-surgical adhesions can be a complication of, e.g., abdominal, gynecologic, orthopedic, and cardiothoracic surgeries. Adhesions are associated with considerable morbidity and can be fatal. Development of adhesions involves inflammatory and fibrotic processes. In some embodiments, a method of the invention is used to modify state of immune system cells and/or fibroblasts to prevent or reduce adhesion formation or maintenance.

In other embodiments, modifying cells to a more or less differentiated state is of use to generate a population of cells in vivo that aid in repair or regeneration of a diseased or damaged organ or tissue, or to generate a population of cells ex vivo that is then administered to a subject to aid in repair or regeneration of a diseased or damaged organ or tissue.

In some embodiments, cell type and or cells state becomes modified over the course of multiple cell cycle(s). In some embodiments, cell type and/or cell state is stably modified. For example, the modified type or state may persist for varying periods of time after the cell is no longer exposed to the agent(s) that caused the modification. In some embodiments, continued or at intermittent exposure to the agent(s) is required or helpful to maintain the modified state or type.

Cells may be in living animal, e.g., a mammal, or may be isolated cells. Isolated cells may be primary cells, such as those recently isolated from an animal (e.g., cells that have undergone none or only a few population doublings and/or passages following isolation), or may be a cell of a cell line that is capable of prolonged proliferation in culture (e.g., for longer than 3 months) or indefinite proliferation in culture (immortalized cells). In many embodiments, a cell is a somatic cell. Somatic cells may be obtained from an individual, e.g., a human, and cultured according to standard cell culture protocols known to those of ordinary skill in the art. Cells may be obtained from surgical specimens, tissue or cell biopsies, etc. Cells may be obtained from any organ or tissue of interest. In some embodiments, cells are obtained from skin, lung, cartilage, breast, blood, blood vessel (e.g., artery or vein), fat, pancreas, liver, muscle, gastrointestinal tract, heart, bladder, kidney, urethra, prostate gland. Cells may be maintained in cell culture following their isolation. In certain embodiments, the cells are passaged or allowed to double once or more following their isolation from the individual (e.g., between 2-5, 5-10, 10-20, 20-50, 50-100 times, or more) prior to their use in a method of the invention. They may be frozen and subsequently thawed prior to use. In some embodiments, the cells will have been passaged or permitted to double no more than 1, 2, 5, 10, 20, or 50 times following their isolation from the individual prior to their use in a method of the invention. Cells may be genetically modified or not genetically modified in various embodiments of the invention. Cells may be obtained from normal or diseased tissue. In some embodiments, cells are obtained from a donor, and their state or type is modified ex vivo using a method of the invention. The modified cells are administered to a recipient, e.g., for cell therapy purposes. In some embodiments, the cells are obtained from the individual to whom they are subsequently administered.

A population of isolated cells in any embodiment of the invention may be composed mainly or essentially entirely of a particular cell type or of cells in a particular state. In some embodiments, an isolated population of cells consists of at least 30%, 40%, 50%, 60%, 70%, 80%, 90%, 95%, 96%, 97%, 98%, 99%, or 100% cells of a particular type or state (i.e., the population is at least 30%, 40%, 50%, 60%, 70%, 80%, 90%, 95%, 96%, 97%, 98%, 99%, or 100% pure), e.g., as determined by expression of one or more markers or any other suitable method.

In some aspects, the invention relates to modulation of two or more transcriptional modulators in a cell. In some aspects, such modulation modulates cell state and/or cell type of the cell. A transcriptional modulator (TM) can be, e.g., any biomolecule or biomolecular complex that modulates, e.g., increases or decreases, the frequency, rate, or extent of transcription of one or more genes (or transcription units). For purposes of this invention "transcriptional modulator" typically refers to a biomolecule produced by a cell that modulates transcription in that cell. TMs are typically proteins, but other biomolecules such as nucleic acids may also serve as TMs. In some embodiments a TM may influence the transcription of only a few genes whereas in other embodiments a TM influences transcription of many genes. Some TMs may be expressed by only one or a few cell types and/or in one or a few cell states, whereas other TMs may be expressed by many or most cell types and/or in many or most cell states. In some embodiments, at least one TM is a transcription factor (TF), e.g., a transcription factor that binds to DNA (optionally in a complex such as a homodimer, heterodimer, or oligomer with one or more other proteins) and typically in a sequence-specific manner. In some embodiments, at least one TM is an initiation or elongation factor. In some embodiments, at least one of TM is a cell-type specific modulator (e.g., expressed selectively in a subset of cell lineages, e.g., neural, hematopoietic, to name but a few). In some embodiments, at least one TM is a co-activator. In general, a TM contains a domain that binds to (or is capable of binding to) DNA and/or physically interacts (e.g., via noncovalent binding) directly or indirectly with one or more other biomolecule(s), e.g., other transcriptional modulator(s) that bind to (or is/are capable of binding to) DNA. Two or more molecules are considered to physically interact in an indirect manner if they are not in direct physical contact but are both part of a multimolecular complex or structure comprising one or more additional molecule(s). TMs include, e.g., transcription factors (e.g., transcription factors that activate transcription of one or more target genes, and transcription factors that repress transcription of one or more target genes), transcription initiation factors, transcription elongation factors (which may be positive transcription elongation factors such as p-TEFb, or negative transcription elongation factors), transcription co-activators or co-repressors. For example, co-activators typically interact selectively and non-covalently with activating transcription factor(s) and also with the basal transcription machinery in order to increase the frequency, rate or extent of transcription. They generally do not bind DNA, but may instead, for example, mediate protein-protein interactions between activating transcription factors and the basal transcription machinery.

In some embodiments, at least one TM is regulated by a signaling pathway. A TF could be, e.g., a helix-loop-helix, helix-turn-helix, winged helix, leucine zipper, bZIP, zinc finger, or homeodomain protein. Exemplary transcriptional modulators are, e.g., TCF family members and Smad family members. Exemplary signaling pathways are the Wnt signaling pathway and the TGFb signaling pathway. One of skill in the art will be aware of numerous TFs and signaling pathways in animal cells, e.g., vertebrate cells, e.g., mammalian cells, and will also be aware of initiation factors and elongation factors for transcription in such cells. Transcription factors, for example, are listed in publicly available resources and databases such as Gene Ontology (http://www.geneontology.org/) or DBD (www.transcriptionfactor.org) (Wilson, et al, DBD—taxonomically broad transcription factor predictions: new content and functionality Nucleic Acids Research 2008 doi: 10.1093/nar/gkm964). Furthermore, one of skill in the art could readily obtain protein sequences for the proteins discussed herein and genomic and mRNA sequences encoding such proteins, e.g., in the Entrez databases (e.g., Gene, Protein, Nucleotide databases, e.g., GenBank, RefSeq) at the National Center for Biotechnology Information website (http://www.ncbi.nlm.nih.gov/).

In some embodiments, the invention comprises modulating a TF that binds to a positive elongation factor, e.g., p-TEFb, wherein the TF recruits the positive elongation factor to a gene and promotes pause release. In some embodiments, the invention comprises modulating a TF that binds to a negative elongation factor, e.g., NELF, wherein the TF recruits the negative elongation factor to a gene and maintains RNA polymerase in a paused state. In some aspects, the invention relates to identifying TFs that co-occupy genes with a positive elongation factor, e.g., P-TEFb, or a negative elongation factor, e.g., NELF. In some aspects, the invention relates to modulating a TF that co-occupies a gene with a positive elongation factor, e.g., P-TEFb or a negative elongation factor, e.g., NELF. In some aspects, the invention relates to modulating pause release as a means of modifying cell state or cell type, e.g., for therapeutic purposes. In some embodiments, such modulation is accomplished by modulating a transcription factor that recruits a positive or negative elongation factor to a gene and thereby promotes pause release or maintains RNA polymerase in a paused state, respectively.

"Modulating" a TM is typically accomplished by contacting a TM with a "modifier". Typically the contacting comprises contacting a cell that expresses the TM with the modifier. The cell may be contacted in culture (e.g., by culturing the cell in medium comprising the modifier) or contacted in vivo (i.e., to a cell that is part of a living animal, e.g., by administering the modifier to the animal). A "modifier" of a TM can be, e.g., an inhibitor or an activator, or a compound that in any way alters the activity or activity of c-Myc or the second transcriptional modulator, respectively. A modifier can be a small molecule, polypeptide, nucleic acid, lipid, carbohydrate, inorganic compound, or other type of molecule in various embodiments of the invention.

In some embodiments of interest, a TM is a cell-type specific TM. For example, the TM may be expressed selectively in one or a small number of cells types relative to expression in many or most other cell types. A cell type specific gene, e.g., TM, need not be expressed only in a single cell type but may be expressed in one or several, e.g., up to about 5, or about 10 different cell types of a vertebrate, e.g., a mammal, e.g., a human, or in up to about 1%, 2%, or 5-10% of the different cell types. In some embodiments a cell type specific gene is lineage specific, e.g., it is specific to a particular lineage (e.g., hematopoietic, neural, muscle, etc.) In some embodiments, a cell-type specific gene is a gene that is more highly expressed in a given cell type than in most (e.g., at least 80%, at least 90%, at least 95%, or more) or all other cell types of that organism. Thus specificity may relate to level of expression, e.g., a gene that is widely expressed at low levels but is highly expressed in certain cell types could be considered cell type specific to those cell types in which it is highly expressed. It will be understood that expression can be normalized based on total mRNA expression (optionally including miRNA transcripts) and/or based on expression of a housekeeping gene in a cell. In some embodiments, a gene is considered cell type specific for a particular cell type if it is expressed at levels at least 2, 5, or at least 10-fold greater in that cell than it is, on average, in at least 25%, at least 50%, at least 75%, at least 90% or more of the cell types of an adult of that species, or in a representative set of cell types. In some embodiments, a TM of interest is one whose expression is associated with a particular structural or functional characteristic or combination thereof that is characteristic of, or a defining feature of, a cell type or state For example, expression of the TM may be required in order for a cell to acquire and/or maintain one or more structural and/or functional characteristics that are considered essential elements or properties that identify the cell as being of a particular cell type (cell type or identity) and/or that identify the cell as being in a particular state (cell state). The TM may be one whose expression is temporally correlated with acquisition of one or more structural and/or functional features by a cell. For example, expression of the TM may increase as the cell acquires or begins to exhibit or possess the structural and/or functional feature(s) and/or expression of the TM may decrease as the cell ceases to exhibit or possess the feature(s) (or vice versa). The TM may be one whose expression is normally required in order for a cell to undergo a change in cell state or type (e.g., to differentiate from a progenitor cell to a mature, fully differentiated cell). For example, in the absence of the TM the cell would not naturally undergo the change in cell state or type (although in some embodiments the cell may undergo such change either as a result of disease or as a result of intervention by man), or if expression of the TM is inhibited in a cell that expresses it, the cell may lose one or more structural and/or functional characteristics of the cell's type or state.

In some embodiments, a TM, e.g., a TF, is one that occupies one or more active genes in a cell type of interest and/or in a cell state of interest, optionally together with a second transcriptional modulator, e.g., a positive elongation factor, e.g., P-TEFB. In some embodiments, a TM is one that occupies multiple active genes in a cell type and/or cell state of interest. In some embodiments, a TM is one that occupies one or more active genes in a cell of a first cell type and does not occupy one or more of those genes in a cell of a second cell type. In some embodiments, a TM is one that occupies one or more active genes in a cell in a first cell state and does not occupy one or more of those genes in a cell in a second cell state. The difference in occupancy of such gene(s) by the TM may be at least in part responsible for the difference in cell state or cell type. In some aspects of the invention, modulating the TM is of use to modify cell type, e.g., to alter a cell of a first type so that it more closely resembles the second cell type or alters sufficiently that it would be considered to be a cell of the second cell type. In some aspects of the invention, modulating the TM is of use to modify cell state, e.g., to alter the state of cell state in a first cell state to a second cell state. In some embodiments, the TM is one that recruits a positive elongation factor, e.g., p-TEFb, to the region of a transcription start site, e.g., to a promoter-proximal region, of a gene. The TM may thus promote a transition in the gene from nonproductive to active transcription. In some embodiments of the invention, cell type and/or cell state is modulated at least in part by causing nonproductive genes to become active and/or by causing active genes to become nonproductive, e.g., by inhibiting pause release in a cell.

Certain aspects of the invention relate to the identification and/or modulation of TMs that differentially occupy active genes (e.g., the promoter-proximal region thereof) in two or more different cell types. Certain aspects of the invention relate to the identification and/or modulation of TMs that differentially occupy genes (e.g., the promoter-proximal region thereof) in two or more different cell states. In other words, at least some genes occupied by the TM in the first cell type or cell state are not occupied by the TM in the second cell type or cell state and/or at least some genes occupied by the TM in the second cell type or cell state are not occupied by the TM in the first cell type or cell state. In some embodiments of the invention, the difference in occupancy by the TM is at least in part responsible for the difference in cell type or cell state. In some embodiments, the genes are active if occupied by the TM and nonproductive if not occupied by the TM. In some embodiments, modifiers (e.g., activators or inhibitors) of the TM can alter the activity of the genes (e.g., by causing occupied genes to change from active to nonproductive or to change from nonproductive to active, or causing unoccupied genes to change from nonproductive to active). For example, in some embodiments, inhibiting a TM that occupies an active gene renders such gene nonproductive. In some embodiments, activating a TM that does not occupy a nonproductive gene causes the TM to occupy the gene and renders the gene active or increases the activity of a TM at an occupied gene and thereby causes the gene to become more active.

Active genes may be distinguished from, e.g., nonproductive genes (genes that show evidence of initiation but are not productively transcribed because, e.g., RNA polymerase is paused such that elongation does not occur) or inactive genes (in which initiation has not occurred). Active genes may be distinguished, for example, by the presence of nucleosomes containing histones H3K4me3 (initiation-associated chromatin modification) and/or H3K79me2 (elongation-associated chromatin modification) (or other suitable chromatin modifications associated with initiation and/or elongation) as markers of transcriptional state. In some embodiments, active genes have both H3K4me3 and H3K79me2 chromatin modifications, nonproductive genes have only H3K4me3, and inactive genes do not have H3K4me3 or H3K79me2.

A TM may be considered to "occupy" a gene if it is bound directly or indirectly to DNA located within about 1000 base pairs upstream of or downstream from a transcriptional start site of the gene. In some embodiments, binding of a TM is enriched between −1000 bp and about 1000 bp of a transcriptional start site of one or more active genes (as compared with average binding elsewhere in the genome). In some embodiments, binding of a TM is enriched within a promoter-proximal region, e.g., between from about 30 bp to about +300 bp from the transcriptional start site of a gene. Binding of a TM to DNA may be assessed, e.g., using Chip-ChIP or Chip-SEQ (see Examples). In some embodiments, enriched binding refers to binding at least 5, or in some embodiments at least 10-fold, as great as average binding outside a region of interest. The binding may be enriched mainly within a portion of a particular region. In some embodiments, a distinct binding peak may be readily observed (see, e.g., FIG. 13B). In some embodiments, the invention relates to identifying TMs that co-occupy one or more gene(s), e.g., active gene(s). In some embodiments, the invention relates to identifying TMs that co-occupy genes with a positive elongation factor, e.g., P-TEFB. In some embodiments, such TMs are modulated, optionally in combination with modulating the positive elongation factor.

In some aspects, the invention relates to TMs that modulate expression of one or more target gene(s), wherein the target gene(s) are active when occupied by the TM and are nonproductive or inactive when not occupied by the TM. In some embodiments of interest, the gene(s) are nonproductive when not occupied by the TM. In some embodiments, the TM binds to target gene DNA and recruits a pause release factor, e.g., a positive elongation factor (e.g., p-TEFB or a different positive elongation factor), to the gene, thereby allowing the target gene to transition from nonproductive to active. In some embodiments, a cell is in a first cell state when the TM is occupying the target gene(s) (and the target gene(s) are active), whereas the cell is in a second cell state when the TM is not occupying the target gene(s) (and the target gene(s) are not active, e.g., they are nonproductive). In some embodiments, a cell is of a first cell type when the TM is occupying the target gene(s) (and the target gene(s) are active), whereas the cell is not of the first cell type when the TM is not occupying the target gene(s) (and the target gene(s) are not active, e.g., they are nonproductive). The cell may exhibit a modified cell type that may or may not be highly similar or essentially indistinguishable from a second cell type (e.g., based on appearance, marker expression, response to a stimulus, etc.).

The first and second cell types or cell states could be any cell type or cell state known in the art. In some embodiments of, a first cell state is a disease-associated state, and a second cell state is a healthy state, and the method comprises modulating a TM whose inhibition or activation modifies the state of cells of the first cell state to more closely resemble the second cell state or to fully assume the second cell state. In some embodiments a first cell type is a disease-associated cell type, and the second cell type is a cell type that is not associated with disease or is more amenable to treatment than the first cell type, and the method is used to identify a TM whose inhibition or activation modifies the cells of the first cell type to more closely resemble cells of the second cell type or to become highly similar to or be fully converted into the second cell type (i.e., become essentially indistinguishable from cells of the second cell type.

In some aspects, the invention provides a method of identifying a TM that is a candidate modifier of cell state, the method comprising: (a) identifying a set of genes that is active in cells in a first cell state and nonproductive in cells of a second cell state; and (b) identifying a TM that occupies at least some of said genes in the first cell state but not in the second cell state, thereby identifying a TM that is a candidate modifier of cell state. In some aspects, the invention provides a method of identifying a TM that is a candidate modifier of cell type, comprising: (a) identifying a set of genes that is active in cells of a first cell type and not active (e.g., nonproductive) in cells of a second cell type; and (b) identifying a TM that occupies at least some of said genes in the first cell type but not in the second cell type, thereby identifying a TM that is a candidate modifier of cell type. In some embodiments, the method comprises selecting first and second cell types or cell states of interest prior to performing step (a) of the method. In some embodiments, the method comprises obtaining cells of first and second cell types or cell states of interest prior to performing step (a) of the method. For example, cells in first and second cell states can be obtained directly from a subject or cells in either or both state(s) can be generated in vitro. In some embodiments, for example, cells are activated in vitro by exposing them to a stimulus. In some embodiments, steps (a), (b), or both, can be performed at least in part using data obtained from the literature or from public databases. In some embodiments, the steps are performed using techniques described herein. In one aspect, a genome-wide NF-kB regulatory network map is available for human monocytic cells responding to bacterial lipopolysaccharide (LPS) (Schreiber, J., et al., Proc Natl Acad Sci USA, 103(15): 5899-904, 2006. In some aspects, a method further comprises (c) inhibiting the TM in a cell in which it is expressed (e.g., using .RNA interference) or expressing the TM in a cell in which it is not otherwise expressed; and (d) determining whether the inhibition or expression of the TM modifies cell type and/or cell state, wherein if the inhibition or expression of the TM modifies cell state or cell type, then the TM is confirmed as a modifier of cell state or cell type, respectively. If the inhibition or expression of the TM modifies cell state and cell type, the TM is a modifier of both cell state and cell type.

The discovery of the role of c-Myc in mediating pause release and transcriptional regulation of a large and heretofore unappreciated number of genes has broad implications with respect to the ability to manipulate cell state through modifying c-Myc function, e.g., using pharmacological approaches. In some aspects, the invention relates to combined modulation of transcriptional modulators, wherein at least one of the transcriptional modulators is c-Myc. In some aspects, the invention relates to combined modulation of transcriptional modulators, wherein at least one of the transcriptional modulators is p-TEFb. The invention relates, in certain aspects, to a method of modifying cell state comprising contacting a cell with a c-Myc modifier and a modifier of a second transcriptional modulator. In some embodiments, the second transcriptional modulator is a transcription factor (TF), e.g., a transcription factor that binds to DNA (optionally in a complex such as a homodimer, heterodimer, or oligomer with one or more other proteins) and typically in a sequence-specific manner. In some embodiments, the second transcriptional modulator is an initiation or elongation factor. In some embodiments, the second transcriptional modulator is a cell-type specific modulator (e.g., expressed selectively in a subset of cell lineages, e.g., neural, hematopoietic, to name but a few). In some embodiments, the second transcriptional modulator is a co-activator. In some embodiments, the second transcriptional modulator is one that is regulated by a signaling pathway. As noted above, a TF could be, e.g., a helix-loop-helix, helix-turn-helix, winged helix, leucine zipper, bZIP, zinc finger, or homeodomain protein. In some embodiments, transcriptional modulators are, e.g., TCF family members or Smad family members. In some embodiments, a exemplary signaling pathway is the Wnt signaling pathway or the TGFb signaling pathway. A "modifier", e.g., of c-Myc, NF-kB, or of a second transcriptional modulator, can be, e.g., an inhibitor or an activator, or a compound that in any way alters the activity or activity of c-Myc, NF-kB, or the second transcriptional modulator, respectively. In some embodiments, the cell state that is modified is proliferation state. In some embodiments, the method is of use to treat, e.g., a metabolic, neurodegenerative, inflammatory, auto-immune, proliferative, infectious, cardiovascular, musculoskeletal, or other disease.

In some aspects the invention provides the invention provides a method of modifying cell type, comprising contacting a cell with a c-Myc modifier and a modifier of a second transcriptional modulator. In some aspects the invention provides the invention provides a method of modifying cell type, comprising contacting a cell with an NF-kB modifier and a modifier of a second transcriptional modulator.

The invention relates at least in part to combined inhibition of P-TEFb and c-Myc and uses thereof. In one aspect, the invention provides a method comprising contacting a cell with effective amounts of a P-TEFb inhibitor and a c-Myc inhibitor. In some embodiments, the invention provides a method of inhibiting proliferation or survival of a cell comprising contacting the cell with effective amounts of a P-TEFb inhibitor and a c-Myc inhibitor. The invention further provides a variety of compositions comprising a P-TEFb inhibitor and a c-Myc inhibitor. In some embodiments the composition is a pharmaceutical composition. The P-TEFb inhibitor can be any P-TEFb inhibitor. The c-Myc inhibitor can be any c-Myc inhibitor. In another aspect, the invention provides a method comprising contacting a cell with effective amounts of a P-TEFb inhibitor and an NF-kappa B (NF-kB) inhibitor. In some embodiments, the invention provides a method of inhibiting proliferation or survival of a cell comprising contacting the cell with effective amounts of a P-TEFb inhibitor and an NF-kB inhibitor. The invention further provides a variety of compositions comprising a P-TEFb inhibitor and an NF-kB inhibitor. In some embodiments the composition is a pharmaceutical composition. The P-TEFb inhibitor can be any P-TEFb inhibitor. The NF-kB inhibitor can be any NF-kB inhibitor. All combinations are encompassed and can be applied in various aspects of the invention. While the invention is described herein mainly in reference to P-TEFb inhibition in combination with c-Myc inhibition and/or in reference to P-TEFb inhibition in combination with NF-kB inhibition, other means of inhibiting pause release are within the scope of the invention. For example, a compound that enhances expression or activity of a protein that promotes pausing, such as NELF, could be used and such compositions and methods are within the scope of the invention.

As used herein, "P-TEFb inhibitor" refers to a compound that inhibits (reduces, decreases) the activity and/or expression of P-TEFb. P-TEFb exists within cells both as a kinase-active free form and a larger, kinase-inactive form that contains 7Sk RNA and hexamethylene bisacetamide-induced protein 1 (HEXIM1) or HEXIM2 and may serve as a reservoir for the active form. Unless otherwise indicated, the term "P-TEFb" refers to the active form. "Activity of P-TEFb" can refer to kinase activity of P-TEFb against a substrate, e.g., the Pol II CTD "Inhibit the activity of P-TEFb" encompasses inhibiting kinase activity of a functional P-TEFb complex or inhibiting formation or maintenance of a stable and/or functional P-TEFb complex. In some embodiments, an activity of p-TEFb is binding to c-Myc. "Inhibiting expression of P-TEFb" encompasses inhibiting expression of CDK9 and/or inhibiting expression of a P-TEFb cyclin subunit, resulting in decrease in the amount of functional P-TEFb relative to the amount that would be present in the absence of the inhibitor. As used herein, a "c-Myc inhibitor" refers to a compound that inhibits (reduces, decreases) the activity and/or expression of c-Myc. In some aspects, "activity of c-Myc" refers to ability of c-Myc (typically in a complex with Max) to bind to DNA and activate transcription Inhibiting c-Myc activity can encompass inhibiting formation or maintenance of c-Myc/Max dimers, inhibiting ability of c-Myc/Max dimers to bind to target sites in DNA, and/or inhibiting ability of c-Myc/Max dimers to activate transcription. In some embodiments, an activity of c-Myc is binding to p-TEFb. As used herein, an "NF-kB inhibitor" refers to a compound that inhibits (reduces, decreases) the activity and/or expression of NF-kB. In some aspects, "activity of NF-kB" refers to ability of NF-kb to bind to DNA and activate transcription, e.g., at least in part by recruiting one or more co-activators Inhibiting NF-kb activity can encompass inhibiting formation or maintenance of NF-kB dimers, inhibiting ability of NF-kb dimers to bind to target sites in DNA, inhibiting ability of NF-kb dimers to recruit one or more co-activators, and/or inhibiting ability of NF-kB to activate transcription. In some embodiments, an activity of NF-kB is binding to p-TEFb.

Abnormal or unwanted cell proliferation or survival plays a role in a variety of diseases and disorders (collectively referred to herein as "proliferative diseases"). Methods and compositions of the invention can be used in the treatment of such diseases. The invention provides a method of treating a proliferative disease in a subject in need thereof comprising administering therapeutically effective amounts of a P-TEFb inhibitor and a c-Myc inhibitor to the subject. The invention further provides a method of treating a proliferative disease in a subject in need thereof comprising administering therapeutically effective amounts of a P-TEFb inhibitor and an NF-kB inhibitor to the subject.

Any of a wide variety of agents (also termed "compounds") can be used in the inventive methods as inhibitors, e.g., as P-TEFb inhibitors or c-Myc inhibitors or NF-kB inhibitors. An inhibitor could be any compound that, when contacted with a cell, results in decreased functional activity of a molecule or complex, e.g., P-TEFb or c-Myc or NF-kB, in the cell. An inhibitor could act directly, e.g., by physically interacting with a molecule or complex to be inhibited, or a component thereof, or indirectly such as by interacting with a different molecule or complex required for activity of the molecule or complex to be inhibited, or by interfering with expression or localization. For example, inhibitors of NF-kB frequently act on kinases or other proteins that play a role in post-translational modifications such as phosphorylation, sumoylation, ubiquitylation, and acetylation that can affect the localization, stability and/or binding activity of NF-kB proteins. In some embodiments, an NF-kB inhibitor is at least somewhat specific to one or more forms of NF-kB.

Compounds of use in various embodiments of the invention can comprise, e.g., small molecules, peptides, polypeptides, nucleic acids, oligonucleotides, etc. Certain non-limiting examples are presented below.

A small molecule is often an organic compound having a molecular weight equal to or less than 2.0 kD, e.g., equal to or less than 1.5 kD, e.g., equal to or less than 1 kD, e.g., equal to or less than 500 daltons and usually multiple carbon-carbon bonds. Small molecules often comprise one or more functional groups that mediate structural interactions with proteins, e.g., hydrogen bonding, and typically include at least an amine, carbonyl, hydroxyl or carboxyl group, and in some embodiments at least two of the functional chemical groups. A small molecule may comprise cyclic carbon or heterocyclic structures and/or aromatic or polyaromatic structures substituted with one or more chemical functional groups and/or heteroatoms. In some embodiments a small molecule satisfies at least 3, 4, or all criteria of Lipinski's "Rule of Five". In some embodiments, a compound is cell-permeable, e.g., within the range of typical compounds that act intracellularly, e.g., within mammalian cells. In some embodiments, the IC50 of a compound, e.g., a small molecule, for a target to be inhibited is less than or equal to about 5 nM, 10 nM, 50 nM, 100 nM, 500 nM, 1 µM, 10 µM, 50 µM, or 100 µM.

Nucleic acids, e.g., oligonucleotides (which typically refers to short nucleic acids, e.g., 50 nucleotides in length or less), the invention contemplates use of oligonucleotides that are single-stranded, double-stranded (ds), blunt-ended, or double-stranded with overhangs, in various embodiments of the invention. The full spectrum of modifications (e.g., nucleoside and/or backbone modifications), non-standard nucleotides, delivery vehicles and systems, etc., known in the art as being useful in the context of siRNA or antisense-based molecules for research or therapeutic purposes is contemplated for use in various embodiments of the instant invention. In some embodiments a compound is an RNAi agent, antisense oligonucleotide, or aptamer. The term "RNAi agent" encompasses nucleic acids that can be used to achieve RNA silencing in mammalian cells. As used herein RNA silencing, also termed RNA interference (RNAi), encompasses processes in which sequence-specific silencing of gene expression is effected by an RNA-induced silencing complex (RISC) that has a short RNA strand incorporated therein, which strand directs or "guides" sequence-specific degradation or translational repression of mRNA to which it has complementarity. The complementarity between the short RNA and mRNA need not be perfect (100%) but need only be sufficient to result in inhibition of gene expression. For example, the degree of complementarity and/or the characteristics of the structure formed by hybridization of the mRNA and the short RNA strand can be such that the strand can (i) guide cleavage of the mRNA in the RNA-induced silencing complex (RISC) and/or (ii) cause translational repression of the mRNA by RISC. The short RNA is often incorporated into RISC as part of a short double-stranded RNA (dsRNA). RNAi may be achieved artificially in eukaryotic, e.g., mammalian, cells in a variety of ways. For example, RNAi may be achieved by introducing an appropriate short double-stranded nucleic acid into the cells or expressing in the cells a nucleic acid that is processed intracellularly to yield such short dsRNA. Exemplary RNAi agents are a short hairpin RNA (shRNA), a short interfering RNA (siRNA), micrRNA (miRNA) and a miRNA precursor. siRNAs typically comprise two separate nucleic acid strands that are hybridized to each other to form a duplex. They can be synthesized in vitro, e.g., using standard nucleic acid synthesis techniques. A nucleic acid may contain one or more non-standard nucleotides, modified nucleosides (e.g., having modified bases and/or sugars) or nucleotide analogs, and/or have a modified backbone. Any modification or analog recognized in the art as being useful for RNAi, aptamers, antisense molecules or other uses of oligonucleotides can be used. Some modifications result in increased stability, cell uptake, potency, etc. Exemplary compound can comprise morpholinos or locked nucleic acids. In some embodiments the nucleic acid differs from standard RNA or DNA by having partial or complete 2'-O-methylation or 2'-O-methoxyethyl modification of sugar, phosphorothioate backbone, and/or a cholesterol-moiety at the 3'-end. In certain embodiments the siRNA or shRNA comprises a duplex about 19 nucleotides in length, wherein one or both strands has a 3' overhang of 1-5 nucleotides in length (e.g., 2 nucleotides), which may be composed of deoxyribonucleotides. shRNA comprise a single nucleic acid strand that contains two complementary portions separated by a predominantly non-self-complementary region. The complementary portions hybridize to form a duplex structure and the non-self-complementary region forms a loop connecting the 3' end of one strand of the duplex and the 5' end of the other strand. shRNAs can undergo intracellular processing to generate siRNAs. In certain embodiments the term "RNAi agent" also encompasses vectors, e.g., expression vectors, that comprise templates for transcription of an siRNA (e.g., as two separate strands that can hybridize), shRNA, or microRNA precursor, and can be used to introduce such template into mammalian cells and result in transient or stable expression thereof.

In some embodiments an RNAi agent, aptamer, antisense oligonucleotide, other nucleic acid, peptide, polypeptide, or small molecule is physically associated with a moiety that increases cell uptake, such as a cell-penetrating peptide, or a delivery agent. In some embodiments a delivery agent at least in part protects the compound from degradation, metabolism, or elimination from the body (e.g., increases the half-life). A variety of compositions and methods can be used to deliver agents to cells in vitro or in vivo. For example, compounds can be attached to a polyalkylene oxide, e.g., polyethylene glycol (PEG) or a derivative thereof, or incorporated into or attached to various types of molecules or particles such as liposomes, lipoplexes, or polymer-based particles, e.g., microparticles or nanoparticles composed at least in part of one or more biocompatible polymers or co-polymers comprising poly(lactide-glycolide), copolyoxalates, polycaprolactones, polyesteramides, polyorthoesters. polyhydroxybutyric acid, and/or polyanhydrides.

In some embodiments, a compound comprises a polypeptide. A polypeptide can be a dominant negative version of a P-TEFb subunit or a dominant negative version of c-Myc or Max or a dominant negative version of an NF-kB protein. A polypeptide that binds to and inhibits P-TEFb or c-Myc or NF-kB could be identified, e.g., using phage display. Polypeptides may contain any of the 20 amino acids that are naturally found in proteins and are genetically encoded ("standard" amino acids), other amino acids that are found in nature, and/or artificial amino acids or amino acid analogs. One or more of the amino acids in a polypeptide may be modified, for example, by the addition of a chemical entity such as a carbohydrate group, a phosphate group, a fatty acid group, an alkyl group etc.

In some embodiments a compound comprises an antibody. The term "antibody" encompasses immunoglobulins and derivatives thereof containing an immunoglobulin domain capable of binding to an antigen. An antibody can originate from any mammalian or avian species, e.g., human, rodent (e.g., mouse, rabbit), goat, chicken, etc., or can be generated using, e.g., phage display. The antibody may be a member of any immunoglobulin class, e.g., IgG, IgM, IgA, IgD, IgE, or subclasses thereof such as IgG1, IgG2, etc. In various embodiments of the invention "antibody" refers to an antibody fragment such as an Fab', F(ab')2, scFv (single-chain variable) or other fragment that retains an antigen binding site, or a recombinantly produced scFv fragment, including recombinantly produced fragments. An antibody can be monovalent, bivalent or multivalent in various embodiments. The antibody may be a chimeric or "humanized" antibody, which can be generated using methods known in the art. An antibody may be polyclonal or monoclonal, though monoclonal antibodies may be preferred. Methods for producing antibodies that specifically bind to virtually any molecule of interest are known in the art. In some aspects the antibody is an intrabody, which may be expressed intracellularly. In some embodiments a compound comprises a single-chain antibody and a protein transduction domain (e.g., as a fusion polypeptide).

In some embodiments, a composition or method of the invention employs a P-TEFb inhibitor and a c-Myc inhibitor that are small molecules. In some embodiments, a composition or method employs a P-TEFb inhibitor and a c-Myc inhibitor that each comprise a nucleic acid, e.g., RNAi agents.

In some embodiments, a composition or method of the invention employs a P-TEFb inhibitor and an NF-kB inhibitor that are small molecules. In some embodiments, a composition or method employs a P-TEFb inhibitor and an NF-kB inhibitor that each comprise a nucleic acid, e.g., RNAi agents, e.g., siRNAs.

Compounds can be produced using any suitable method known in the art. The skilled artisan will select an appropriate method based, e.g., on the nature of the compound. The production method can be partially or completely synthetic in various embodiments. In some embodiments a compound (or starting material for synthesis) is purified from an organism or other natural source, e.g., a plant, microbe, fermentation broth, etc. A compound of use in the invention may be provided as part of a composition, which may contain, e.g., an ion, salt, aqueous or non-aqueous diluent or carrier, buffer, preservative, etc. It is noted that although combined use of compounds is of particular interest, the use of compounds disclosed herein is not limited to their use in combination. In some embodiments of the invention, a compound may be used as a single agent.

II. P-TEFb Inhibitors

In some embodiments, a P-TEFb inhibitor inhibits CDK9 kinase activity. The compound may inhibit one or more additional kinases, e.g., CDKs, in addition to CDK9. Often a kinase inhibitor acts by binding to an ATP binding pocket of a kinase. Thus in some embodiments a CDK9 inhibitor binds to the ATP binding pocket of CDK9. In some embodiments the P-TEFb inhibitor is selective for CDKs relative to many, most, or all other kinase families. In some embodiments the CDK inhibitor is selective for CDKs 1, 4, and 9 versus CDK2. In some embodiments the P-TEFb inhibitor is a CDK inhibitor that is selective for CDK9 versus CDK2. In some embodiments the P-TEFb inhibitor is a CDK inhibitor that is selective for CDK9 versus CDK1 and CDK4. It will be appreciated that kinase inhibitory activity is tested against CKDs in complex with a preferred cyclin partner. For example, in some embodiments CDK2 activity can be tested using cyclin A. It will also be appreciated that a kinase assay can employ a relevant substrate, e.g., a physiologically relevant substrate or portion thereof comprising a phosphoryation site for the kinase.

In some embodiments, the compound is an N-methylpiperidinyl, chlorophenyl flavone. In some embodiments, the compound is flavopiridol or a flavopiridol analog. Flavopiridol (−)-2-(2-Chlorophenyl)-5,7-dihydroxy-8-[(3S,4R)-3-hydroxy-1-methyl-4-piperidinyl]-4H-1-benzopyran-4-one hydrochloride is a synthetic flavone that inhibits multiple CDKs, including CDK9. Its structure is shown below.

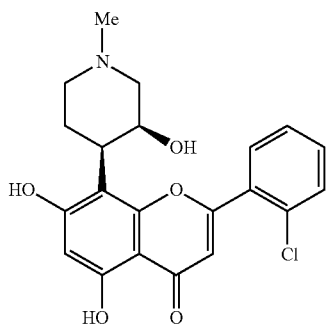 [SMILES: CN1CC[C@H](c2c(O)cc(O)c3c(=O)cc(-c4ccccc4Cl)oc23)[C@H](O)C1]

Flavopiridol has been shown to have antitumor activity against various tumor cells lines and to inhibit tumor growth in xenograft models. It has undergone clinical trials in a number of different cancer types including various solid tumors and leukemias. As described further in the examples, flavopiridol was shown to inhibit pause release. Without wishing to be bound by theory, this may help counteract the effects of Myc overexpression, and this may be the basis for the therapeutic effect of flavopiridol on some tumors.

Flavopiridol analogs include compounds designed based on flavopiridol, e.g., by modifying one or more of the rings of the flavopiridol structure at one or more positions. In some embodiments, a flavopiridol analog is a 2-thio or 2-oxo flavopiridol analog. For example, PCT/US1997/007610 describes compounds of formula I:

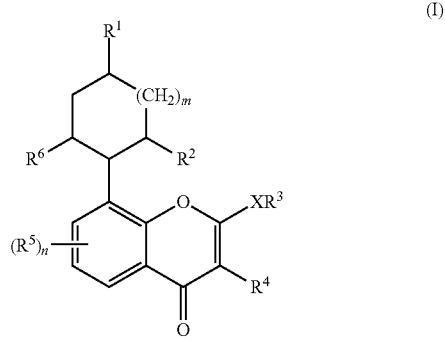

wherein X is oxygen or sulfur; $R^1$, $R^2$, $R^3$, $R^4$, $R^5$, $R^6$, m, and n are as defined in PCT/US1997/007610.

Additional flavopiridol analogs are disclosed in Murthi, K. K., et al., Bioorg Med Chem Lett. 10(10):1037-41, 2000, which describes modifications of the 3-hydroxy-1-methylpiperidinyl (D ring) of flavopiridol.

In some embodiments, a flavopiridol analog has the following structure:

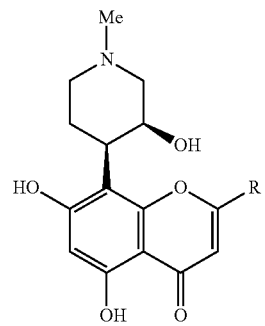

In some embodiments R is phenyl or substituted phenyl, e.g., halogenated phenyl. In some embodiments, R is selected from the group consisting of: 3-chlorophenyl, 4-chlorophenyl, 2-fluorophenyl, 4-fluorophenyl, 4-bromophenyl, 4-t-butylphenyl, 4-trifluoromethylphenyl, 4-hydroxyphenyl, 2-pyridyl, 3-pyridyl, 4-pyridyl, 4-chloro-3-pyridyl, 5-methylisoxazole, 3-vinylphenyl, 4-vinylphenyl, 2-chlorophenyl, 4-fluorophenyl, 2-bromophenyl, and 3-pyridyl. In some embodiments the compound displays increased selectivity for CDK9 than does flavopiridol. See, e.g., Ali, A., et al., Chembiochem, 10(12):2072-80, 2009, for additional information regarding these compound.

In some embodiments, a CDK9 inhibitor has the following structure:

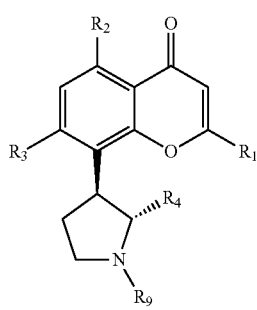

wherein R1, R2, R3, R4, and R9 are as defined in PCT/IB2006/052002 (WO/2007/148158). In some embodiments (i) R1 comprises an aromatic group; (ii) R4 comprises an R—(OH) group, wherein R is a $C_{1-6}$ aliphatic group; (iii) R9 comprises a $C_{1-6}$ aliphatic group, e.g, a methyl group; or (iv) any combination of (i), (ii), and (iii). In some embodiments, the compound may have the following structure:

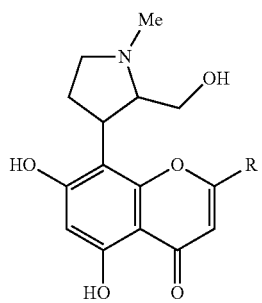

wherein R comprises an aromatic group.

Crystal structures of P-TEFb (CDK9/cyclin T1) alone and in a complex with flavopiridol are available (Baumli, S., et al., EMBO J. 27(13):1907-18, 2008). Flavopiridol was shown to bind to the ATP binding pocket of CDK9. Structural information can be used in the design of additional P-TEFb inhibitors including, but not limited to, additional analogs of flavopiridol. Furthermore, virtual screening can be performed using structural information regarding diverse chemical compounds to identify candidate P-TEFb inhibitors. In some embodiments, a P-TEFb inhibitor is a compound that makes similar intermolecular contacts with CDK9 as does flavopiridol. Similar approaches can be used to design analogs of other CDK9 inhibitors.

In some embodiments, a flavopiridol analog exhibiting reduced binding to human serum relative to flavopiridol is used.

In some embodiments, the P-TEFb inhibitor is a purine or purine analog, e.g., a biaryl purine analog. In some embodiments, the purine analog is a 2,6,9-substituted purine analog. In some embodiments, the compound is roscovitine, e.g., S-roscovitine or R-roscovitine. Unless otherwise indicated, where roscovitine is mentioned herein, the roscovitine can be R-roscovitine (also called Seliciclib or CYC202; 2-(R)-(1-Ethyl-2-hydroxyethylamino)-6-benzylamino-9-isopropyl purine). Roscovitine is a CDK inhibitor that preferentially inhibit multiple enzyme targets including CDK1, CDK2, CDK7 and CDK9 and has been studied in clinical trials for treatment of a variety of proliferative diseases.

In some embodiments the compound is a roscovatine analog. Exemplary roscovitine analogs are oloumicine (2-(2-hydroxyethylamino)-6-benzylamino-9-methylpurine), olomoucine II (6-[(2-hydroxybenzyl)amino]-2-[[1-(hydroxymethyl)propyl]amino]-9-isopropylpurine) and LGR1406 (N-5-(2-aminocyclohexyl)-N-7-benzyl-3-isopropyl-1(2) H-pyrazolo[4,3-d]pyrimidine-5,7-di-amine). Roscovitine analogs generated by introduction of an aryl ring onto the 4-position of the C-6 benzyl amino group of roscovitine, and a series of C-6 biarylmethylamino derivatives prepared with modifications on the C-6 biaryl rings, N-9 and C-2 positions, are described in Trova, M P, et. al., Bioorg Med Chem Lett. 19(23):6608-12, 2009.

Many additional CDK inhibitors are known in the art that may inhibit CDK9, optionally with at least some selectivity relative to inhibition of one or more other CDKs. For example, PCT/US2009/049637 (WO/2010/003133) discloses compounds that are reported to inhibit CDK9. In some aspects, the compounds have the following structure, where R1 and R3 are as defined therein.

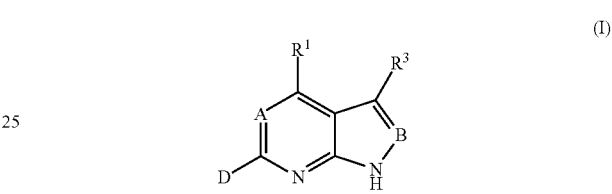

PCT/EP2008/063715 (WO 2009047359) discloses additional compounds that are reported to inhibit CDK9. In some aspects, the compounds have the following structure, wherein R1, R2, Ra, and $(R3)_x$ are as defined therein.

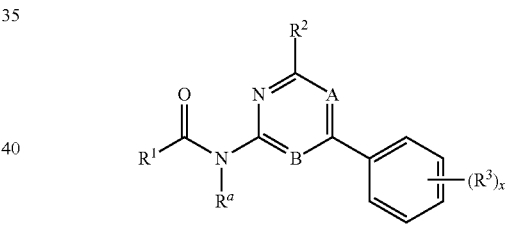

In some embodiments, a P-TEFb inhibitor comprises an RNAi agent (e.g., an siRNA) or an antisense oligonucleotide that inhibits expression of a P-TEFb subunit (e.g., CDK9, cyclin T1, T2a, T2b, or K). In some embodiments a P-TEFb inhibitor comprises an antibody or aptamer that specifically binds to a P-TEFb subunit. Optionally the antibody or aptamer may bind to multiple CDKs or cyclins.

III. c-Myc Inhibitors

In some embodiments, a c-Myc inhibitor is a small molecule. In some embodiments, a c-Myc inhibitor inhibits formation of c-Myc/Max heterodimers. In some embodiments, a c-Myc inhibitor inhibits binding of c-Myc/Max to a target site in DNA. In some embodiments a c-Myc inhibitor is relatively specific for inhibiting transcription mediated by c-Myc relative to transcription mediated by many or most other basic helix-loop-helix/leucine zipper transcription factors.

Various compounds that inhibit c-Myc are described in Berg, T., Curr. Op. Chem. Biol., 12: 464-471, 2008, and references therein. The peptide mimetic IIA6B17 is described in Berg, T., et al., Proc Natl Acad Sci USA 99 (2002), pp. 3830-3835 and was shown to inhibit c-Myc-dependent transcription in a reporter gene assay (X. Lu, et al. Oncol Rep 19 (2008), pp. 825-830.). Testing a 285 member chemical library derived from planar, aromatic scaffolds in a c-Myc/Max dimerization assay led to identification of four structurally related Myc/Max dimerization inhibitors, which also inhibited DNA binding of c-Myc/Max (Y. Xu, et al. *Bioorg Med Chem* 14 (2006), pp. 2660-2673.) For example, the compound NY2267 strongly inhibited c-Myc-dependent oncogenic transformation of chicken embryo fibroblasts at 20 µM, showed selectivity over transformation mediated by v-Src or v-Jun, but did not discriminate between transcription mediated by c-Jun and c-Myc. Several compounds were selected from a chemical library on the basis of their ability to prevent association of the HLH-Zip domains of c-Myc and Max in a yeast two-hybrid assay (X. Yin, et al., Oncogene 22 (2003), pp. 6151-6159.). One, 10058-F4 ($IC_{50}$=49 µM on HL60 cells), served as starting point for the testing of derivatives with improved activities. One of the numerous derivatives resulting from structural variation of the substituents on the aromatic ring and the rhodanine moiety, the compound 28RH-NCN-1, inhibited DNA binding of c-Myc with activity comparable to that of the parent compound, and inhibited growth of HL60 cells with improved potency ($IC_{50}$=29 µM) (Wang, H., et al., *Mol Cancer Ther* 6 (2007), pp. 2399-2408). See also PCT/US2007/004039 (WO/2007/098010). Screening chemical libraries for compounds that inhibited DNA binding of c-Myc, led to discovery of the pyrazolo[1,5-a]pyrimidine Mycro1 (Kiessling, A., et al., *Chem Biol* 13 (2006), pp. 745-751.). Mycro1 and the derivative Mycro2 were subsequently shown to inhibit c-Myc/Max dimerization, c-Myc-dependent proliferation, gene transcription, and oncogenic transformation. While Mycro1 and Mycro2 displayed good specificities in vitro, they showed only weak-to-moderate specificity for c-Myc-dependent transcription over transcription mediated by AP-1 family proteins, which also dimerize via leucine zippers. A follow-up screen using a focused library of pyrazolo[1,5-α]pyrimidines led to the discovery of the pyrazolo[1,5-α]pyrimidine 1 (Mycro3), which inhibited c-Myc/Max dimerization and DNA binding with very good selectivity in vitro, and also showed good potency and selectivity at concentrations of 10-40 µM against c-Myc in cellular assays (A. Kiessling, A, et al., *Chem Med Chem* 2 (2007), pp. 627-630.).

It can be reasoned that inhibitors of the DNA—protein interactions between intact c-Myc/Max dimers and their DNA recognition motif should not interfere with gene transcription repressed by c-Myc, but would still block c-Myc induced transcriptional activation. This distinction can be used to help selectively identify compounds having this mechanism of action. In a screen designed to identify compounds that particularly affect cells with high levels of c-Myc, a compound termed MYRA-A, was discovered, which was shown to inhibit Myc-regulated gene expression, oncogenic transformation, and to induce apoptosis in a Myc-dependent manner (H. Mo and M. Henriksson, *Proc Natl Acad Sci U S A* 103 (2006), pp. 6344-6349.). In a subsequent study, the same group published an additional inhibitor of DNA binding of c-Myc/Max family members dubbed NSC308848 (Mo, H., et al. *Cell Cycle* 5 (2006), pp. 2191-2194.).

Hammoudeh, et al. (2009) identified multiple small molecule binding sites on c-Myc, facilitating use of drug design and/or virtual screening to identify additional c-Myc inhibitors.

Some exemplary small molecule c-Myc inhibitors of use in various embodiments of the invention are shown below. In certain embodiments of the invention analogs of any of these compounds are used.

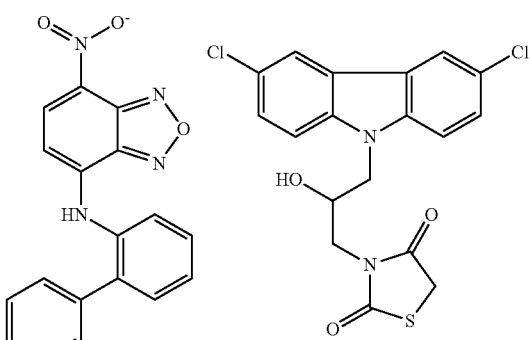

10074-G5

10074-A4

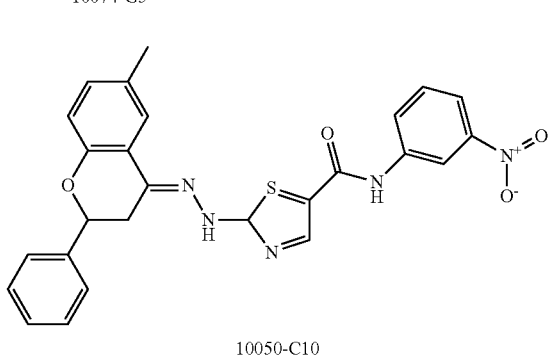

10050-C10

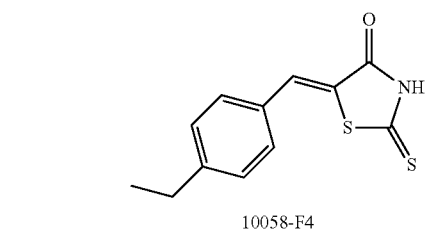

10058-F4

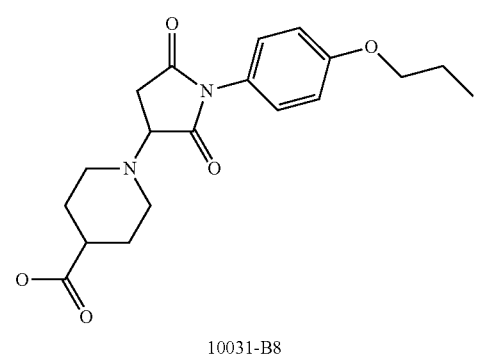

10031-B8

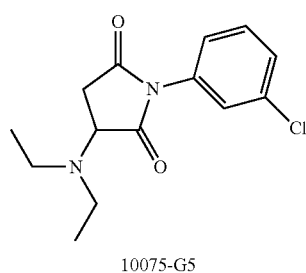

10075-G5

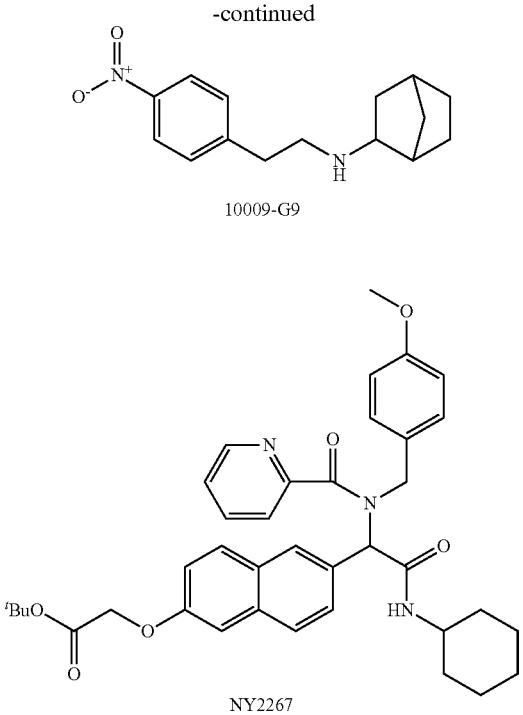
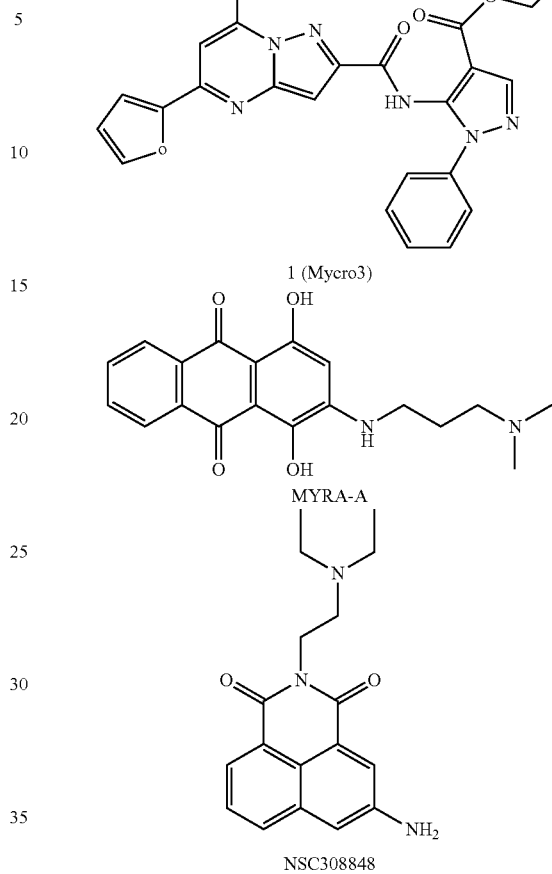
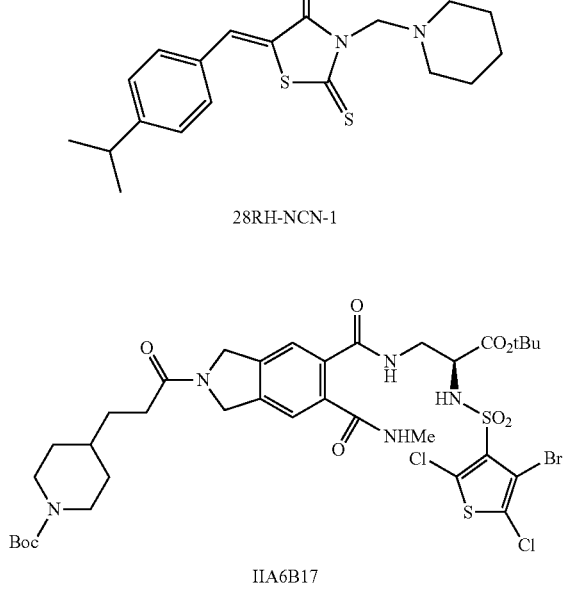

In some embodiments, a c-Myc inhibitor comprises an RNAi agent (e.g., an siRNA) or an antisense oligonucleotide that inhibits expression of c-Myc. In some embodiments a c-Myc inhibitor comprises an antibody or aptamer that specifically binds to c-Myc.

IV. NF-kB Modulators

An "NF-kB modulator" as used herein can be any compound that modulates the synthesis, activation, translocation, and/or DNA binding activity of NF-kB or otherwise affects NF-kB activity. Such modulation can often involve modulating one or more proteins upstream of NF-kB in the NF-kB pathway (e.g., a component of an NF-kB signaling module). In some embodiments, an NF-kB modulator is an NF-kB inhibitor, e.g., any compound that inhibits the synthesis, activation, translocation, and/or DNA binding activity of NF-kB or otherwise downregulates or inhibits NF-kB signaling. In some embodiments, an NF-kB modulator is an NF-kB activator, e.g., any compound that increases the synthesis, activation, translocation, and/or DNA binding activity of NF-kB or otherwise upregulates or induces NF-kB signaling. In some embodiments, an NF-kB inhibitor is a compound that inhibits an NF-kB signaling module or a component thereof. Thus as used herein, an NF-kB modulator, e.g., inhibitor, could modulate NF-KB by intervening in the NF-kB signaling pathway in any of a variety of ways, in various embodiments of the invention. In some embodiments, a compound inhibits nuclear translocation of NF-kB. In some embodiments, a compound inhibits phosphorylation and degradation of IkBα. Reduces NF-kB activation through the formation of conjugates with NF-kB.

In some embodiments, an NF-kB inhibitor is a small molecule, antioxidant, peptide, small RNA or DNA, microbial or viral protein, or engineered dominant-negative or constitutively active polypeptides or peptide, decoy oligonucleotide, etc. In some embodiments, a NF-kB inhibitor comprises an RNAi agent (e.g., an siRNA) or an antisense oligonucleotide that inhibits expression of one or more NF-kB genes (e.g., genes encoding NF-kB1, NF-kB2, RELA, REL, and/or RELB) or NF-kB pathway genes that contribute to NF-kB activity. In some embodiments an NF-kB inhibitor comprises an antibody or aptamer that specifically binds to an NF-kB protein (NF-kB1, NF-kB2, RELA, REL, and/or RELB). In some aspects, use of a p-TEFb inhibitor in combination with a compound can render the compound useful to inhibit NF-kB, whereas in the absence of the p-TEFb inhibitor the compound would not usefully inhibit NF-kB (e.g., because the compound would be too non-specific and/or toxic at the doses or amounts required).

Exemplary compounds that may be used as NF-kB inhibitors include 2-chloro-N-[3,5-di(trifluoromethyl)phenyl]-4-(trifluoromethyl)pyrimidine-5-carboxamide (also known as SP-100030); 3,4-dihydro-4,4-dimethyl-2H-1 ,2-benzoselenazine (also known as BXT-51072); declopramide (also known as Oxi-104); and dexlipotam. In one embodiment, an NF-kB inhibitor is denosumab, which inhibits RANKL, which, in turn, through its receptor RANK inhibits NF-kB. In other embodiments, an NF-kB inhibitor is a chalcone or derivative or analog thereof such as 3-hydroxy-4,3',4',5'-tetramethoxychalcone (Srinivasan B, et al., J Med Chem. 52(22):7228-35, 2009). In other embodiments, an NF-kB inhibitor is a lignan (manassantins, (+)-saucernetin, (−)-saucerneol methyl ether), sesquiterpene (costunolide, parthenolide, celastrol, celaphanol A), diterpenes (excisanin, kamebakaurin), triterpene (avicin, oleandrin), polyphenol (resveratrol, epigallocatechin gallate, quercetin), or a derivative or analog thereof (Mini Rev Med Chem. 6(8):945-51, 2006). In some embodiments, an NF-kB inhibitor inhibits NF-kappaB signaling at least in part via inhibition of IkappaBalpha phosphorylation. In some embodiments, such an NF-kB inhibitor is emetine, fluorosalan, sunitinib malate, bithionol, narasin, tribromsalan, or lestaurtinib (Miller S C. Biochem Pharmacol. 79(9):1272-80, 2010), or a derivative or analog of any of these. In some embodiments, an NF-kB inhibitor is an anti-oxidant that has been shown to inhibit activation of NF-kB, proteasome or protease inhibitors that inhibits Re1/NF-kB, or an IkBa phosphorylation and/or degradation inhibitor. A variety of compounds reported to inhibit one or more steps of NF-kappaB signaling are described in, e.g., Gilmore T D, & Herscovitch M. Oncogene, 25(51): 6887-99, 2006 and/or at the following website http://people.bu.edu/gilmore/nf-kb/inhibitors/index.html, incorporated herein by reference as of Feb. 5, 2011. In some embodiments, a compound of use is a non-steroidal anti-inflammatory agent (e.g., sodium salicylate, 5-aminosalicylic acid, ibuprofen, sulindac, indomethacin), BAY-II, thalidomide, flavopiridol, PS-341(bortezomib), Silibinin, Leptomycin B, Sesquiterpene lactones (parthenolide, ergolide), derivative of 9 aminoacridine (9AA): antimalarial agent, celecoxib (celebrex; Pfizer) COX2 inhibitor, dimethylamino-parthenolide (DMAPT), or diethylmaleate.

V. Uses

Compositions and methods of the invention may be used in vitro and/or in vivo. This section provides non-limiting examples of some of these uses. The inventive compositions and methods may be particularly useful in the treatment of neoplasms or other proliferative diseases or inflammatory diseases in vivo. However, inventive compositions and methods may also be used in vitro, e.g., for research or clinical purposes (e.g., determining the susceptibility of a subject's disease to an inventive composition or compound combination, examining the effect of a compound combination on a cell, elucidating a cellular pathway or process such as transcription, identifying or testing additional compounds for use in a method of the invention (e.g., screening assays)), producing cell populations for cell therapy, etc. While uses are described herein mainly in regard to P-TEFb inhibitors, c-Myc inhibitors, and NF-kB inhibitors, such description is exemplary and may be applied in the context of other inventive transcriptional modulator combinations and approaches described herein.

In some embodiments a P-TEFb inhibitor is used at a concentration that inhibits P-TEFb kinase activity by a desired amount. The suppression, inhibition, or reduction may be at least about 5%, 10%, 15%, 20%, 25%, 30%, 35%, 40%, 45%, 50%, 55%, 60%, 65%, 70%, 75%, 80%, 85%, 90%, 95%, 99%, or 100% of a reference level (e.g., a control level). One of skill in the art will be able to perform kinase assays to measure the level of inhibition using standard methods. A reference level may be a level that exists in the absence of the inhibitor. It will be understood that 100% inhibition is often reduction to a background level. In some embodiments a c-Myc inhibitor is used at a concentration that inhibits c-Myc DNA binding and/or transcription of one or more c-Myc target genes by a desired amount. The suppression, inhibition, or reduction may be at least about 5%, 10%, 15%, 20%, 25%, 30%, 35%, 40%, 45%, 50%, 55%, 60%, 65%, 70%, 75%, 80%, 85%, 90%, 95%, 99%, or 100% of a reference level (e.g., a control level). One of skill in the art will be able to perform suitable assays to measure c-Myc DNA binding or transcription of one or more c-Myc target genes. Optionally the assay measures transcription of a population of c-Myc target genes. In some embodiments, a P-TEFb inhibitor or c-Myc inhibitor, or both, is used at a concentration that reduces the amount of promoter-proximal Pol II at one or more c-Myc target genes (or collectively at a population of c-Myc target genes). The suppression, inhibition, or reduction may be at least about 5%, 10%, 15%, 20%, 25%, 30%, 35%, 40%, 45%, 50%, 55%, 60%, 65%, 70%, 75%, 80%, 85%, 90%, 95%, 99%, or 100% of a reference level (e.g., a control level). In some embodiments a NF-kB inhibitor is used at a concentration that inhibits NF-kB DNA binding activity and/or transcription of one or more NF-kB target genes by a desired amount. The suppression, inhibition, or reduction may be at least about 5%, 10%, 15%, 20%, 25%, 30%, 35%, 40%, 45%, 50%, 55%, 60%, 65%, 70%, 75%, 80%, 85%, 90%, 95%, 99%, or 100% of a reference level (e.g., a control level). One of skill in the art will be able to perform suitable assays to measure NF-kB binding and/or transcription of one or more NF-kB target genes. Optionally the assay measures transcription of a population of NF-kB target genes. In some embodiments, a P-TEFb inhibitor or NF-kB inhibitor, or both, is used at a concentration that reduces the amount of promoter-proximal Pol II at one or more NF-kB target genes (or collectively at a population of NF-kB target genes). The suppression, inhibition, or reduction may be at least about 5%, 10%, 15%, 20%, 25%, 30%, 35%, 40%, 45%, 50%, 55%, 60%, 65%, 70%, 75%, 80%, 85%, 90%, 95%, 99%, or 100% of a reference level (e.g., a control level).

In certain embodiments a P-TEFb inhibitor and/or c-Myc inhibitor is used at a concentration that inhibits P-TEFb kinase activity by a desired amount. The suppression, inhibition, or reduction may be at least about 5%, 10%, 15%, 20%, 25%, 30%, 35%, 40%, 45%, 50%, 55%, 60%, 65%, 70%, 75%, 80%, 85%, 90%, 95%, 99%, or 100% of a reference level (e.g., a control level).

In certain embodiments the P-TEFb inhibitor, c-Myc inhibitor, or both, is contacted with cells in an amount that inhibits cell proliferation or survival by a desired amount, e.g., by at least about 5%, 10%, 15%, 20%, 25%, 30%, 35%, 40%, 45%, 50%, 55%, 60%, 65%, 70%, 75%, 80%, 85%, 90%, 95%, 99% of a reference level (e.g., a control level) when used as a single agent.

In certain embodiments the P-TEFb inhibitor, NF-kB inhibitor, or both, is contacted with cells in an amount that inhibits an inflammatory or immune response by a desired amount, e.g., by at least about 5%, 10%, 15%, 20%, 25%, 30%, 35%, 40%, 45%, 50%, 55%, 60%, 65%, 70%, 75%, 80%, 85%, 90%, 95%, 99% of a reference level (e.g., a control level) when used as a single agent.

In general, in any embodiment of the invention in which an inhibitor is used, such inhibitor may be used at a concentration that inhibits one or more activities of its target by a desired amount. The suppression, inhibition, or reduction may be at least about 5%, 10%, 15%, 20%, 25%, 30%, 35%, 40%, 45%, 50%, 55%, 60%, 65%, 70%, 75%, 80%, 85%, 90%, 95%, 99%, or 100% of a reference level (e.g., a control level).

As used herein, "inhibit", or "inhibition" (and similar terms such as "reduce", "reduction", or "decrease") may, or may not, be complete. For example, cell proliferation, also referred to as growth, may, or may not, be decreased to a state of complete arrest for an effect to be considered one of inhibition or reduction of cell proliferation. Similarly, kinase activity or gene expression may, or may not, be decreased to a state of complete absence of activity or expression for an effect to be considered one of suppression, inhibition or reduction. Furthermore, "inhibition" may comprise preventing proliferation of a non-proliferating cell and/or inhibiting the proliferation of a proliferating cell. Similarly, inhibition of cell survival may refer to killing of a cell, or cells, such as by necrosis or apoptosis, and/or the process of rendering a cell susceptible to death. The suppression, inhibition, or reduction may be at least about 5%, 10%, 15%, 20%, 25%, 30%, 35%, 40%, 45%, 50%, 55%, 60%, 65%, 70%, 75%, 80%, 85%, 90%, 95%, 99% of a reference level (e.g., a control level). In some cases the level of modulation (e.g., inhibition or reduction) compared with a control level is statistically significant. As used herein, "statistically significant" refers to a p-value of less than 0.05, e.g., a p-value of less than 0.025 or a p-value of less than 0.01, using an appropriate statistical test (e.g, ANOVA, t-test, etc.).

In certain embodiments, the survival and/or proliferation of a cell or cell population is determined by an assay selected from: a cell counting assay, a replication labeling assay, a cell membrane integrity assay, a cellular ATP-based viability assay, a mitochondrial reductase activity assay, a caspase activity assay, an Annexin V staining assay, a DNA content assay, a DNA degradation assay, and a nuclear fragmentation assay. Other exemplary assays include BrdU, EdU, or H3-Thymidine incorporation assays; DNA content assays using a nucleic acid dye, such as Hoechst Dye, DAPI, Actinomycin D, 7-aminoactinomycin D or Propidium Iodide; Cellular metabolism assays such as AlamarBlue, MTT, XTT, and CellTitre Glo; Nuclear Fragmentation Assays; Cytoplasmic Histone Associated DNA Fragmentation Assay; PARP Cleavage Assay; TUNEL staining; and Annexin staining.

In some aspects, the invention provides a method of inhibiting pause release at a plurality of Myc target genes in a cell comprising contacting the cell with a P-TEFb inhibitor and a c-Myc inhibitor. In some embodiments, pause release is inhibited at at least 50, at least 100, at least 500, or at least 1000 c-Myc target genes, e.g., as assessed by the traveling ratio (TR), described further in the Examples, wherein higher TR values indicate a higher degree of pausing, e.g., a lower degree of pause release. In some embodiments, a c-Myc target gene is among the 1000 genes that show the greatest c-Myc occupancy of the promoter region. In some embodiments a non-c-Myc target gene is among the 50 genes, 100 genes, 500 genes, or 1,000 genes that show the lowest c-Myc occupancy of the promoter region. In some embodiments a set of c-Myc target genes consists of between 5 and 1,000 genes, or any intervening number. Occupancy of the promoter region can be determined, e.g., using ChIP-Seq. One of skill in the art can also select a set of c-Myc target genes or non-c-Myc target genes using, e.g., information available in the literature or other experimental approaches. A c-Myc target gene can contain an E box or sequence recognizably related to an E box. It will be understood that a set of c-Myc target genes or non-c-Myc target genes can differ depending, e.g., on factors such as the cell type, whether the cell is a diseased cell or a normal cell, etc. When calculating a TR or occupancy, an average TR or occupancy for a plurality of genes (e.g., c-Myc target genes or non-c-Myc target genes) can be used. FIG. 8 presents non-limiting representative sets of c-Myc target and non-c-Myc target genes, respectively, in mES cells. One of skill in the art will appreciate that these sets of genes are exemplary. Other genes and sets of genes could be used if desired, e.g., to assess the effect of a P-TEFb inhibitor, c-Myc inhibitor, or combination thereof, or for other purposes. In some embodiments, such sets could contain, e.g., up to between about 3,000-4,000 genes. In some embodiments, a set of c-Myc target genes and/or non-c-Myc target genes is generated for a cell of interest, e.g., a tumor cell. Similar methods are provided for NF-kB target genes, employing an NF-kB inhibitor and a p-TEFb inhibitor.

In some embodiments in any aspect of the invention, the cell is contacted with a P-TEFb inhibitor at a concentration that does not substantially inhibit pause release at a set of non-c-Myc target genes when the cell is contacted with the P-TEFb inhibitor in the absence of a c-Myc inhibitor. For example, the TR at a set of non-c-Myc target genes can be increased by less than 5%, or less than 10%. In some embodiments the TR is increased by less than 20% at a set of non-c-Myc target genes. In some embodiments in any aspect of the invention, the cell is contacted with a P-TEFb inhibitor at a concentration that does not substantially inhibit pause release at a set of c-Myc target genes when the cell is contacted with the P-TEFb inhibitor in the absence of a c-Myc inhibitor. For example, the TR at a set of c-Myc target genes can be increased by less than 5%, or less than 10%. In some embodiments the TR is increased by less than 20% at a set of c-Myc target genes. Similar methods are provided for NF-kB target genes, employing an NF-kB inhibitor and a p-TEFb inhibitor.

Cells can be contacted with compounds for various periods of time. In certain embodiments cells are contacted for between 12 hours and 20 days, e.g., for between 1 and 10 days, for between 2 and 5 days, or any intervening range or particular value. Cells can be contacted transiently or continuously. If desired, a compound can be removed prior to assessing survival and/or proliferation (or other characteristics). A composition comprising a P-TEFb inhibitor and a c-Myc inhibitor can be used to inhibit cell proliferation or survival in vitro, e.g., to assess the sensitivity of a subject's cells to the compound combination. Compounds can be used to identify or select P-TEFb inhibitors and/or c-Myc inhibitors that may have particularly favorable properties for use in certain aspects of the invention. For example, librar(ies) comprising P-TEFb inhibitors and/or c-Myc inhibitors can be tested to identify compound combination(s) with particularly strong synergistic effects. Compound combinations of the invention can be used to study processes such as transcription.

In certain embodiments of any aspect of the invention, the cell is a vertebrate cell, e.g., a mammalian cell, e.g., a human cell. In certain embodiments the cell is a non-human animal cell, e.g., a rodent cell, e.g., mouse, rat, or rabbit cell. In certain embodiments the cell is one that proliferates aberrantly in a proliferative disease. In some embodiments the cell is a tumor cell. In some embodiments the tumor cell is a cancer stem cell. In certain embodiments the cell is a primary cell. In certain embodiments the cell comprises an infectious agent, e.g., a virus, or a portion thereof (e.g., a portion of a viral genome). In some embodiments the cell overexpresses c-Myc, relative to a normal cell. In some embodiments the cell, e.g., tumor cell, expresses a mutated c-Myc or has an amplified or mutated c-Myc gene or polymorphic variant that is associated with increased risk of a disease, e.g., a proliferative disease.

In some aspects, the invention relates to or makes use of genetically modified cells e.g., cells that have been genetically modified to render them tumorigenic. A "genetically modified" or "engineered" cell refers to a cell into which a nucleic acid has been introduced by a process involving the hand of man (or a descendant of such a cell that has inherited at least a portion of the nucleic acid). The nucleic acid may for example contain a sequence that is not naturally found in the cell, it may contain native sequences (i.e., sequences naturally found in the cell) but in a non-naturally occurring arrangement (e.g., a coding region linked to a promoter from a different gene), or altered versions of native sequences, etc. The process of transferring the nucleic acid into the cell can be achieved by any suitable technique and will often involve use of a vector (e.g., as discussed below). In some embodiments the nucleic acid or a portion thereof is integrated into the genome of the cell and/or is otherwise stably heritable. The nucleic acid may have subsequently been removed or excised from the genome, provided that such removal or excision results in a detectable alteration in the cell relative to an unmodified but otherwise equivalent cell. For example, the cell may have been engineered to overexpress an oncogene, to express a mutant version of an oncogene, and/or to have reduced or absent expression of a tumor suppressor gene.

In certain embodiments a method comprises measuring the effect of contacting a cell with a P-TEFb inhibitor and a c-Myc inhibitor on cell proliferation or survival. The cell can be contacted in vitro or in vivo. Optionally the method comprises comparing the effect of the combination with the effect of one of the agents in the absence of the other agent. In some embodiments the method comprises comparing the effect of the compound combination with a control value. In some embodiments the method comprises comparing the effect of a compound combination on a tumor cell or other aberrantly proliferating cell with the effect on a normal cell. In some embodiments the method comprises comparing the effect of a compound combination on a tumor with the effect on normal proliferating cells in the same subject. In certain embodiments of the invention a compound combination displays selective activity (e.g., selective inhibition of survival and/or proliferation, selective toxicity) against target cells (e.g., abnormally proliferating cells or other undesired cells) relative to its activity against non-target cells. For example, the IC50 of a compound may be about 2, 5, 10, 20, 50, 100, 250, 500, or 1000-fold lower for target cells versus non-target cells. In some embodiments, the IC50 of a compound may be about 2, 5, 10, 20, 50, 100, 250, 500, or 1000-fold lower for cancer cells than for non-cancer cells.

In some embodiments a compound combination of the invention is administered to a non-human subject, e.g., a non-human mammal, e.g., a rodent such as a mouse, rat, hamster, rabbit, or guinea pig; a dog, a cat, a bovine or ovine, a non-human primate, etc. In some embodiments, the subject may serve as an animal model for a proliferative disease, e.g., cancer. For example, the subject may have a tumor xenograft or may be injected with tumor cells or have a predisposition to develop tumors. In some embodiments the animal is immunocompromised. The non-human animal may be useful for assessing effect of an inventive compound combination on tumor formation, development, progression, metastasis, etc. In some embodiments the animal is used to assess efficacy and/or toxicity of a compound combination. Methods known in the art can be used for such assessment. In some embodiments, a compound combination of the invention is administered for veterinary purposes, e.g., to treat a vertebrate, e.g., domestic animal such as a dog, cat, horse, cow, sheep, etc. In some embodiments the animal is ovine, bovine, equine, feline, or canine. In some embodiments the vertebrate is an avian.

In some aspects, the invention relates to or makes use of genetically modified multi-cellular organisms. An organism at least some of whose cells are genetically engineered or that is derived from such a cell is considered a genetically engineered organism. Such an organism may be a non-human mammal. In some embodiments, the organism may serve as an animal model for cancer. For example, the subject may be a genetically engineered non-human mammal, e.g., a mouse, that has a predisposition to develop tumors. The mammal may overexpress an oncogene (e.g., as a transgene) or underexpress a tumor suppressor gene (e.g., the animal may have a mutation or deletion in the tumor suppressor gene).

In some aspects, a cell or organism is genetically modified using a suitable vector. As used herein, a "vector" may comprise any of a variety of nucleic acid molecules into which a desired nucleic acid may be inserted, e.g., by restriction digestion followed by ligation. A vector can be used for transport of such nucleic acid between different environments, e.g., to introduce the nucleic acid into a cell of interest and, optionally, to direct expression in such cell. Vectors are often composed of DNA although RNA vectors are also known. Vectors include, but are not limited to, plasmids and virus genomes or portions thereof. Vectors may contain one or more nucleic acids encoding a marker suitable for use in the identifying and/or selecting cells that have or have not been transformed or transfected with the vector. Markers include, for example, proteins that increase or decrease either resistance or sensitivity to antibiotics or other compounds, enzymes whose activities are detectable by standard assays known in the art (e.g., β-galactosidase or alkaline phosphatase), and proteins or RNAs that detectably affect the phenotype of transformed or transfected cells (e.g., fluorescent proteins). An expression vector is one into which a desired nucleic acid may be inserted such that it is operably linked to regulatory elements (also termed "regulatory sequences", "expression control elements", or "expression control sequences") and may be expressed as an RNA transcript (e.g., an mRNA that can be translated into protein or a noncoding RNA such as an shRNA or miRNA precursor). Regulatory elements may be contained in the vector or may be part of the inserted nucleic acid or inserted prior to or following insertion of the nucleic acid whose expression is desired. As used herein, a nucleic acid and regulatory element(s) are said to be "operably linked" when they are covalently linked so as to place the expression or transcription of the nucleic acid under the influence or control of the regulatory element(s). For example, a promoter region would be operably linked to a nucleic acid if the promoter region were capable of effecting transcription of that nucleic acid. One of skill in the art will be aware that the precise nature of the regulatory sequences needed for gene expression may vary between species or cell types, but can in general include, as necessary, 5' non-transcribed and/or 5' untranslated sequences that may be involved with the initiation of transcription and translation respectively, such as a TATA box, cap sequence, CAAT sequence, and the like. Other regulatory elements include IRES sequences. Such 5' non-transcribed regulatory sequences will include a promoter region that includes a promoter sequence for transcriptional control of the operably linked gene. Regulatory sequences may also include enhancer sequences or upstream activator sequences. Vectors may optionally include 5' leader or signal sequences. Vectors may optionally include cleavage and/or polyadenylations signals and/or a 3' untranslated regions. The choice and design of an appropriate vector and regulatory element(s) is within the ability and discretion of one of ordinary skill in the art. For example, one of skill in the art will select an appropriate promoter (or other expression control sequences) for expression in a desired species (e.g., a mammalian species) or cell type. One of skill in the art is aware of regulatable (e.g., inducible or repressible) expression systems such as the Tet system and others that can be regulated by small molecules and the like, as well as tissue-specific and cell type specific regulatory elements. In some embodiments, a virus vector is selected from the group consisting of adenoviruses, adeno-associated viruses, poxviruses including vaccinia viruses and attenuated poxviruses, retroviruses (e.g., lentiviruses), Semliki Forest virus, Sindbis virus, etc. Optionally the virus is replication-defective. In some embodiments a replication-deficient retrovirus (i.e., a virus capable of directing synthesis of one or more desired transcripts, but incapable of manufacturing an infectious particle) is used. Various techniques may be employed for introducing nucleic acid molecules into cells. Such techniques include transfection of nucleic acid molecule-calcium phosphate precipitates, transfection of nucleic acid molecules associated with DEAE, transfection or infection with a virus that contains the nucleic acid molecule of interest, liposome-mediated transfection, nanoparticle-mediated transfection, and the like.

The invention encompasses testing a plurality of compounds, e.g., a compound library, to identify compound(s) that have similar effects on Pol II occupancy of promoter-proximal regions as does a P-TEFb inhibitor or a c-Myc inhibitor. Such compounds can be used for a variety of purposes, e.g., in methods described herein. In some embodiments, such screens can yield new inhibitors of P-TEFb and/or c-Myc. In some embodiments, a screen is performed to identify compounds that inhibit binding of P-TEFb and c-Myc. In some embodiments, such a compound is used in combination with second P-TEFb or c-Myc inhibitor. Compounds to be screened can come from any source, e.g., natural product libraries, combinatorial libraries, libraries of compounds that have been approved by the FDA or another health regulatory agency for use in treating humans, etc. The method may encompass performing high throughput screening. In some embodiments at least 100; 1,000; or 10,000 compounds are tested. Compounds identified as "hits" can then be tested in directed assays, e.g., to assess their effect on P-TEFb and/or c-Myc activity or expression, cell proliferation, etc. Compounds identified as having a useful effect can be selected and systematically altered, e.g., using rational design, to optimize binding affinity, avidity, specificity, or other parameters. For example, one can screen a first library of compounds using the methods described herein, identify one or more compounds that are "hits" or "leads" (by virtue of, for example, their ability to inhibit metastasis), and subject those hits to systematic structural alteration to create a second library of compounds structurally related to the hit or lead. The second library can then be screened using the methods described herein or other methods known in the art. A compound can be modified or selected to achieve (i) improved potency, (ii) decreased toxicity and/or decreased side effects; (iii) modified onset of therapeutic action and/or duration of effect; and/or (iv) modified pharmacokinetic parameters (absorption, distribution, metabolism and/or excretion).

The invention provides methods of determining whether a compound combination comprising a P-TEFb inhibitor and a c-Myc inhibitor (e.g., any of the P-TEFb inhibitors and/or c-Myc inhibitors described herein) is suitable therapy for a subject in need of treatment, e.g., for a proliferative disease. In some embodiments, cells are obtained from a subject in need of treatment, e.g., for a proliferative disease, and contacted with a P-TEFb inhibitor and a c-Myc inhibitor. The ability of the compound combination to inhibit cell proliferation and/or survival is assessed. If the compound combination significantly inhibits cell proliferation and/or survival in concentrations correlating with those that are acceptable and achievable in vivo, the compound combination is a suitable therapy for the subject (or, said another way, the subject is a suitable candidate for treatment with the compound combination). Results of such an assay may be useful for selecting a therapeutic regimen for a subject, e.g., for selecting a dose.

Compounds can be used or administered in a single dose or multiple doses, e.g., regularly for example, 1, 2, 3, or more times a day, weekly, bi-weekly, or monthly. In some embodiments, a compound is administered continuously to the subject (e.g., by release from an implant, pump, sustained release formulation, etc.). The dose administered can depend on multiple factors, including the identity of the compound, weight of the subject, frequency of administration, etc.

In certain embodiments, compositions and compound combinations of the present invention are provided for use in medicine, e.g., for treating a subject in need thereof. The subject may be suffering from a disease (e.g., a proliferative disease such as a cancer) warranting medical and/or surgical attention and/or may be at increased risk of developing a disease relative to an average member of the population and/or in need of prophylactic therapy. In certain embodiments, the compositions and/or methods are used in the treatment of a proliferative disease, e.g., a disease characterized by abnormal, aberrant, or unwanted cell proliferation. In some embodiments, the proliferative disease is selected from the group consisting of benign neoplasms, cancer, inflammatory disease, auto-immune disease, and angiogenesis-associated diseases.

In some embodiments a disease treated according to the instant invention is a disease associated with increased c-Myc function, e.g., as a result of increased expression of c-Myc and/or activating mutation(s) or polymorphisms in the c-Myc gene. c-Myc function could be assessed, e.g., by measuring expression of one or more c-Myc target genes. Suitable methods for such measurement are known in the art (e.g., Northern blots, RT-PCR, microarrays, RNA-Seq, etc.). Increased expression of c-Myc could be due, e.g., to gene amplification, mutation or polymorphism in regulatory region(s) of the c-Myc gene, dysregulation of factor(s) driving c-Myc expression, loss of a microRNA that normally inhibits c-Myc expression, etc. A mutation may be present in all of an individual's somatic cells, or may be present in only some of the cells, e.g., those associated with the disease, e.g., those exhibiting abnormal proliferation, survival, or other behavior. As used herein, "gene" comprises a region of DNA that is transcribed to RNA (which RNA may include an open reading frame that encodes a polypeptide or may be a functional RNA such as a tRNA, snRNA, miRNA or precursor thereof) and associated regulatory element(s), e.g., transcriptional regulatory elements such as promoter, enhancer(s), etc. It will be appreciated that regulatory elements may be present within a transcribed or untranscribed region.

A polymorphism can refer to a sequence variation that is present in 1% or less of a given population of individuals, e.g., humans (typically as assessed based on a sample of the population). A polymorphism can be a single nucleotide polymorphism (SNP). A population can be defined, e.g., geographically (e.g., by country or region (U.S., E.U., China, Japan) or by categories such as those used in the International HapMap Project (Yoruba in Ibadan, Nigeria (abbreviation: YRI); Japanese in Tokyo, Japan (abbreviation: JPT); Han Chinese in Beijing, China (abbreviation: CHB)1 CEPH (Utah residents with ancestry from northern and western Europe) (abbreviation: CEU)), which can represent certain Sub-Saharan African, Asian, Asian, and European, populations, respectively (See, e.g., The International HapMap Consortium. A second generation human haplotype map of over 3.1 million SNPs. Nature 449, 851-861, 2007). See also, http://hapmap.ncbi.nlm nih.gov/index.html.en and the dbSNP database (http://www.ncbi.nlm nih gov/projects/SNP/).

SNPs associated with c-Myc upregulation in cancer cells have been identified. See, e.g., Wright, J B, et al. Upregulation of c-MYC in Cis Through a Large Chromatin Loop Linked to a Cancer Risk-Associated SNP in Colorectal Cancer Cells. Mol Cell Biol. 2010 Jan. 11; Pomerantz M M, et al. The 8q24 cancer risk variant rs6983267 shows long-range interaction with MYC in colorectal cancer. Nat Genet. 2009 August; 41(8):882-4. Epub 2009 Jun. 28. In some embodiments, a SNP is in the c-Myc enhancer.

In some embodiments, an inventive method comprises testing a subject to determine whether the subject has such a mutation or polymorphism and/or has increased c-Myc function, e.g., in tumor cells derived from the subject. In some embodiments such a subject is identified as being a suitable candidate for administering a combination therapy of the invention.

In some embodiments, the present invention provides a method of treating a proliferative disease in a subject suffering therefrom, the method comprising administering to the subject therapeutically effective amounts of a P-TEFb inhibitor and a c-Myc inhibitor. "Therapeutically effective amounts of a P-TEFb inhibitor and a c-Myc inhibitor" means that the amounts administered are therapeutically effective at least when the compounds are administered in combination. "Administered in combination" means that both compounds are administered to a subject, i.e., a P-TEFb inhibitor and a c-Myc inhibitor are administered to the subject. Such administration is sometimes referred to herein as coadministration. The compounds can be administered in the same composition or separately. When they are coadministered, the two may be given simultaneously or sequentially and in either instance, may be given separately or in the same composition, e.g., a unit dosage (which includes both the P-TEFb inhibitor and the c-Myc inhibitor). The P-TEFb inhibitor can be given prior to or after administration of the c-Myc inhibitor, provided that they are given sufficiently close in time to have a desired effect of inhibiting aberrant or unwanted cell proliferation or survival.

The invention provides methods comprising administering to the subject therapeutically effective amounts of a P-TEFb inhibitor and an NF-kB inhibitor. "Therapeutically effective amounts of a P-TEFb inhibitor and an NF-kB inhibitor" means that the amounts administered are therapeutically effective at least when the compounds are administered in combination.

In some embodiments, administration in combination of first and second compounds (e.g., a p-TEFb inhibitor and a c-Myc inhibitor or a P-TEFb inhibitor and an NF-kB inhibitor), is performed such that (i) a dose of the second compound is administered before more than 90% of the most recently administered dose of the first agent has been metabolized to an inactive form or excreted from the body; or (ii) doses of the first and second compound are administered within 48 hours of each other, or (iii) the agents are administered during overlapping time periods (e.g., by continuous or intermittent infusion); or (iv) any combination of the foregoing. Multiple compounds are considered to be administered in combination if the afore-mentioned criteria are met with respect to all compounds, or in some embodiments, if each compound can be considered a "second compound" with respect to at least one other compound of the combination. The compounds may, but need not be, administered together as components of a single composition. In some embodiments, they may be administered individually at substantially the same time (e.g., within less than 1, 2, 5, or 10 minutes of one another). In some embodiments they may be administered individually within a short time of one another (by which is meant less than 3 hours, sometimes less than 1 hour, sometimes within 10 or 30 minutes apart). The compounds may, but need not, be administered by the same route of administration. One or more than one P-TEFb inhibitor and one or more than one c-Myc inhibitor or NF-kB inhibitor can be administered according to the present methods.

In some embodiments, the proliferative disease is a solid tumor. In some embodiments, the proliferative disease is a hematological malignancy. In certain embodiments, the proliferative disease is a benign neoplasm. In other embodiments, the neoplasm is a malignant neoplasm. In certain embodiments, the proliferative disease is a cancer. In some embodiments at least some of the tumor cells overexpresses c-Myc relative, e.g., to cells of the type from which the tumor is believed to have arisen and/or typical values observed in normal cells. In some embodiments, c-Myc is mutated or amplified in the tumor cells.

Exemplary tumors that may be treated using compounds of the present invention include colon cancer, lung cancer (e.g., small cell lung cancer, non-small cell lung cancer), bone cancer, pancreatic cancer, stomach cancer, esophageal cancer, skin cancer, brain cancer, liver cancer, ovarian cancer, cervical cancer, uterine cancer, testicular cancer, prostate cancer, bladder cancer, kidney cancer, neuroendocrine cancer, breast cancer, gastric cancer, eye cancer, gallbladder cancer, laryngeal cancer, oral cancer, penile cancer, glandular tumors, rectal cancer, small intestine cancer, gastrointestinal stromal tumors (GISTs), sarcoma, carcinoma, melanoma, urethral cancer, vaginal cancer, to name but a few.

In some embodiments, the cancer is a hematological malignancy. In some embodiments, the hematological malignancy is a lymphoma. In some embodiments, the hematological malignancy is a leukemia. Examples of hematological malignancies that may be treated using an inventive compound include, but are not limited to, acute lymphoblastic leukemia (ALL), acute myelogenous leukemia (AML), chronic myelogenous leukemia (CML), chronic lymphocytic leukemia (CLL), hairy cell leukemia, Hodgkin's lymphoma, non- Hodgkin's lymphoma, cutaneous T-cell lymphoma (CTCL), peripheral T-cell lymphoma (PTCL), Mantle cell lymphoma, B-cell lymphoma, acute lymphoblastic T cell leukemia (T-ALL), acute promyelocytic leukemia, and multiple myeloma.

In certain embodiments, the disease, e.g., proliferative disease, is an inflammatory disease. In some embodiments the disease is an autoimmune disease. In certain embodiments, the disease is associated with pathologic neovascularization. Other proliferative diseases include, e.g., neurofibromatosis, atherosclerosis, pulmonary fibrosis, arthritis, psoriasis, hypertrophic scar formation, inflammatory bowel disease, post-transplantation lymphoproliferative disorder, etc. In some embodiments, a compound combination of the invention is used for treatment of any disease for which use of a CDK9 inhibitor is contemplated in the art. See, e.g., discussion in references describing CDK9 inhibitors. Diseases of interest include infectious diseases, cardiovascular diseases, and neurodegenerative diseases.

Infectious diseases include infections caused by pathogens such as viruses, bacteria, fungi and/or parasites. Virus-induced infectious diseases include diseases caused by infection with retroviruses, hepadnaviruses, herpesviruses, flaviviruses, adenoviruses, togaviruses and poxviruses. Infectious diseases can be caused by viruses comprising, but not limited to viruses such as HIV-1, HIV-2, HTLV-I and HTLV-II, hepadnaviruses such as HBV, herpesviruses such as Herpes simplex virus I (HSV I), herpes simplex virus 11 (HSV II), Epstein-Barr virus (EBV), varicella zoster virus (VZV), human cytomegalovirus (HCMV) or human herpesvirus 8 (HHV-8), flaviviruses such as HCV, West Nile or Yellow Fever virus, human papilloma virus, poxviruses, Sindbis virus or adenoviruses. Certain transcription factors of lentiviruses and retroviruses such as HIV and T-lymphotropic virus type I recruit P-TEFB to their promoter regions, attenuating Pol II transcriptional pausing (Barboric and Peterlin, 2005; Cho et al., 2007; Wei et al., 1998; Yoshida, 2001; Zhou et al., 2006). These viruses have thus generated means to overcome pause control. In some embodiments a combination therapy of the invention is used in treatment of an infectious disease, e.g., a viral infection, wherein c-Myc is involved in viral life cycle or pathogenesis and/or wherein the infectious agent, e.g., virus, causes upregulated c-Myc expression or activity, e.g., in infected cells.

In some embodiments, a combination therapy of the invention is used in treatment of a proliferative disease, e.g., cancer, that is at least in part caused by a viral infection. For example, HCV, EBV, and HPV are associated with various types of cancer.

In some embodiments, compositions and methods of the present invention are useful for inhibiting smooth muscle cell proliferation. In some embodiments, compositions and methods of the present invention are useful for inhibiting restenosis, e.g., after angioplasty or vascular surgery. In certain embodiments, such effects are achieved by using a drug-eluting stent coated with a P-TEFb inhibitor and a c-Myc inhibitor. Alternately either the P-TEFb inhibitor or the c-Myc inhibitor is administered using the stent and the other agent is administered using a different route, e.g., intravenously or orally.

Doses of compounds may range from about 1 µg to 10,000 mg, e.g., about 10 µg to 5000 mg, e.g., from about 100 µg to 1000 mg once or more per day, week, month, or other time interval. Stated in terms of subject body weight, doses in certain embodiments of the invention range from about 1 µg to 20 mg/kg/day, e.g., from about 1 m/kg/day to 10 mg/kg/day. In certain embodiments doses are expressed in terms of surface area rather than weight, e.g., between about 1 mg/m$^2$ to about 5,000 mg/m$^2$. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. It is often the case that a maximum dose be used, that is, the highest safe dose according to sound medical judgment. In the case of compounds that have been tested already in pre-clinical studies and/or clinical trials, considerable information is already available that can be used in selecting doses.

In certain embodiments each of the compounds is administered in an amount that is therapeutically effective when used as a single agent. In certain embodiments at least one of the compounds (e.g., both compounds) is/are administered in an amount that would be sub-therapeutic or less than optimally therapeutic if the compound were administered as a single agent. A "sub-therapeutic amount" as used herein refers to an amount that is less than the amount that would produce a therapeutically useful result in the subject if administered in the absence of the other compound. For example, a sub-therapeutic amount of a P-TEFb inhibitor in some embodiments is one that would not produce a desired therapeutic result in the subject in the absence of the administration of a c-Myc inhibitor. In some embodiments, a sub-therapeutic amount of a c-Myc inhibitor is one that would not produce a desired therapeutic result when administered as a single agent, e.g., in the absence of a p-TEFB inhibitor. In some embodiments, a sub-therapeutic amount of an NF-kB inhibitor is one that would not produce a desired therapeutic result when administered as a single agent, e.g., in the absence of a p-TEFB inhibitor. In certain embodiments at least one of the compounds is administered in an amount that is lower than the maximum tolerated dose, e.g., the compound is administered in an amount that is about 5%, 10%, 20%, 30%, 40%, 50%, 60%, 70%, 80%, or 90% of the effective amount or maximum tolerated dose.

For example, in some embodiments of the invention flavopiridol or a flavopiridol analog is coadministered with a c-Myc inhibitor to treat a proliferative disease, wherein the amount of the flavopiridol or analog used is lower than that required to have an equivalent therapeutic effect in the absence of the c-Myc inhibitor. In some embodiments of the invention roscovitine or a roscovitine analog is used in combination with a c-Myc inhibitor to inhibit cell proliferation or survival wherein the concentration of roscovitine or roscovitine analog used is lower than that required to cause the same level of inhibition in the absence of the c-Myc inhibitor.

In some embodiments, flavopiridol or a flavopiridol analog is administered using a dosing regimen that has been used for flavopiridol in a clinical trial. As known in the art, a "dosing regimen" can include dose level(s), dosing interval, and other aspects(s) that characterize the manner in which a compound is administered to a subject, such as the route of administration, rate and duration of a bolus administration or infusion.

In some embodiments, a c-Myc inhibitor is added to a dosing regimen for flavopiridol or roscovatine that has been tested in a clinical trial. For purposes of this invention, a regimen that has been tested in a clinical trial, e.g., a regimen that has been shown to be acceptable in terms of safety and, in some embodiments, showing at least some evidence of efficacy, will be referred to as a "standard regimen". For example, flavopiridol and roscovitine have each been tested as single agents and in combination with a variety of different agents. A c-Myc inhibitor can be added to such regimens. In some embodiments, the flavopiridol or roscovitine is administered at a lower dose than the maximum dose tested in such trials. In some embodiments, the flavopiridol or roscovitine is administered at a lower dose than the maximum tolerated dose identified in such trial(s). The invention provides such methods for any P-TEFb inhibitor that is tested in a clinical trial, e.g., any flavpiridol analog or roscovatine analog.

In some embodiments, flavopiridol or a flavopiridol analog is administered using a dosing regimen such as those described in PCT/US2006/009162 (WO/2006/101846) DOSING REGIMEN OF FLAVOPIRIDOL FOR TREATING CANCER IN PARTICULAR CLL. Such dosing regimen can comprise administering an effective dose of an IV bolus followed by an effective dose of an IV infusion. See also, Byrd, B., et al., Blood, 15 Vol. 109, No. 2, pp. 399-404, 2007.

Many anti-cancer agents exhibit significant toxicity, often due to their effects on normal cells, e.g., proliferating cells such as cells lining the GI tract, skin cells, cells of the hematopoietic system. For example, flavopiridol can exhibit significant toxicity, which can limit the tolerated dose. In clinical cancer trials of flavopiridol, fatigue, venous thromboses, and diarrhea were the main side effects of doses that achieved plasma flavopiridol levels of approximately 400 nM during a 72 hour treatment period (See, e.g., Innocenti F., et al. Clin Cancer Res. 6(9):3400-3405, 2000.)

A phase I trial of roscovitine was performed with a 7-day b.i.d. p.o. schedule (Benson, C., et al. British Journal of Cancer, 96, 29-37, 2007). Twenty-one patients (median age 62 years, range: 39-73 years) with a variety of solid tumors were treated with doses of 100, 200 and 800 b.i.d. Dose-limiting toxicities were seen at 800 mg b.i.d.; grade 3 fatigue, grade 3 skin rash, grade 3 hyponatraemia and grade 4 hypokalaemia. Other toxicities included reversible raised creatinine (grade 2), reversible grade 3 abnormal liver function and grade 2 emesis. An 800 mg dose was investigated further in 12 patients. One patient with a rapid increase in creatinine on day 3 had a reversible fall in renal perfusion, with full recovery by day 14, and no changes suggestive of renal tubular damage. Further dose escalation was precluded by hypokalaemia.

The invention encompasses the recognition that administering a P-TEFb inhibitor in combination with a c-Myc inhibitor can result in enhanced efficacy relative to administration of the P-TEFb inhibitor in the absence of the c-Myc inhibitor. The P-TEFb inhibitor when administered in combination with a c-Myc inhibitor can have a higher therapeutic index than the P-TEFb inhibitor when administered in the absence of the c-Myc inhibitor. Without wishing to be bound by any theory, the co-administration of a c-Myc inhibitor may selectively amplify or augment the effects of inhibiting P-TEFb on transcription of c-Myc target genes, which genes include a large number of genes that promote cell proliferation, relative to the effect of the P-TEFb inhibitor on non-c-Myc target genes. Thus, for example, transcription of genes that encode proteins necessary for basic "housekeeping" functions may be relatively less affected by the P-TEF inhibitor than transcription of c-Myc target genes. The invention encompasses the recognition that administering a c-Myc inhibitor in combination with a P-TEFb inhibitor can result in enhanced efficacy relative to administration of the c-Myc inhibitor in the absence of the P-TEFb inhibitor. In some embodiments, even a low concentration or dose of a P-TEFb inhibitor is sufficient to usefully augment the effect of a c-Myc inhibitor. For example, a concentration or dose of P-TEFb inhibitor that exhibits minimal effect on transcription of non-c-Myc target genes can be used. Without limitation, enhanced efficacy provided by the inventive methods may, for example, (i) permit a therapeutically useful effect using a dosing regimen of P-TEFb inhibitor, e.g., flavopiridol, that has been deemed to lack significant efficacy in one or more clinical trials; (ii) permit use of a P-TEFb inhibitor, e.g., flavopiridol, in a proliferative disease or tumor type in which it has been deemed to lack significant efficacy in one or more clinical trials; (iii) permit a therapeutically useful effect to be achieved using a c-Myc inhibitor that does not show a therapeutically useful effect as a single agent (or in some embodiments in combination with one or more existing chemotherapeutic agents(s)). In other embodiments, similar enhanced efficacy may be provided by the combination of an NF-kB inhibitor and a p-TEFb inhibitor. The invention encompasses the use of c-Myc inhibitors and/or NF-kB inhibitors that are not expected to be therapeutically useful, e.g., as single agents, or in combination with existing chemotherapeutic agent, e.g., because they have insufficient activity in vitro when used at concentrations expected to be achievable in vivo.

The invention further encompasses the recognition that administering a P-TEFb inhibitor in combination with an NF-kB inhibitor can result in enhanced efficacy relative to administration of the P-TEFb inhibitor in the absence of the NF-kB inhibitor and/or enhanced efficacy relative to administration of the NF-kB inhibitor in the absence of the P-TEFb inhibitor. In certain embodiments at least one of the compounds (P-TEFb inhibitor and/or c-Myc inhibitor and/or NF-kB) is administered in an amount that would be sub-therapeutic or less than optimally therapeutic if the compound were administered as a single agent. In certain embodiments at least one of the compounds is administered in an amount that is lower than the maximum tolerated dose, e.g., the compound is administered in an amount that is about 10%, 20%, 30%, 40%, 50%, 60%, 70%, 80%, or 90% of the effective amount or maximum tolerated dose.

For example, in some embodiments of the invention flavopiridol or a flavopiridol analog is used in combination with a c-Myc inhibitor to inhibit cell proliferation, wherein the concentration of the flavopiridol or analog used is lower than that required to cause the same level of inhibition in the absence of the c-Myc inhibitor. In some embodiments of the invention roscovitine or a roscovitine analog is used in combination with a c-Myc inhibitor to inhibit cell proliferation or survival wherein the concentration of roscovitine or roscovitine analog used is lower than that required to cause the same level of inhibition in the absence of the c-Myc inhibitor. In some embodiments of the invention flavopiridol or a flavopiridol analog (or a different P-TEFb inhibitor) is used in combination with an NF-KB inhibitor to inhibit an inflammatory or immune response, wherein the concentration of the NF-kB inhibitor used is lower than that required to cause the same level of inhibition in the absence of the flavopiridol or analog. In some embodiments of the invention roscovitine or a roscovitine analog is used in combination with an NF-kB inhibitor to inhibit cell proliferation or survival wherein the concentration of NF-kB inhibitor used is lower than that required to cause the same level of inhibition in the absence of the roscovitine or roscovitine analog inhibitor. In some embodiments, the use of lower doses of an NF-kB inhibitor can reduce inhibition of other signaling pathways.

In some embodiments of the invention, cell state is modified ex vivo and the resulting cells are administered to a subject, e.g., for therapeutic purposes. Such methods may use cells harvested from the subject to which the modified cells are administered (autologous) or may use cells harvested from a different donor (e.g., an individual of the same species who may be genetically identical or non-identical to the subject). The donor and recipient may be compatible with regard to blood type and/or may be matched with regard to at least some MHC class I and/or MHC class II antigens, e.g., with respect to 1, 2, 3, 4, 5, or 6 major HLA antigens. Thus in some embodiments the invention provides a method comprising: (a) providing one or more cells of a first cell state; (b) modifying the cell state of said cell(s) according to a method described herein; and (c) administering at least some of the resulting cells to a subject in need thereof. In some embodiments, step (b) comprises contacting the cell(s) with a c-Myc modifier and a modifier of a second transcriptional modulator. In some embodiments, step (b) comprises contacting the cells with a c-Myc inhibitor and an inhibitor of a second transcription factor. In some embodiments, step (b) comprises contacting the cell(s) with an NF-kB modifier and a modifier of a second transcriptional modulator. In some embodiments, step (b) comprises comprising contacting the cell(s) with a P-TEFb inhibitor and a c-Myc inhibitor or NF-kB inhibitor. In some embodiments, cells are expanded in vitro, optionally in medium comprising one or more of the modifier(s), prior to administering them to a subject. Cells can be adminstered to a subject using any suitable method known in the art. For example, cells can be injected, infused, or implanted into the subject.

As used herein, treatment or treating can include amelioration, cure, and/or maintenance of a cure (i.e., the prevention or delay of recurrence) of a disease, e.g., a proliferative disease, e.g., cancer. Treatment after a disorder has started aims to reduce, ameliorate or altogether eliminate the disorder, and/or at least some of its associated symptoms, to prevent it from becoming more severe, to slow the rate of progression, or to prevent the disorder from recurring once it has been initially eliminated. Treatment can be prophylactic, e.g., administered to a subject that has not been diagnosed with cancer, e.g., a subject with a significant risk of developing cancer. A subject at risk of cancer recurrence has been diagnosed with cancer and has been treated such that the cancer appears to be largely or completely eradicated. In some embodiments, a therapeutic method of the invention comprises providing a subject in need of treatment for a disease of interest herein, e.g., a proliferative disease, e.g., cancer. In some embodiments, a therapeutic method of the invention comprises diagnosing a subject in need of treatment for a disease of interest herein, e.g., cancer.

In some embodiments the subject is at risk of cancer or cancer recurrence. A subject at risk of cancer may be, e.g., a subject who has not been diagnosed with cancer but has an increased risk of developing cancer as compared with an age-matched control of the same sex. For example, the subject may have a risk at least 1.2 times that of an age and sex matched control. Determining whether a subject is considered "at risk" of cancer may be within the discretion of the skilled practitioner caring for the subject. Any suitable diagnostic test(s) and/or criteria can be used. For example, a subject may be considered "at risk" of developing cancer if (i) the subject has a mutation, genetic polymorphism, gene or protein expression profile, and/or presence of particular substances in the blood, associated with increased risk of developing or having cancer relative to other members of the general population not having such mutation or genetic polymorphism; (ii) the subject has one or more risk factors such as having a family history of cancer, having been exposed to a carcinogen or tumor-promoting agent or condition, e.g., asbestos, tobacco smoke, aflatoxin, radiation, chronic infection/inflammation, etc., advanced age; (iii) the subject has one or more symptoms of cancer, etc.

The compounds may be used in vitro or in vivo in an effective amount, by which is meant an amount sufficient to achieve a biological response of interest, e.g., reducing gene expression or protein activity, reducing Pol II pause release (e.g., increasing the traveling ratio) at one or more genes, reducing one or more symptoms or manifestations of a disease or condition, e.g., reducing the likelihood of recurrence or progression of a disease.

The compounds may be administered in a pharmaceutical composition. A pharmaceutical composition can comprise a variety of pharmaceutically acceptable carriers. Pharmaceutically acceptable carriers are well known in the art and include, for example, aqueous solutions such as water, 5% dextrose, or physiologically buffered saline or other solvents or vehicles such as glycols, glycerol, oils such as olive oil or injectable organic esters that are suitable for administration to a human or non-human subject. In some embodiments, a pharmaceutically acceptable carrier or composition is sterile. A pharmaceutical composition can comprise, in addition to the active agent, physiologically acceptable compounds that act, for example, as bulking agents, fillers, solubilizers, stabilizers, osmotic agents, uptake enhancers, etc. Physiologically acceptable compounds include, for example, carbohydrates, such as glucose, sucrose, lactose; dextrans; polyols such as mannitol; antioxidants, such as ascorbic acid or glutathione; preservatives; chelating agents; buffers; or other stabilizers or excipients. The choice of a pharmaceutically acceptable carrier(s) and/or physiologically acceptable compound(s) can depend for example, on the nature of the active agent, e.g., solubility, compatibility (meaning that the substances can be present together in the composition without interacting in a manner that would substantially reduce the pharmaceutical efficacy of the pharmaceutical composition under ordinary use situations) and/or route of administration of the composition. Compounds can be present as salts in a composition. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. It will also be understood that a compound can be provided as a pharmaceutically acceptable pro-drug, or an active metabolite can be used. Furthermore it will be appreciated that agents may be modified, e.g., with targeting moieties, moieties that increase their uptake, biological half-life (e.g., pegylation), etc. It will be understood that compounds can exist in a variety or protonation states and can have a variety of configurations and may exist as solvates (e.g., with water (i.e. hydrates) or common solvents) or different crystalline forms (e.g., polymorphs). The structures presented here are intended to encompass embodiments exhibiting such alternative protonation states, configurations, and forms.

The pharmaceutical composition could be in the form of a liquid, gel, lotion, tablet, capsule, ointment, transdermal patch, etc. A pharmaceutical composition can be administered to a subject by various routes including, for example, parenteral administration. Exemplary routes of administration include intravenous administration; respiratory administration (e.g., by inhalation), nasal administration, intraperitoneal administration, oral administration, subcutaneous administration, intrasynovial administration, transdermal administration, and topical administration. For oral administration, the compounds can be formulated with pharmaceutically acceptable carriers as tablets, pills, dragees, capsules, liquids, gels, syrups, slurries, suspensions, etc. In some embodiments a compound may be administered directly to a tissue e.g., a tissue, e.g., in which cancer cells are or may be present or in which the cancer is likely to arise. Direct administration could be accomplished, e.g., by injection or by implanting a sustained release implant within the tissue. In some embodiments at least one of the compounds is administered by release from an implanted sustained release device, by osmotic pump or other drug delivery device. A sustained release implant could be implanted at any suitable site. In some embodiments, a sustained release implant may be particularly suitable for prophylactic treatment of subjects at risk of developing a recurrent cancer. In some embodiments, a sustained release implant delivers therapeutic levels of the active agent for at least 30 days, e.g., at least 60 days, e.g., up to 3 months, 6 months, or more. One skilled in the art would select an effective dose and administration regimen taking into consideration factors such as the patient's weight and general health, the particular condition being treated, etc. Exemplary doses may be selected using in vitro studies, tested in animal models, and/or in human clinical trials as standard in the art. The compound(s) can be administered by the same or different routes (e.g., a P-TEFb inhibitor could be administered intravenously and a c-Myc inhibitor administered orally, or vice versa), and likewise for a P-TEFb inhibitor and NF-kB inhibitor.

In some embodiments, the pharmaceutical composition is delivered by means of a microparticle or nanoparticle or a liposome or other delivery vehicle or matrix. A number of biocompatible synthetic or naturally occurring polymeric materials are known in the art to be of use for drug delivery purposes. Examples include polylactide-co-glycolide, polycaprolactone, polyanhydride, cellulose derivatives, and copolymers or blends thereof. Liposomes, for example, which consist of phospholipids or other lipids, are nontoxic, physiologically acceptable and metabolizable carriers that are relatively simple to make and administer.

Pharmaceutical compositions comprising a P-TEFb inhibitor, a c-Myc inhibitor, or both, are an aspect of the invention. Pharmaceutical compositions comprising a P-TEFb inhibitor, an NF-kB inhibitor, or both, are an aspect of the invention. The pharmaceutical composition(s) may be packaged with a suitable label describing their use in a method of the invention (e.g., instructions for use to treat a proliferative, inflammatory, or immune-mediated disease). The invention provides a kit or pack containing a first pharmaceutical composition comprising a P-TEFb inhibitor and a second pharmaceutical composition comprising a c-Myc inhibitor, optionally with a suitable label describing their use in a method of the invention. The invention provides a kit or pack containing a first pharmaceutical composition comprising a P-TEFb inhibitor and a second pharmaceutical composition comprising an NF-kB inhibitor, optionally with a suitable label describing their use in a method of the invention.

In some embodiments compounds (e.g., P-TEFb inhibitor, c-Myc inhibitor, or both) are formulated in unit dosage form for ease of administration and uniformity of dosage. The term "unit dosage form" as used herein refers to a physically discrete unit of agent appropriate for the subject to be treated. In some embodiments, a unit dosage form contains a sub-therapeutic amount of a P-TEFb inhibitor or a c-Myc inhibitor. In some embodiments, a unit dosage form of a P-TEFb inhibitor and a unit dosage form of a c-Myc inhibitor are provided. In some embodiments, at least one unit dosage form contains a subtherapeutic amount of compound.

In some embodiments compounds (e.g., P-TEFb inhibitor, NF-kB inhibitor, or both) are formulated in unit dosage form for ease of administration and uniformity of dosage. In some embodiments, a unit dosage form contains a sub-therapeutic amount of a P-TEFb inhibitor or an NF-kB inhibitor. In some embodiments, a unit dosage form of a P-TEFb inhibitor and a unit dosage form of an NF-kB inhibitor are provided. In some embodiments, at least one unit dosage form contains a sub-therapeutic amount of compound.

The combination therapies of the invention may be used together with one or more additional pharmacological therapies or non-pharmacological therapies (e.g., surgery, radiation), or combinations thereof, for treating a subject. One of skill in the art can select an appropriate additional therap(ies) based, e.g., on the particular disease.

For example, non-limiting examples of cancer chemotherapeutics that can be useful with the methods disclosed herein for treating cancer include alkylating and alkylating-like agents such as Nitrogen mustards (e.g., Chlorambucil, Chlormethine, Cyclophosphamide, Ifosfamide, and Melphalan), Nitrosoureas (e.g., Carmustine, Fotemustine, Lomustine, and Streptozocin), Platinum agents (i.e., alkylating-like agents) (e.g., Carboplatin, Cisplatin, Oxaliplatin, BBR3464, and Satraplatin), Busulfan, Dacarbazine, Procarbazine, Temozolomide, ThioTEPA, Treosulfan, and Uramustine; Antimetabolites such as Folic acids (e.g., Aminopterin, Methotrexate, Pemetrexed, and Raltitrexed); Purines such as Cladribine, Clofarabine, Fludarabine, Mercaptopurine, Pentostatin, and Thioguanine; Pyrimidines such as Capecitabine, Cytarabine, Fluorouracil, Floxuridine, and Gemcitabine; Spindle poisons/mitotic inhibitors such as Taxanes (e.g., Docetaxel, Paclitaxel) and Vincas (e.g., Vinblastine, Vincristine, Vindesine, and Vinorelbine); Cytotoxic/antitumor antibiotics such anthracyclines (e.g., Daunorubicin, Doxorubicin, Epirubicin, Idarubicin, Mitoxantrone, Pixantrone, and Valrubicin), compounds naturally produced by various species of *Streptomyces* (e.g., Actinomycin, Bleomycin, Mitomycin, Plicamycin) and Hydroxyurea; Topoisomerase inhibitors such as Camptotheca (e.g., Camptothecin, Topotecan and Irinotecan) and Podophyllums (e.g., Etoposide, Teniposide); Monoclonal antibodies for cancer immunotherapy such as anti-receptor tyrosine kinases (e.g., Cetuximab, Panitumumab, Trastuzumab), anti-CD20 (e.g., Rituximab and Tositumomab), and others for example Alemtuzumab, Bevacizumab, and Gemtuzumab; Photosensitizers such as Aminolevulinic acid, Methyl aminolevulinate, Porfimer sodium, and Verteporfin; Tyrosine kinase inhibitors such as Cediranib, Dasatinib, Erlotinib, Gefitinib, Imatinib, Lapatinib, Nilotinib, Sorafenib, Sunitinib, and Vandetanib; serine/threonine kinase inhibitors, (e.g., inhibitors of Abl, c-Kit, insulin receptor family member(s), EGF receptor family member(s), mTOR, Raf kinase family, phosphatidyl inositol (PI) kinases such as PI3 kinase, PI kinase-like kinase family members, cyclin dependent kinase family members, Aurora kinase family), growth factor receptor antagonists, and others such as retinoids (e.g., Alitretinoin and Tretinoin), Altretamine, Amsacrine, Anagrelide, Arsenic trioxide, Asparaginase (e.g., Pegaspargase), Bexarotene, Bortezomib, Denileukin diftitox, Estramustine, Ixabepilone, Masoprocol, Mitotane, and Testolactone, Hsp90 inhibitors, proteasome inhibitors, HDAC inhibitors, angiogenesis inhibitors, e.g., anti-vascular endothelial growth factor agents such as Bevacizumab, matrix metalloproteinase inhibitors, pro-apoptotic agents (e.g., apoptosis inducers), anti-inflammatory agents, etc.

EXAMPLES

Example 1

Pol II Tends to Occupy Promoter Regions

Figure 1B:
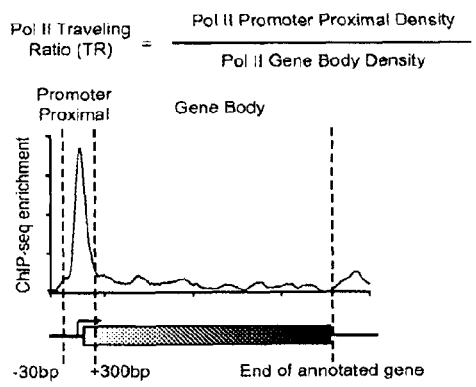

We used chromatin immunoprecipitation coupled to high-throughput sequencing (ChIP-seq) to determine how Pol II occupies the ES cell genome (FIG. 1). An antibody that binds to the N-terminus of the largest subunit of Pol II (N-20) was used, allowing us to monitor Pol II independent of the phosphorylation status of its C-terminal domain (CTD). We found that the bulk of Pol II occupied the promoter proximal region of the vast majority of genes (FIG. 1A). This tendency to occupy promoter proximal regions was evident both for genes that are actively transcribed (with H3K4me3- and H3K79me2-modified nucleosomes) and for non-productive genes that show evidence of initiation but not elongation (with H3K4me3-, but not H3K79me2-modified nucleosomes). At actively transcribed genes, low levels of Pol II signal were observed throughout the transcribed region up to the polyadenylation site, with higher signals observed downstream where transcription termination takes place. These data are consistent with more lengthy occupancy of promoter and terminator regions than the central body of actively transcribed genes.

Figure 1C:
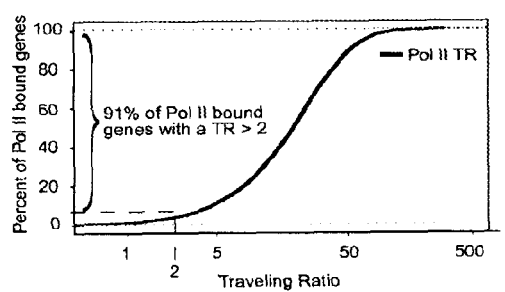
Figure 9A:
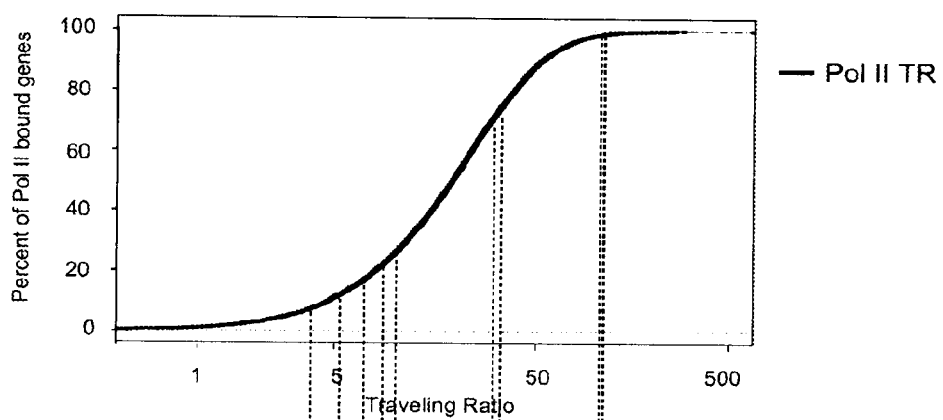
FIGS. 9A to 9B. Example genes with varying traveling ratios. (A) A plot of the percent of Pol II bound genes with the indicated TR value or less. Each example gene depicted below is shown in red. (B) Gene plots showing the Pol II occupancy at a given gene and the corresponding TR value to provide the reader with a general idea of how Pol II occupancy at a gene is related to TR. There is a very small correlation ($R^2=0.17$) between gene length and TR, but gene length normalized versions of the TR produce no meaningful changes to our results.
Figure 9B:
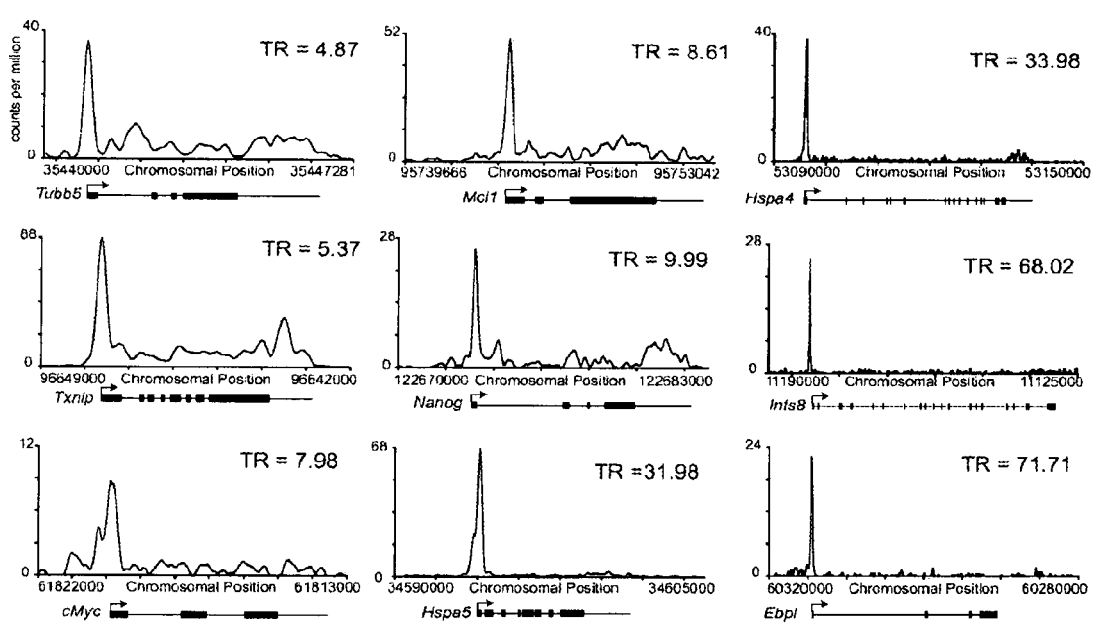

The presence of high polymerase density at the promoter region relative to the gene body has previously been cited as evidence for promoter-proximal pausing or some form of post-initiation regulation in *E. coli, Drosophila* and human cells (reviewed in Fuda et al., 2009; Price, 2008; Wade and Struhl, 2008). The pattern of Pol II binding we observed in the present study suggests that promoter-proximal pausing occurs frequently in mES cells. To further characterize Pol II occupancy in mES cells, we calculated the relative ratio of Pol II density in the promoter-proximal region and the gene body (FIG. 1B), which has been termed the traveling ratio (TR) (Reppas et al., 2006) or the pausing index (Zeitlinger et al., 2007). At genes where the rate of promoter-proximal clearance is similar to the rate of initiation, the TR is close to 1 (Reppas et al., 2006). However, at genes where promoter-proximal clearance is lower than the initiation rate, the traveling ratio is greater than 1. FIG. 9 shows genes with varying traveling ratios to illustrate how different Pol II density information is converted to traveling ratio. Using this metric, we found that 91% of genes have a Pol II TR of more than 2, confirming that higher Pol II density is detected in the promoter-proximal region than in the gene body at the vast majority of genes (FIG. 1C). The presence of high polymerase density in the promoter regions of most active ES cell genes suggests that these genes experience some form of post-initiation regulation.

The large subunit of Pol II contains a C-terminal domain (CTD) that is modified at various stages of transcription; Pol II is recruited into the preinitiation complex with a hypophosphorylated CTD, the CTD is phosphorylated on Serine 5 (Ser5P) during initiation and then on Serine 2 (Ser2P) during elongation (reviewed in Saunders et al., 2006; Sims et al., 2004). To determine how these two phosphorylated forms of Pol II occupy ES cell genes, ChIP-Seq experiments were conducted with antibodies directed against these two phosphorylated forms of the CTD (FIG. 1A). Ser5P Pol II was detected in the promoter region and the transcribed region of active genes, with the peak located in the promoter proximal region. For genes that experience initiation but not elongation (non-productive), Ser5P Pol II was detected only within the promoter region, as expected. Ser2P Pol II was detected predominantly downstream of the promoter region, with the peak in the region downstream of the polyadenylation site where termination likely takes place. These results are consistent with the idea that Pol II typically experiences a promoter proximal, rate-limiting step after being recruited to promoters and after becoming Ser5 phosphorylated. Pol II may also experience a slow release from DNA in regions of transcription termination (Core et al., 2008; Glover-Cutter et al., 2008).

Example 2

P-TEFb Inhibition Prevents Pause Release at Most Active Genes

Figure 2A:
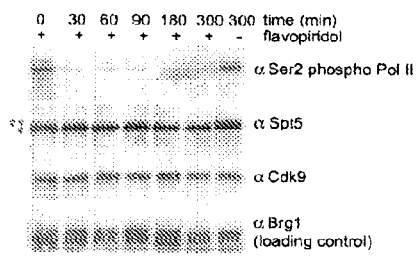
FIGS. 2A-2D. P-TEFb inhibition prevents release of promoter proximal Pol II. (A) mES cells were treated with 1 μM flavopiridol for the indicated time. Extracts were analyzed by Western blot using antibodies against Pol II Ser2P, Spt5, Cdk9 and Brg1 (used as a loading control). ** indicates higher molecular weight Spt5 species, most likely the phosphorylated C-terminal repeat form as reported in (Yamada et al., 2006), that is flavopiridol sensitive. * indicates lower molecular weight Spt5 species. See also FIG. 10A. (B) RNA Pol II (all) ChIP-seq analysis in mES cells treated with control (DMSO for 60 minutes, black) or flavopiridol (1 µM for 60 minutes, red). This panel shows the changes in Pol II occupancy at four example actively transcribed genes following flavopiridol treatment, demonstrating how Pol II remains occupied in the promoter proximal region but is depleted in the transcribed region. See also FIG. 10B. (C) Pol II traveling ratio distribution in flavopiridol-treated and control-treated mES cells using the same analysis as described in FIG. 1C for active genes (Pol II bound with H3K79me2-modified nucleosomes). Higher TR values indicate a higher degree of pausing. A general shift to the right shows a trend in active genes getting a higher TR following flavopiridol treatment, thus becoming more paused. (D) Pol II traveling ratio distribution for non-productive genes in mES cells (Pol II bound but without H3K79me2-modified nucleosomes), demonstrating that the TR distribution remains relatively the same for non-productive genes whether treated with control or flavopiridol.
Figure 2B:
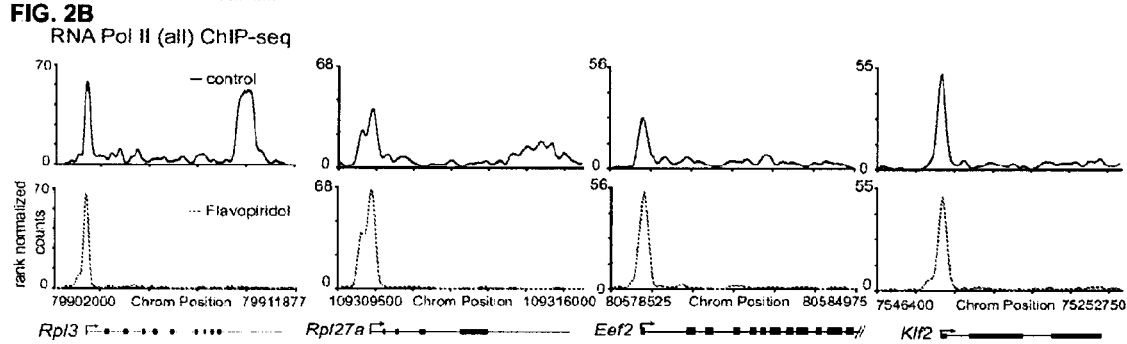
Figure 2C:
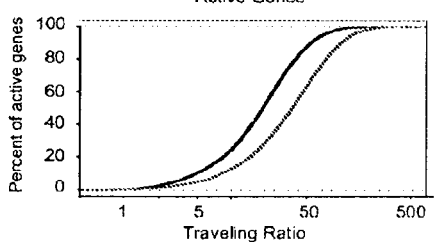
Figure 2D:
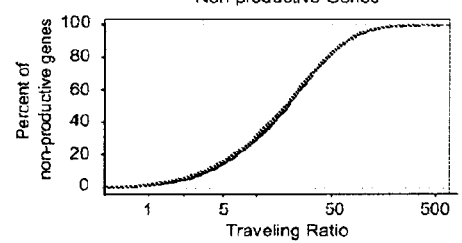
Figure 10A:
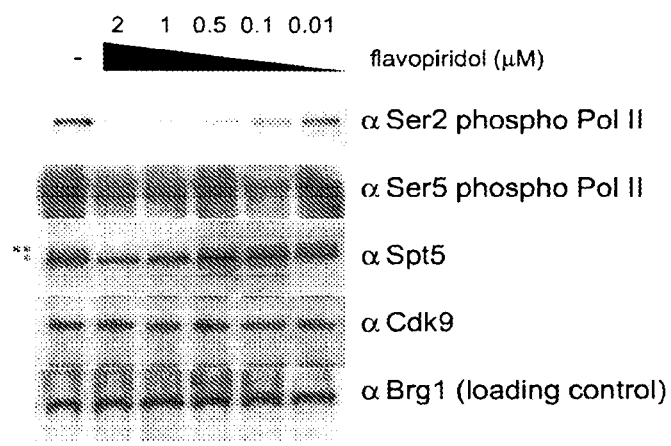
FIGS. 10A to 10B. Flavopiridol treatment in mES cells results in loss of phosphorylation at P-TEFb targets. (A) mES cells were treated with the indicated flavopiridol concentration or DMSO alone (−), for 60 minutes. Nuclear extracts were analyzed by Western blot using specific antibodies against Ser2P Pol II, Ser5P Pol II, Spt5, Cdk9 and Brg1 (loading control). **—higher molecular weight Spt5 species, most likely the phosphorylated C-terminal repeat form as reported in (Yamada et al., 2006), that is flavopiridol sensitive. *—lower molecular weight Spt5 species. (B) Pol II density at the gene end (region defined by +/−1 kb from the 3' end of the gene) is plotted from mES cells treated with DMSO versus flavopiridol for all active, non-overlapping genes. The vast majority of genes have reduced Pol II occupancy in this region following P-TEFb inhibition.
Figure 10B:
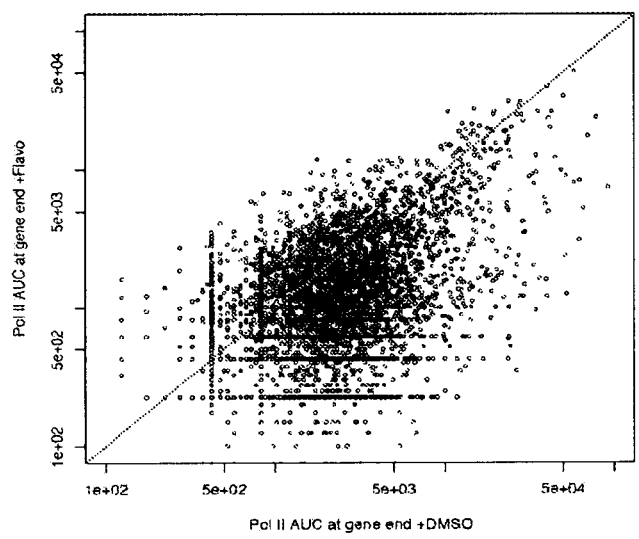

The pattern of Pol II occupancy of genes suggests that a post-initiation regulatory step, such as pause release, may be important for transcriptional control of most genes. The *Drosophila* Hsp70 gene is regulated subsequent to initiation by P-TEFb-dependent pause release (L is et al., 2000). Active P-TEFb, a heterodimer consisting of the cyclin-dependent kinase Cdk9 and a cyclin component (CycT1, CycT2 or CycK), phosphorylates at least three targets important for transcriptional control: the Spt5 subunit of DSIF, the NelfE subunit of NELF, and Ser2 of the Pol II CTD (Ahn et al., 2004; Kim and Sharp, 2001; L is et al., 2000; Marshall et al., 1996; Marshall and Price, 1995; Ni et al., 2008; Ni et al., 2004; Wada et al., 1998b; Yamada et al., 2006). To assess the role of P-TEFb-dependent pause release in global transcriptional control, we repeated the ChIP-Seq experiment for total Pol II in mES cells treated with flavopiridol, an inhibitor of Cdk9 kinase activity (Chao et al., 2000; Chao and Price, 2001; Ni et al., 2004). As expected, flavopiridol treatment caused reduced phosphorylation of Spt5 and Pol II Ser2 within 60 min, while Ser5 phosphorylation remained unaffected (FIGS. 2A and 10A) (Ni et al., 2004). If Pol II pause release is required at transcribed genes, we would expect that in the presence of flavopiridol, Pol II molecules would remain associated with promoter proximal pause sites but be depleted from DNA further downstream. This change in the pattern of Pol II occupancy was observed at most actively transcribed genes (FIG. 2B). We analyzed traveling ratios to further evaluate changes in Pol II occupancy genome-wide. TR changes with flavopiridol treatment were generally observed at actively transcribed genes, where promoter proximal Pol II signals showed relatively small changes, but Pol II signals further downstream were depleted FIGS. 2C and 10B). We found that 75% of genes had a change in Pol II TR of at least 1.5 upon drug treatment. As expected, TRs were generally unchanged at genes that normally experience initiation but not elongation (FIG. 2D). These results suggest that P-TEFb-dependent pause release is required for Pol II transcription of most actively transcribed genes in mES cells.

Example 3

Promoter Proximal Sites are Co-Occupied by Pol II, DSIF and NELF

P-TEFb antagonizes the negative elongation activity of the pause factors DSIF and NELF (Cheng and Price, 2007; Kim and Sharp, 2001; Wada et al., 1998b; Yamada et al., 2006). DSIF (Spt4 and Spt5) and NELF (NelfA, NelfB, NelfC/D, and NelfE) are both associated with promoter-proximal Pol II at genes regulated through pausing (Wada et al., 1998a; Wu et al., 2003; Yamaguchi et al., 1999). Following the transition to elongation, NELF dissociates and a form of DSIF remains associated with the elongation complex (Andrulis et al., 2000; Wu et al., 2003). If P-TEFb-dependent pause release is generally required at genes transcribed by Pol II, the pause factors DSIF and NELF should occupy the promoter proximal regions of these genes together with Pol II.

Figure 11A:
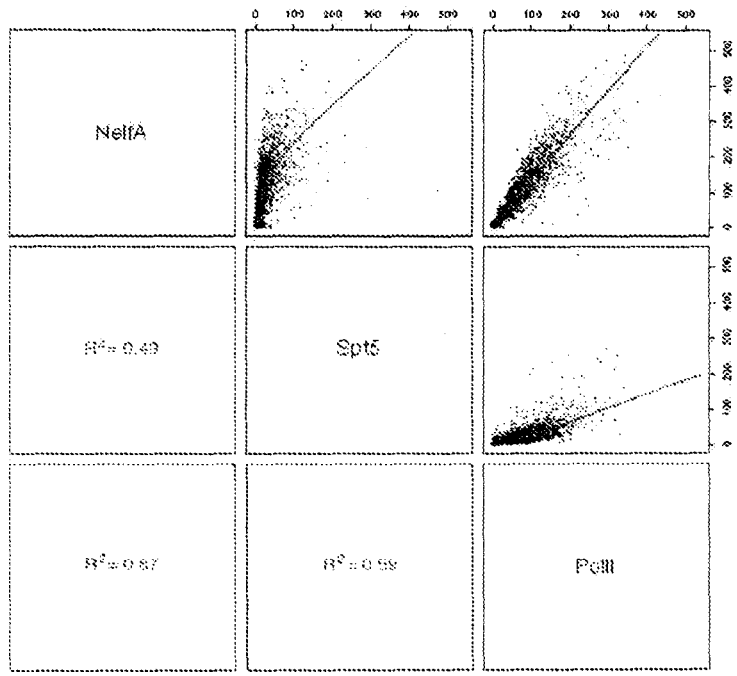
FIG. 11A to 11C. DSIF and NELF co-occupy Pol II in the promoter proximal region following P-TEFb inhibition. Spt5, NelfA and Pol II ChIP-seq occupancy is highly correlative. (A) Pairwise correlation analysis of Spt5, NelfA and Pol II (all) ChIP-seq occupancy in mES cells. This demonstrates that Spt5 and NelfA ChIP-seq occupancy positively correlates with Pol II occupancy. (B) Western blot analysis of mES cells treated with 1 mM flavopiridol or control for 60 minutes prior. Nuclear extracts were analyzed with specific antibodies against Ser2P Pol II, Spt5, Cdk9 and Brg1 (loading control). **—higher molecular weight Spt5 species, most likely the phosphorylated C-terminal repeat form, that is flavopiridol sensitive. *—lower molecular weight Spt5 species. (C) Average gene binding for NelfA and Spt5 following 1 mM flavopiridol (red) or control (black) for 60 minutes in mES cells. The average ChIP-chip enrichment was determined in each bin (250 bp) in each condition and plotted from −4 kb to +2 kb.
Figure 11B:
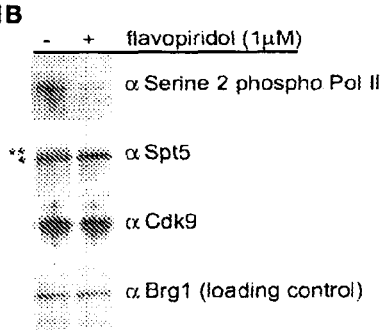

We used ChIP-Seq to determine the genome-wide occupancy of the NELF subunit NelfA and the DSIF subunit Spt5 in murine ES cells (FIG. 3). The results revealed that NelfA and Spt5 occupy precisely the same promoter-proximal sites as Pol II throughout the genome (FIG. 3A). The co-occupancy of Pol II, NelfA and Spt5 in promoter-proximal regions was evident at both actively transcribed genes and at genes that experience transcription initiation but not elongation (non-productive) (FIG. 3A). Spt5 and NelfA occupancy positively correlates with Pol II occupancy (FIG. 11A). As expected, the largest NelfA and Spt5 peaks were detected in the promoter-proximal region, but only Spt5 was also enriched further downstream in actively transcribed genes (FIG. 3A). The Spt5 enrichment at the 3' end of actively transcribed genes was similar to that of Ser2P Pol II, suggesting it remains associated with Pol II until termination. The NelfA and Spt5 peaks overlapped with the promoter-proximal site of the Pol II peak, which is flanked by H3K4me3 modified nucleosomes (FIGS. 3B and C). These results demonstrate that the pause factors DSIF and NELF co-occupy the promoter proximal regions of genes together with Pol II, consistent with the model that P-TEFb-dependent pause release is generally required at genes transcribed by Pol II.

Figure 3A:
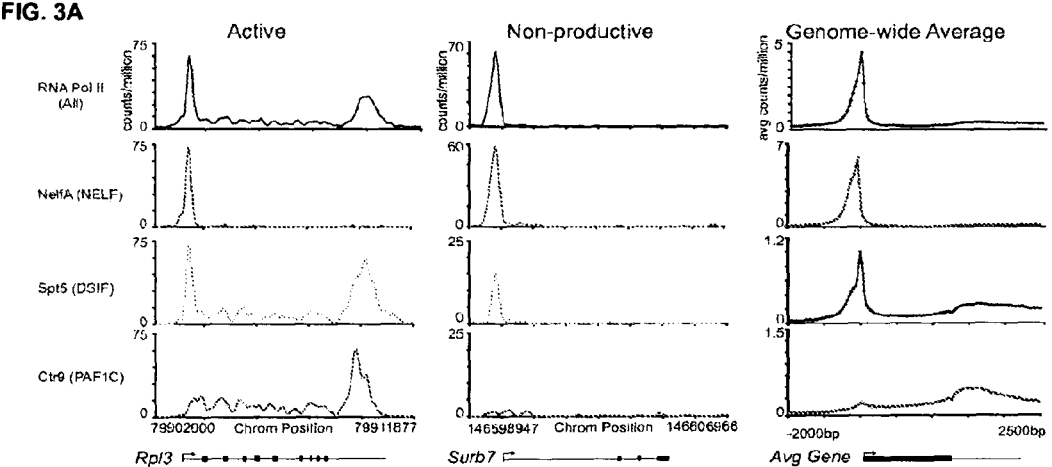
FIGS. 3A to 3D. DSIF and NELF co-occupy most genes with Pol II. (A) Binding of Pol II (all), NelfA (NELF subunit), Spt5 (DSIF subunit) and Ctr9 (PAF1 subunit) using ChIP-seq analysis at a representative active gene (Rpl3), and non-productive gene (Surb7) in mES cells. Genome-wide binding averages (introns are not depicted in this representation), in 50 bp bins, are shown for each factor to display the general binding patterns along the transcription unit of RefSeq genes, from 2 kb upstream of the transcriptional start site to 2.5 kb downstream of the end of each annotated gene. (B) Heatmap representation of ChIP-seq binding for Pol II (all; grey), NelfA (orange), Spt5 (green) and H3K4me3 (purple) at all mouse RefSeq genes, rank ordered from most Pol II to lowest Pol II. The indicated color means enrichment and white means no enrichment show the correlation between Pol II enrichment and enrichment for these factors. See also FIG. 11 (C) Spatial distribution of the distance of Spt5, NelfA and H3K4me3 peaks from the promoter proximal Pol II peak at each enriched Pol II gene, demonstrating that Spt5 and NelfA occupancy generally overlaps with Pol II peaks. (D) ChIP-seq binding plots showing Pol II (all), Spt5 (DSIF), NelfA (NELF), elongation-associated chromatin modification (H3K79me2) and TSSa-RNA reads (Seila et al., 2008) that map to this genomic region at a bidirectional initiated gene (Hsd17b12) and unidirectional initiated gene (Rpl6). Red TSSa-RNA arrows represent RNA species that map in the antisense direction to the Hsd17b12 gene, and blue TSSa-RNA arrows represent RNA species that map in the sense direction to the Hsd17b12 and Rpl6 genes.
Figure 3B:
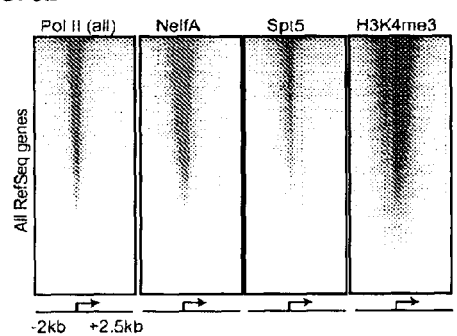
Figure 3C:
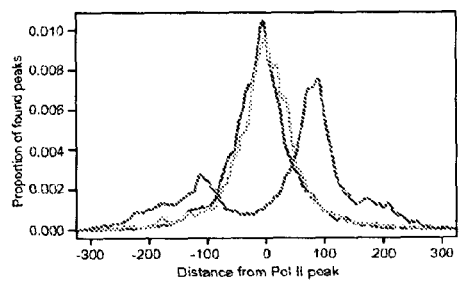

Factors such as the PAF1 complex are involved in post-initiation events that are independent of promoter-proximal pausing. PAF1 is involved in elongation, mRNA processing events and elongation-associated chromatin modifications (reviewed in Saunders et al., 2006; Sims et al., 2004). To test if the Pol II promoter proximal peak is specific for factors involved in promoter proximal pausing, we conducted ChIP-Seq with the Ctr9 subunit of the PAF1 complex. Although a limited signal could be detected in the promoter-proximal region of some genes, Ctr9 occupancy did not generally overlap with the promoter proximal Pol II peak (FIG. 3A). Ctr9 was typically found within coding regions of active genes, just downstream of promoter proximal Pol II, and extending to the 3' end of transcribed genes. Ctr9 occupancy peaked at the 3' end of actively transcribed genes, which is similar to the results obtained for Ser2P Pol II and Spt5, suggesting it remains associated with Pol II until termination. The Ctr9 ChIP-seq data indicates that the PAF1 complex generally associates with the transcribed portion of most active genes, which is consistent with its proposed roles in elongation, mRNA processing and chromatin modification (Adelman et al., 2006; Krogan et al., 2003; Pokholok et al., 2002; Zhu et al., 2005). These results support the view that the Pol II promoter proximal peaks represent regions of post-initiation regulation and not simply an artifact of the ChIP-Seq method.

Figure 11C:
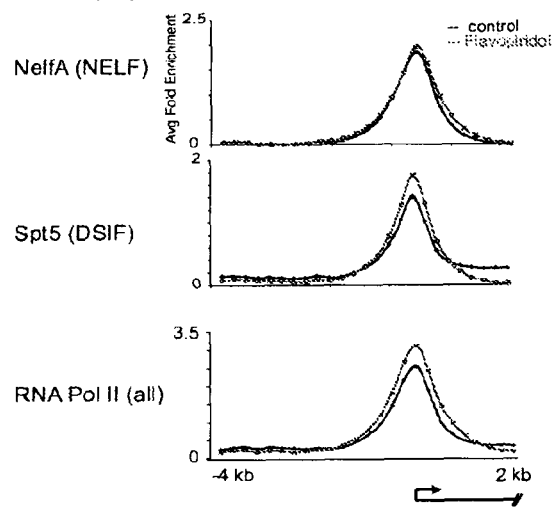

DSIF and NELF function prior to P-TEFb at genes regulated by pause release (reviewed in Fuda et al., 2009; Peterlin and Price, 2006; Saunders et al., 2006). This predicts that DSIF and NELF should be present at promoter proximal sites with Pol II in the presence of flavopiridol. We used ChIP-chip to determine if Spt5 and NelfA co-occupy promoter proximal sites with Pol II when P-TEFb activity is inhibited by flavopiridol. The results showed that Spt5 and NelfA continue to co-occupy promoter proximal sites with Pol II following flavopiridol treatment (FIG. 11C). Spt5 was depleted downstream of these promoter proximal sites following flavopiridol treatment, supporting the model that Spt5 localization in the gene body is dependent on Pol II, which agrees with previously published results at individual genes (Ni et al., 2008; Ni et al., 2004). These results indicate that DSIF and NELF co-occupy promoter proximal sites with Pol II prior to P-TEFb function.

Figure 3D:
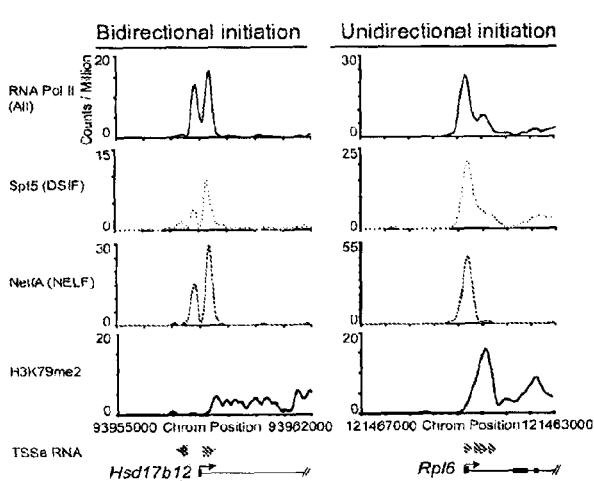

It was recently reported that Pol II can initiate transcription in both the sense and antisense direction at many genes (Core et al., 2008; Neil et al., 2009; Seila et al., 2008; Xu et al., 2009). We separated genes into bidirectional and unidirectional classes based on evidence for sense and anti-sense transcription start site associated RNAs (TSSa-RNAs) in ES cells (Seila et al., 2008). To determine how DSIF and NELF occupy the promoter-proximal regions of these two classes of genes, we re-examined the ChIP-seq data for Pol II, Spt5, NelfA and H3K79me2 (a marker for elongation) at higher resolution (FIG. 3D). Approximately 65% of active genes with TSSa-RNA reads fell into the bidirectional class, and at the promoters of these genes we found the two sites occupied by Pol II were both co-occupied by NelfA and Spt5. Approximately 35% of active genes with TSSa-RNA reads fell into the unidirectional class, and at the promoters of these genes we found the one site occupied by Pol II was co-occupied by NelfA and Spt5. These results demonstrate that the pause factors DSIF and NELF generally co-occupy promoter proximal regions wherever Pol II is found, whether initiation is occurring in one direction or two, further supporting the model that P-TEFb-dependent pause release may be a general feature of transcription initiation by Pol II.

Example 4

Pause Factor Knockdown Alters Pol II Gene Occupancy

Figure 4A:
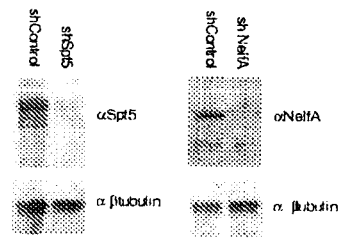
FIGS. 4A to 4C. DSIF knockdown alters Pol II occupancy at many genes. (A) Spt5 protein levels following shRNA-mediated Spt5 knockdown in mES cells as determined by Western blot using an antibody against Spt5 (left). NelfA protein levels following shRNA-mediated NelfA knockdown in mES cells as determined by Western blot using an antibody against NelfA (right). β-Tubulin protein levels are used as a loading control. (B) RNA Pol II (all) ChIP-seq binding density in shControl (black), shSpt5 (orange) and shNelfA (blue) mES cells analysis at five active genes in mES cells. (C)RNA Pol II TR calculations in shControl, shSpt5 and shNelfA mES cells using the same analysis as described in FIG. 1C, showing that many genes become less paused following Spt5 knockdown and a more subtle change following NelfA knockdown. Lower TR values indicate a lower degree of pausing. Therefore, a shift in TR curve to the left indicates a general trend is to become less paused. See also FIG. 12.

The pause factors NELF and DSIF co-occupy promoters with Pol II at most genes that experience transcription initiation. Previous studies have shown that loss of NELF causes a decrease in Pol II density at promoters, and thus a decrease in Pol II traveling ratio (or pausing index), at a small number of *Drosophila* genes (Muse et al., 2007). To determine how loss of vertebrate NELF or DSIF might influence Pol II occupancy, we used shRNA-mediated knockdown of NelfA and Spt5 followed by Pol II ChIP-seq analysis in mES cells (FIG. 4).

Figure 4B:
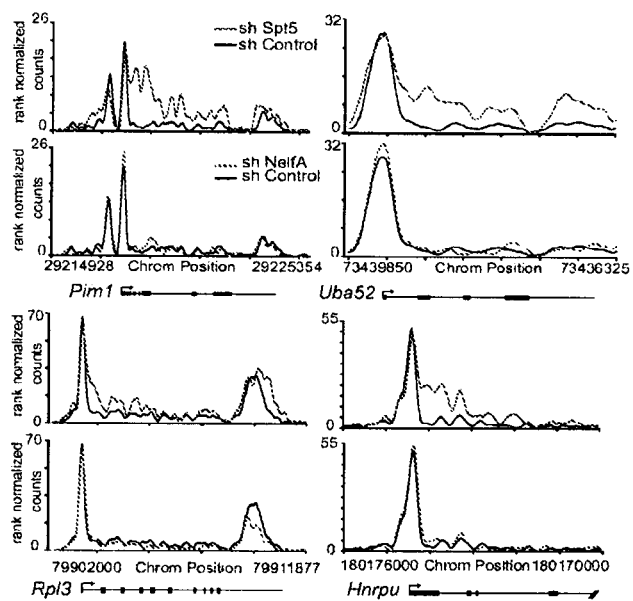
Figure 4C:
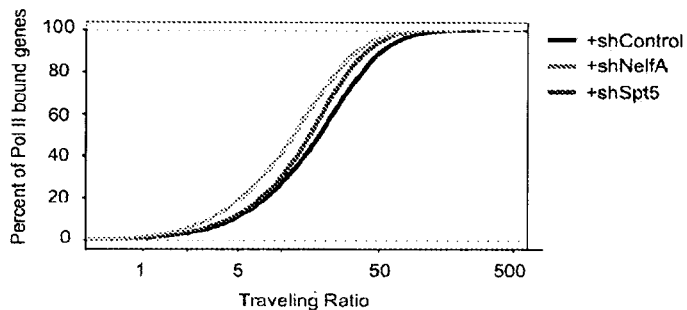
Figure 12A:
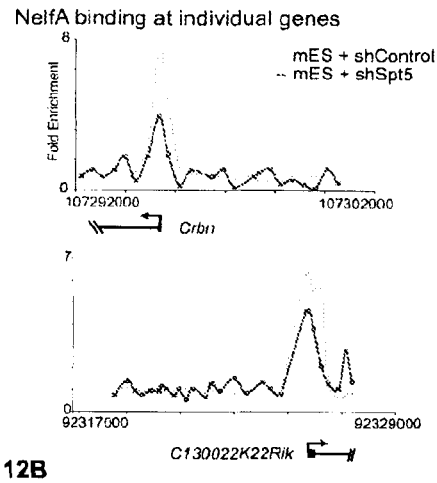
FIGS. 12A to 12G. Spt5 associates with chromatin following NelfA knockdown and NelfA associates with chromatin following Spt5 knockdown. Spt5 and NelfA knockdown cause a decrease in promoter-proximal Pol II occupancy at a subset of genes. (A) Individual gene examples of NelfA binding in shControl (blue) and shSpt5 (red) mES cells using ChIP-chip. (B) Average gene binding for NelfA in shControl (blue) and shSpt5 (red) mES cells. The average NelfA enrichment was determined in each bin (250 bp) in each cell type and plotted from −4 kb to +2 kb. (C) Individual gene examples of Spt5 binding in shControl (blue) and shNelfA (red) mES cells using ChIP-chip. Fold enrichment is plotted over the indicated chromosomal region. (D) Average gene binding for Spt5 in shControl (blue) and shNelfA (red) mES cells. The average Spt5 enrichment was determined in each bin (250 bp) in each cell type and plotted from −4 kb to +2 kb. (E) Pol II TR analysis at active genes in mES cells following shControl (black), shSpt5 (orange) and shNelfA (blue) knockdown. Lower TR values indicate a lower degree of pausing. Therefore, a shift in TR curve to the left indicates a general trend in this gene class to become less paused. This plot shows that Pol II occupancy at active genes is altered most dramatically following Spt5 knockdown compared to NelfA knockdown, which causes very minimal effects at this gene class. (F) Pol II TR analysis at non-productive genes in mES cells following shControl (black), shSpt5 (orange) and shNelfA (blue) knockdown. Lower TR values indicate a lower degree of pausing. Therefore, a shift in TR curve to the left indicates a general trend in this gene class to become less paused. This plot shows that Pol II occupancy at non-productive genes is altered following both Spt5 and NelfA knockdown. However, a stronger effect occurs following Spt5 knockdown, as shown by the larger shift in TR curve. Taking FIG. S4E and FIG. S4F together, we find that 1) Spt5 knockdown effects Pol II occupancy both active and non-productive genes, 2) NelfA knockdown mainly effects Pol II occupancy at non-productive genes and 3) Spt5 knockdown has a more dramatic effect on Pol II occupancy than NelfA knockdown. (G) RNA Pol II (all) ChIP-seq occupancy at three non-productive genes in mES cells in shControl (black), shSpt5 (orange) or shNelfA (blue). Pol II occupancy in the promoter proximal region is reduced at many non-productive genes following Spt5 or NelfA knockdown, which is thus responsible for the shift in TR in FIG. 12F.
Figure 12B:
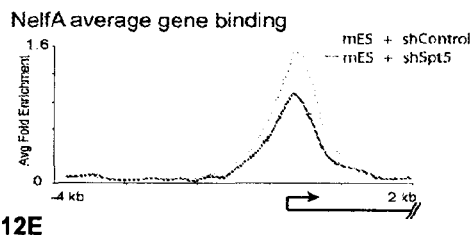
Figure 12C:
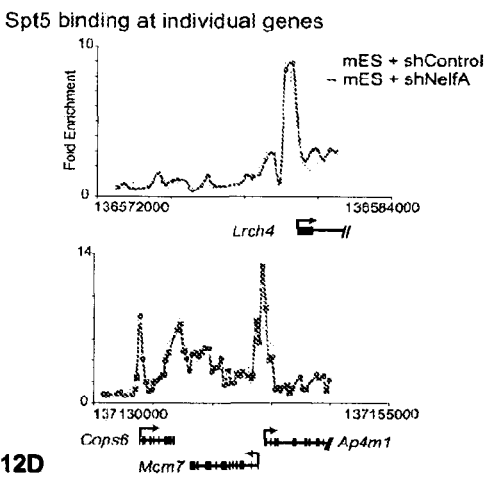
Figure 12D:
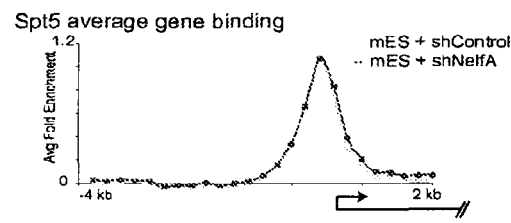
Figure 12E:
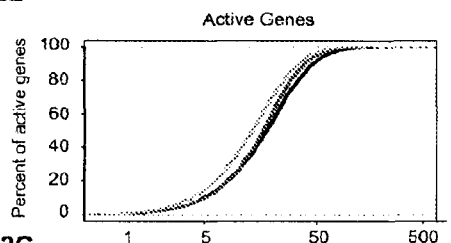
Figure 12F:
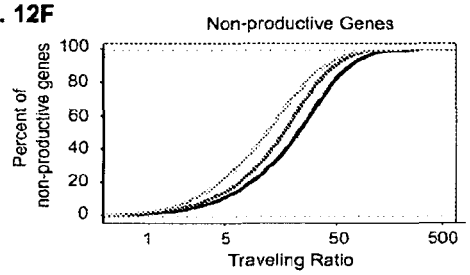

The most significant change in Pol II density was found following Spt5 knockdown, where increases in Pol II density were frequently observed downstream of the promoter at actively transcribed genes (FIG. 4B). At these active genes, depletion of a pausing factor appeared to result in increased transcription through the pause site but because there was little effect on promoter proximal Pol II, high rates of initiation maintained Pol II promoter levels. NelfA was found to continue to occupy the promoter proximal regions following Spt5 knockdown (FIGS. 12A, and 12B). The effects of Spt5 knockdown on Pol II density were quantified using the TR metric (FIGS. 4C, FIGS. 12E, and 12F). There was a substantial shift in TR upon Spt5 knockdown, demonstrating that genes generally experience an increase in Pol II density in the transcribed region at active genes when the levels of DSIF are reduced. These results confirm that Spt5 function contributes to the control of promoter-proximal Pol II in mES cells.

Figure 12G:
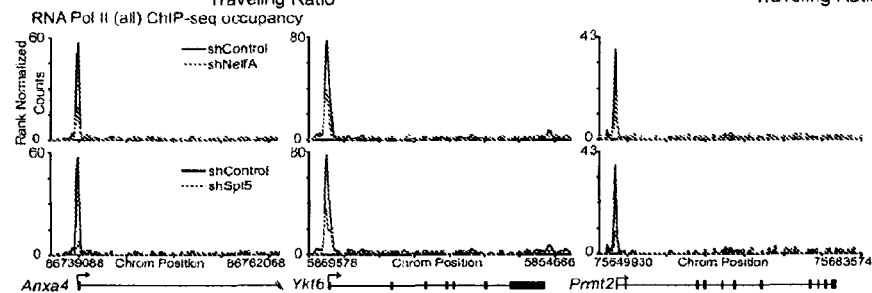

NelfA knockdown had less impact on Pol II occupancy (FIGS. 4B, and 4C), but a modest effect was observed at some genes and the pattern of change was similar to that observed for the Spt5 knockdown experiment at non-productive genes, as evidenced by the change in TR (FIGS. 12E, 12F, and 12G). This result is similar to that observed previously in *Drosophila* embryos, where a fraction of genes showed a loss of Pol II density at the promoter (Muse et al., 2007). Spt5 occupancy was largely unaffected in the promoter proximal regions following NelfA knockdown (FIGS. 12C, and 12D). In summary, we find that Spt5 knockdown, and to a more limited extent NelfA knockdown, can produce increased Pol II occupancy in transcribed regions relative to promoter proximal regions, consistent with the proposed roles of these factors in controlling promoter-proximal pausing.

Example 5 c-Myc Binds P-TEFb and Contributes to Pause Release in ES Cells

Certain DNA binding transcription factors may be responsible for recruiting P-TEFb to release paused polymerase at active genes if P-TEFb-dependent pause release is a general feature of transcription by Pol II. There is evidence that the transcription factor c-myc can bind P-TEFb and stimulate elongation at specific genes in tumor cells (Eberhardy and Farnham, 2001, 2002; Gargano et al., 2007; Kanazawa et al., 2003). Because c-Myc is a key ES cell transcription factor (Cartwright et al., 2005), which occupies a third of active genes (see below), we investigated whether c-Myc plays a role in P-TEFb-dependent pause release at the genes it occupies in ES cells.

Figure 5A:
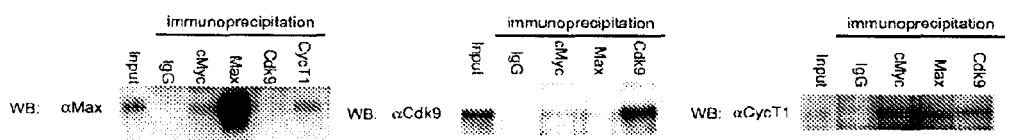
FIG. 5A to 5C. c-Myc target genes are enriched in actively transcribed genes and c-Myc/Max associates with P-TEFb in mES cells. (A) Co-immunoprecipitation experiments in mES cells using antibodies against IgG (to measure background binding), or endogenous c-Myc, Max, Cdk9, and CycT1. Proteins were immunopreipicated from mES cell lysates and analyzed by Western blot analysis by probing for Max, Cdk9 and CycT1. (B) Heatmap representation illustrating the transcriptional state of c-Myc, Oct4, and Nanog target genes in mES cells, as determined by Pol II Ser5P, H3K4me3 (initiation-associated chromatin modification), H3K79me2 (elongation-associated chromatin modification) and H3K27me3 (repressive chromatin modification). Each target gene set was rank ordered based on the amount of Pol II bound at each gene, from the highest amount of Pol II to the lowest amount and the enrichment of the indicated chromatin modification or Pol II is displayed from −2.5 kb to +3 kb surrounding each annotated transcription start site. Blue indicates enrichment and white indicates no enrichment. (C) c-Myc target genes have lower TR values than non-target genes. Histograms were made for the number of genes with a given TR values for high confidence c-Myc target genes and non-target genes. Genes with lower TR values have less pausing than genes with higher TR values.

If c-Myc contributes to P-TEFb-dependent pause release in ES cells, we hypothesized that it might bind P-TEFb in these cells. To function as a transcription factor, c-Myc forms a heterodimer with Max (reviewed in Eilers and Eisenman, 2008). We determined whether endogenous c-Myc/Max interacts with P-TEFb in ES cells using co-immunoprecipitation analysis. We found that immunoprecipitation of P-TEFb components Cdk9 and CycT1 co-immunoprecipitate Max and similarly, immunoprecipitation of c-Myc and Max co-immunoprecipitate Cdk9 and CycT1 (FIG. 5A). Therefore, c-Myc/Max can bind P-TEFb in ES cells.

Figure 5B:
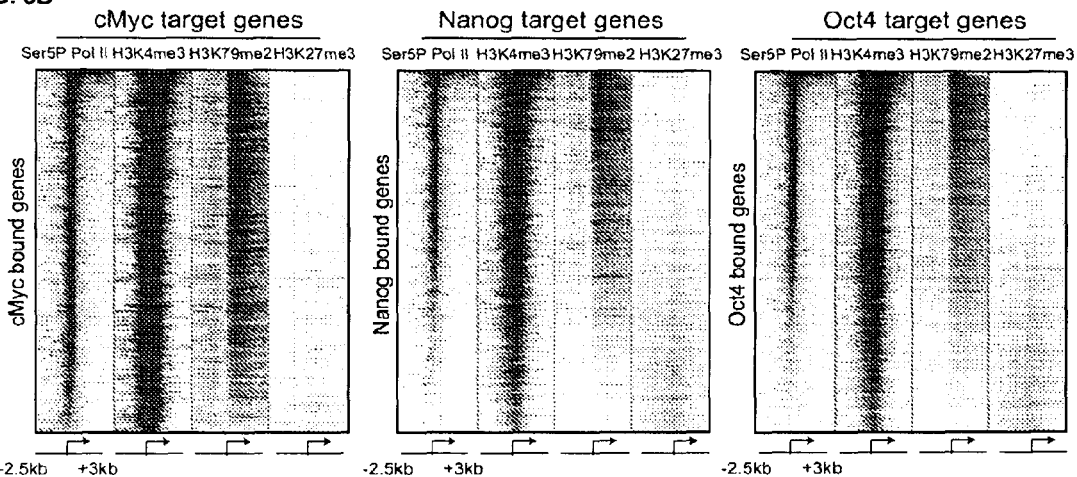
Figure 5C:
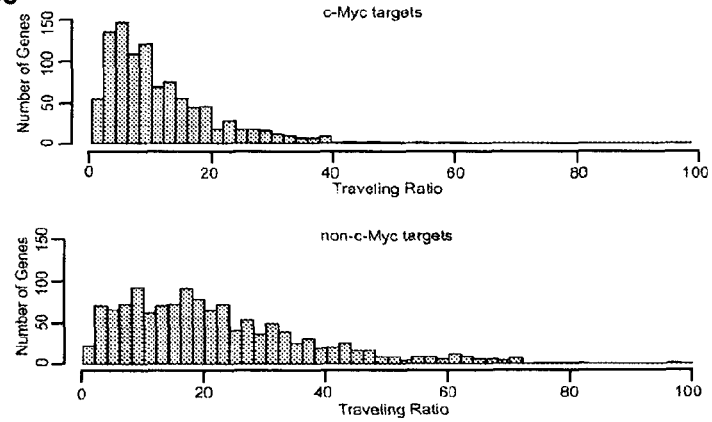

If a predominant function of c-Myc is to contribute to pause release in ES cells, then we expected that it should be associated almost exclusively with actively transcribed genes, unlike other key ES cell regulators like Oct4 and Nanog, which are associated with both active and repressed genes. We examined published ChIP-Seq data to determine the fraction of genes bound by c-Myc, Oct4 and Nanog that were actively transcribed (Chen et al., 2008; Marson et al., 2008), as indicated by the presence of nucleosomes containing histones H3K4me3 and H3K79me2 (FIG. 5B). Just over half of Oct4 and Nanog occupied genes show evidence of transcription elongation, as indicated by the presence of histone H3K79me2. In contrast, almost all of the c-Myc occupied genes have H3K79me2 modified nucleosomes, indicating that the majority of c-Myc targets in mES cells experience transcription elongation. Furthermore, c-Myc target genes have lower TR values (the ratio of Pol II density at promoters versus gene bodies) compared to non c-Myc targets (FIG. 5C). We estimate that 33% of actively transcribed genes in ES cells are bound by c-Myc within 1 kb of the transcriptional start site. The association of c-Myc with a substantial fraction of actively transcribed genes, coupled with evidence that it can bind P-TEFb, is consistent with the model that c-Myc contributes to P-TEFb-dependent pause release at a large portion of active genes in ES cells.

Figure 6A:
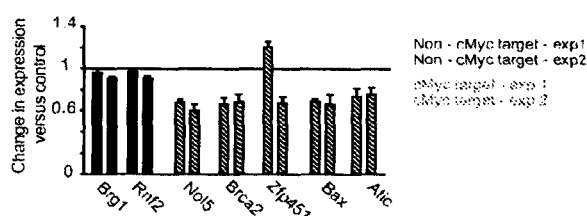
FIGS. 6A to 6E. c-Myc inhibition effects transcription at the pause release step. (A) RNA was extracted from mES cells treated with 10058-F4 or vehicle alone (DMSO) for 6 hours and used to generate cDNA using reverse transcription. Expression change was calculated for 10058-F4 treated cells compared vehicle alone control for two non-c-Myc target genes (Brg1, Rnf2-green) and five c-Myc target genes (Bax, Nol5, Zfp451, Brca2 and Atic—blue) from two independent experiments. Error bars represent s.d. from triplicate qPCR reactions. (B) mES cells were treated with 10058-F4 for either 1.5, 6 or 12 hours. Extracts were analyzed using Western blot using antibodies against Pol II Ser2P CTD, Pol II Ser5P CTD and Cdk9 to determine the levels of the modified forms of Pol II. TBP was used as a loading control. (C) Pol II ChIP-seq binding profiles in mES cells treated with 10058-F4 (c-Myc/Max inhibitor; blue), vehicle alone (black), or flavopiridol (P-TEFb inhibitor; red). Pol II occupancy is shown for three c-Myc target genes (Ncl, Npm1 and Nol5) and two non-cMyc target gene (Txnip and Chpf2). Cells were treated with 10058-F4 or DMSO for 6 hours. See also FIG. 14. (D) Average Pol II binding plots for the high confidence cMyc targets and non-c-Myc target genes in no drug (black), and 10058-F4 treatment (blue). The left panel shows the entire gene average. The right panel is a close up of the transcribed region to show the difference in amounts of elongating Pol II density under the different conditions. Also included in the right panel for comparison is elongating Pol II density following flavopiridol treatment (red). (E) Pol II traveling ratio (TR) as described in FIG. 1C for the high confidence c-Myc target genes and non-c-Myc target genes following 10058-F4 treatment (blue) or no drug (black). The left panel is the TR for the c-Myc targets and right panel is the TR for non-c-Myc targets. Higher TR values indicate a higher degree of pausing in this gene set.
Figure 14A:
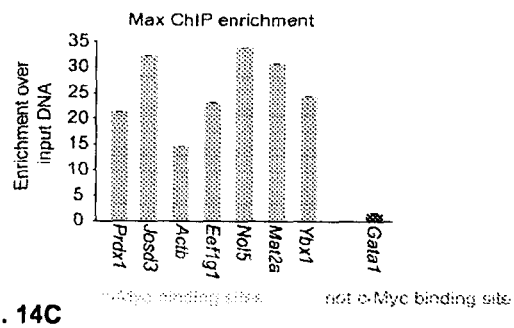
FIGS. 14A to 14F. Max occupies c-Myc binding sites and Pol II occupancy is altered in the transcribed region following c-Myc shRNA knockdown. (A) Max ChIP enrichment in mES cells at seven c-Myc binding sites (Prdx1, Josd3, Actb, Eef1g1, Nol5, Mat2a and Ybx1) and one non c-Myc binding site (Gatal). Max ChIP DNA was analyzed using qPCR at the selected binding sites and enrichment was calculated for replicate PCR reactions over input DNA at each region. This demonstrates that Max binds to c-Myc binding sites in mES cells, consistent with a model where c-Myc and Max heterodimerize and bind the same sites. Error bars represent s.d from duplicate PCR reactions. (B) Protein levels of P-TEFb components Cyclin T1 and Cdk9 with and without 10058-F4 treatment for 6 hours. Protein extracts were analyzed using Western blots and probed with antibodies against CycT1 and Cdk9. TBP was used as a loading control. This analysis demonstrates that the phenotype observed following 10058-F4 treatment (similar to P-TEFb inhibition with flavopiridol) is not a result of decreased levels of P-TEFb. (C) Levels of c-Myc mRNA levels in mES cells infected with sh Control or sh c-Myc shRNA constructs. ES cells were infected for 24 hours, then selected for 72 hours prior to harvesting. c-Myc levels were determined using RT-PCR analysis and normalized against a Gapdh control. (D) Levels of c-Myc protein levels in mES cells infected with sh Control or sh c-Myc shRNA constructs. ES cells were infected for 24 hours, then selected for 72 hours prior to harvesting. c-Myc levels were determined using Western blot analysis using an antibody against c-Myc. Brg1 is used as a loading control. (E) Pol II ChIP-seq binding plots in mES cells with sh Control or sh c-Myc at three c-Myc target genes (Npm1™, Ncl, and Nol5) and two non c-Myc taget genes (Txnip and Nanog). This panel is demonstrating that at these genes c-Myc knockdown has a similar phenotype to 10058-F4 treatment where Pol II density is reduced in the gene body and the density in the promoter proximal region is unaffected. (F) TR analysis on c-Myc target genes in mES cells+sh Control (black) and sh c-Myc (blue), displaying the percent of genes with a given TR. This analysis shows that genes generally become more paused following c-Myc shRNA knockdown, as indicated by the shift in TR to the right.

To more directly test whether c-Myc regulates pause release and the associated Pol II CTD phosphorylation at Ser2, we used a low molecular weight inhibitor of c-Myc/Max, 10058-F4, which inhibits c-Myc/Max heterodimerization both in vitro and in vivo (Hammoudeh et al., 2009; Wang et al., 2007; Yin et al., 2003). Max co-occupies c-Myc binding sites as determined by ChIP, confirming that c-Myc and Max function together at target genes in ES cells (FIG. 14A). Treatment of mES cells with 10058-F4 (50 µM for 6 hours) caused a decrease in the expression of most c-Myc target genes tested, but did not affect the expression of two non-c-Myc target genes, indicating that c-Myc/Max function is inhibited by 10058-F4 under these conditions (FIG. 6A). The magnitude of the decrease observed (~20-40%) is consistent with the relatively short duration of inhibitor treatment relative to typical mRNA half-lives of ~7 hours in mES cells (Sharova et al., 2009).

Figure 6B:
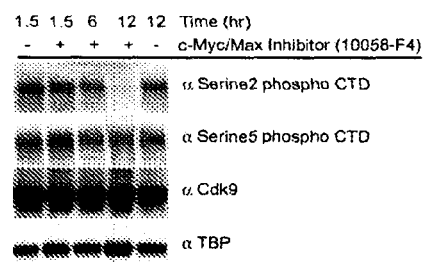

If a key function of c-Myc is to contribute to pause release at the active genes it occupies in ES cells, then loss of c-Myc would be expected to cause a reduction in the levels of Ser2-phosphorylated Pol II (the form associated with elongation), but should not affect the levels of Ser5-phosphorylated Pol II (the form associated with initiation). We found that treatment of ES cells with 10058-F4 did indeed cause a significant reduction in the levels of Pol II Ser2P, while Ser5P remained unaffected (FIG. 6B).

Figure 6C:
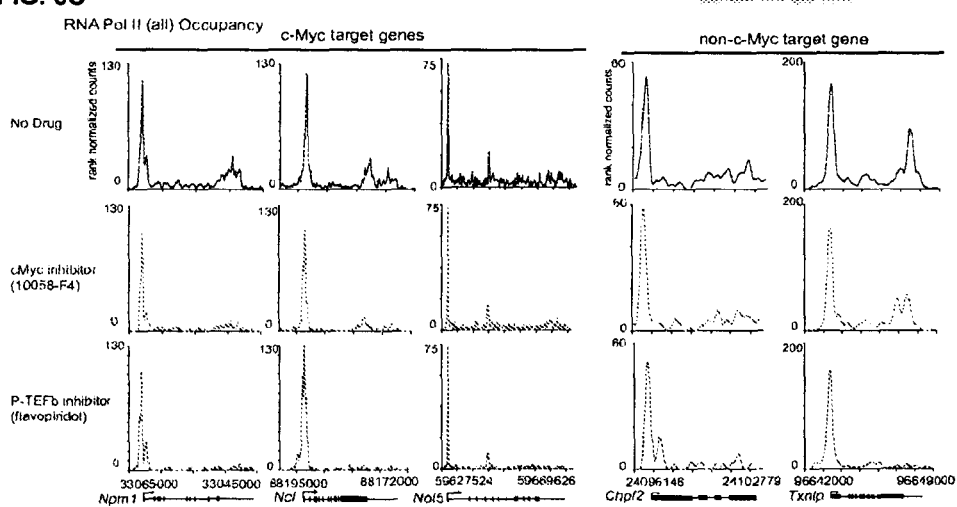
Figure 14B:
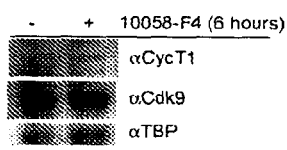
Figure 14C:
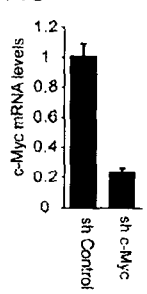
Figure 14D:
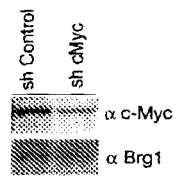
Figure 14E:
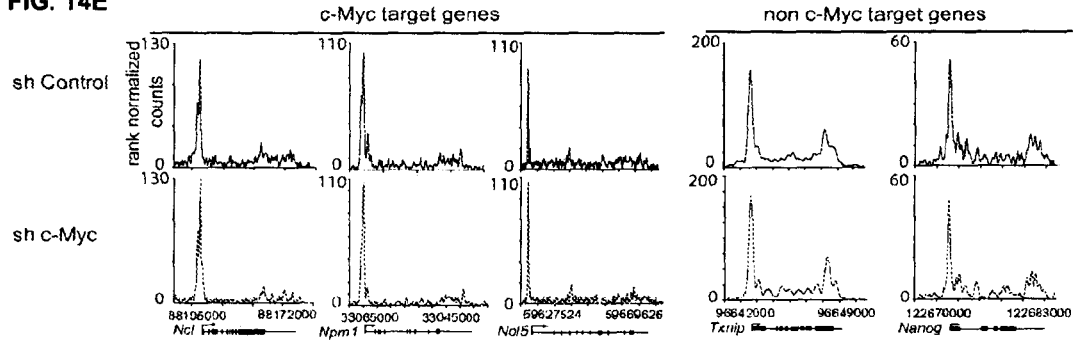

If c-Myc regulates pause release, then inhibition by 10058-F4 should have an effect on Pol II levels in promoter and gene bodies similar to that of flavopiridol, but only at c-Myc occupied genes. We tested this idea by determining how 10058-F4 affects Pol II occupancy using ChIP-seq in mES cells. There was little effect on Pol II density at promoters but there was a clear reduction in transcribed regions (FIG. 6C). This effect on Pol II density was also observed following c-Myc shRNA knockdown (FIG. 14E). The magnitude of the effect with 10058-F4 was somewhat milder than with flavopiridol probably because the inhibition of c-Myc/Max heterodimerization is not complete (Hammoudeh et al., 2009; Wang et al., 2007; Yin et al., 2003). Treatment with 10058-F4 did not alter the protein levels of P-TEFb components Cdk9 or CycT1, indicating that this effect is not a result of reduced levels of P-TEFb (FIG. 14B). Importantly, genes that lack evidence of c-Myc binding showed patterns of Pol II occupancy that were unaffected by treatment with 10058-F4 (FIG. 6C). We confirmed that genes that are not targets of c-Myc do require P-TEFb function to release paused Pol II by showing that flavopiridol treatment causes a block in pause release (FIG. 6C, right panels), which suggests that transcription factors other than c-Myc are involved in recruiting P-TEFb to stimulate pause release at these genes.

Figure 6D:
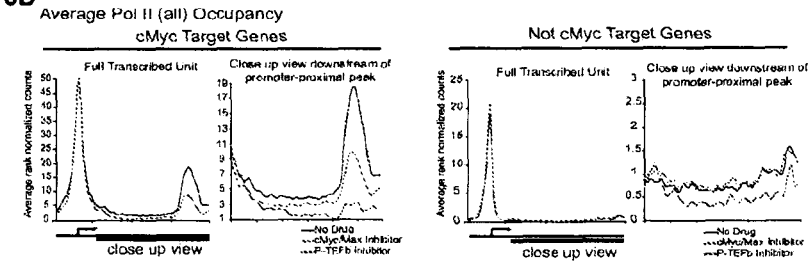
Figure 6E:
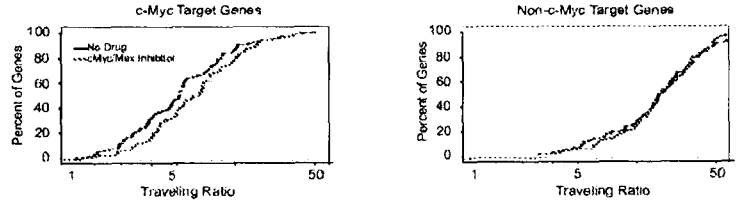
Figure 14F:
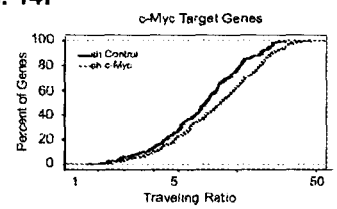

We carried out a more global analysis of the effect of 10058-F4 on Pol II occupancy of genes bound by c-Myc and compared these patterns to genes that are not bound by this factor but show evidence of elongation (FIG. 6D). The results show that high-confidence c-Myc target genes generally retained promoter-proximal Pol II but had reduced Pol II density in their transcribed regions, whereas Pol II occupancy does not change at genes that are not c-Myc targets (FIG. 6D). Further analysis confirmed that there were statistically significant changes in the gene body (p=7.341e-06) but not the promoter region (p=0.4536) of c-Myc targets (see Methods). Additionally, following 10058-F4 treatment a substantial increase in TR was observed at c-Myc target genes, but no such shift was observed at non-c-Myc targets (FIG. 6E). A similar shift in TR at the c-Myc target genes was also detected following c-Myc shRNA knockdown, indicating genes become more paused (FIG. 14F). The observation that reduced c-Myc activity had little effect on the levels of promoter-proximal Pol II but caused a reduction in the levels of Pol II across transcribed portions of c-Myc target genes is consistent with the model that c-Myc/Max generally plays a role in Pol II pause release at targets genes in mES cells.

Example 6

Loss of Oct4 and c-Myc have Different Effects on Pol II Gene Occupancy

Figure 7A:
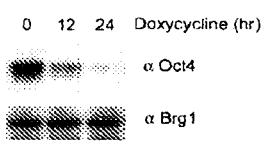
FIGS. 7A to 7C. Oct4 shutdown reduces Pol II initiation at Oct4-dependent genes. (A) Oct4 protein levels in ZHBTc4 (doxycycline-inducible Oct4 knockdown cells) mES cells following 0, 12 or 24 hours of doxycycline treatment. Extracts were probed with antibodies against Oct4 and Brg1 was used as a loading control. (B) Pol II ChIP-seq binding profiles in ZHBTc4 mES cells at Oct4 target genes following the indicated time of doxycycline treatment, inducing Oct4 knockdown. Of note, the Oct4 bound genes change Pol II occupancy in both the promoter proximal region and the transcribed region. The panel to the right shows Pol II ChIP-seq binding profiles at non-Oct4 target genes in ZHBTc4 mES cells following the indicated time of doxycycline treatment, inducing Oct4 knockdown. (C) Pol II traveling ratio (TR) as described in FIG. 1C for the high confidence Oct4-dependent genes and Oct4 non-target genes in ZHBTc4 cells after either 0 or 12 hrs of doxycycline treatment. The left panel is the TR for the Oct4 targets and right panel is the TR for non-Oct4 targets.
Figure 7B:
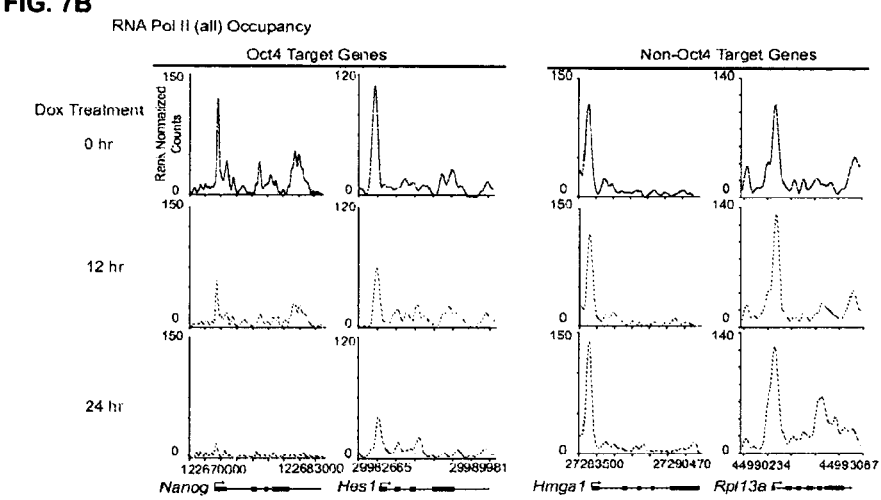
Figure 7C:
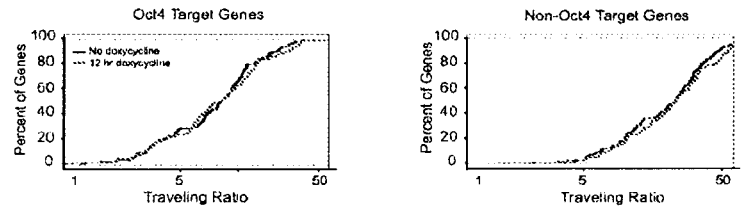

Loss of another key ES cell transcription factor, Oct4, leads to reduced transcription of many Oct4-bound active genes in ES cells (Hall et al., 2009; Matoba et al., 2006; Niwa et al., 2000). To determine how loss of Oct4 affects Pol II levels at the promoters and transcribed regions of its target genes, we utilized a doxycycline-inducible Oct4 shutdown mES cell line (Niwa et al., 2000) and monitored Pol II levels genome-wide by ChIP-Seq before and after Oct4 shutdown (FIG. 7). Oct4 protein levels were substantially reduced within 12 hrs and were nearly eliminated at 24 hrs after exposure to doxycycline (FIG. 7A). At Oct4-occupied genes that experience reduced transcription, Pol II occupancy was generally reduced in both the promoter proximal region and the gene body at 12 and 24 hrs (FIG. 7B). These effects were not observed at most genes that are not occupied by Oct4 (FIG. 7B). The loss of Pol II in the promoter-proximal regions of Oct4 target genes, given the commensurate loss of Pol II in the gene body, is likely due to reduced recruitment of the transcription apparatus. For these Oct4 target genes, where Pol II is lost from both promoter proximal and gene body regions, we would expect no change in TR, and a global analysis of such genes revealed that this is indeed the case (FIG. 7C). We conclude that the pattern of reduced Pol II density at Oct4 target genes that occurs upon loss of Oct4 differs from that at c-Myc target genes upon loss of c-Myc, and suggest that this is due to differences in the stage at which the two transcription factors play their dominant regulatory roles.

The Examples above describe several lines of evidence supporting the contention that promoter-proximal pausing is a general feature of transcription by Pol II in ES cells. First, genome-wide analysis shows that the bulk of Pol II occupies the promoter proximal region of genes, even when these genes are among the most actively transcribed in the cell. Second, the pause factors DSIF and NELF typically co-occupy these sites with Pol II, consistent with the idea that they generally bind to the enzyme during early steps of transcription elongation. Third, inhibition of the pause-release factor P-TEFb prevents release of promoter proximal paused Pol II at essentially all genes.

The model that promoter proximal pausing is general has several implications for transcriptional control. A step subsequent to recruitment of the transcription initiation apparatus can, in principle, be regulated at any gene. Promoter proximal pausing may facilitate assembly of RNA processing factors and may couple transcription and mRNA processing events. DSIF and Ser5P Pol II can bind capping enzyme and stimulate mRNA capping. Ser2 phosphorylation by P-TEFb leads to splicing and 3' end processing factor recruitment to genes and is required for proper processing. Promoter-proximal pausing also provides a mechanism to control transcription from bidirectional promoters, perhaps facilitating the formation of nucleosome-depleted regions and thus providing improved access to regulators.

As described herein, multiple lines of evidence support the contention that c-Myc/Max generally plays a role in Pol II pause release at its target genes in ES cells, and does so through recruitment of P-TEFb. Loss of c-Myc reduces the levels of elongating Pol II but does not affect the levels of promoter-proximal Pol II. Inhibition of c-Myc/Max function leads to a substantial reduction in the levels of Ser2-phosphorylated Pol II in cells, which is the form associated with elongation, but does not affect the levels of Ser5-phosphorylated Pol II, which is the form associated with initiation. cMyc binds P-TEFb, which is responsible for Ser2-phosphorylated Pol II. Consistent with a role in pause release, c-Myc is associated almost exclusively with genes that are actively transcribed, unlike other key ES cell regulators like Oct4 and Nanog, which occupy both active and repressed genes. Furthermore, c-Myc occupies promoter-proximal sites (FIG. 13B), which are heavily enriched for the E-box core motif that it binds (FIG. 13C), where c-Myc would be optimally positioned to recruit P-TEFb.

Experimental Procedures mES Cell Culture

V6.5 (C57BL/6-129) murine ES cells were grown under typical mES conditions on irradiated mouse embryonic fibroblasts (MEFs). For location analysis, cells were grown for two passages off of MEFs, on gelatinized tissue-culture plates. For location analysis on mES cells following treatment with small molecule inhibitors, cells were grown two passages off feeders and prior to formaldehyde crosslinking, the cells were treated by addition of the indicated final concentration of flavopiridol (1 µM for 1 hour for ChIP-chip and ChIP-seq experiments, or the indicated concentration and time for Western blot analysis), or c-Myc/Max inhibitor 10058-F4 (50 µM for 6 hours), both dissolved in DMSO, to the growth medium. As a control, vehicle alone (DMSO) was added to the growth medium at the same final volume as with drug. Small molecule inhibitors used were: Flavopiridol (Sigma cat #F3055), and c-Myc inhibitor 10058-F4 (Sigma cat #F3680). For location analysis following shRNA knockdown (OpenBiosystems), viral media was collected 48 hours after co-transfection (in 293T cells) and the V6.5 mES cells were directly infected with the viral media 24 hours after initial plating of the mES cells. The infection media was 1:2 viral media:mES cell media with 2 mM polybrene. The efficiently infected cells were selected for 24 hours post infection with mES cell media containing 2 µM puromycin. V6.5 cells were cross-linked 72 hours post selection and frozen for ChIP-Seq experiments and western blotting. For location analysis following Oct4 shutdown, ZHBTc4 mES cells (Niwa et al., 2000) were grown under standard mES cell culture conditions and expanded for two passages off MEF feeders. ES cell culture media with 2 µg/ml doxycycline was added to the cells for 0 hours, 12 hours and 24 hours prior to formaldehyde crosslinking.

Chromatin Immunoprecipitation (ChIP)

ChIP was done following the Agilent Mammalian ChIP-on-chip protocol (version 9.1, November 2006). The antibodies and ChIP conditions used can be found in the Supplemental Information. For ChIP-chip analysis, Cy3- and Cy5-labeled ligation mediated PCR products were hybridized to a 44,000 feature Agilent mouse microarray. For ChIP-seq analysis, Solexa/Illumina sequencing and analysis was done following the protocol described in Marson et al. 2008. Refer to the Supplemental Information for a detailed description of these methods.

Active and Non-Productive Gene Classes in mES Cells

The active and non-productive genes were classified in mES cells using H3K4me3 (initiation-associated chromatin modification) and H3K79me2 (elongation-associated chromatin modification), as determined by ChIP-seq (Marson et al. 2008), as markers of transcriptional state. Active genes with both H3K4me3 and H3K79me2 chromatin modifications, non-productive genes had only H3K4me3 and inactive genes did not have H3K4me3 or H3K79me2 chromatin modifications (Guenther et al., 2007; Marson et al., 2008; Morillon et al., 2005; Pokholok et al., 2005; Schubeler et al., 2004).

Traveling Ratio Calculation

Pol II levels peak in the 5' region of many genes. To quantify this effect, we have developed a measure called Traveling Ratio (TR) that compares the ratio between Pol II density in the promoter and in the gene region. We defined the promoter region from −30 to +300 relative to the TSS and the gene body as the remaining length of the gene. See also FIG. 9 and FIG. 15.

Heatmap Analysis of ChIP-seq Data

ChIP-seq enrichment for the indicated factor or modification was determined in 50 bp bins (enrichment in the bin as counts per million), centered on each transcriptional start site. Generally, the gene list for each representation was rank ordered based on the amount of Pol II (all) in mES cells, from most to least to correlate the enrichment of the given factor with the amount of Pol II at each gene. Cluster 3.0 (http://bonsai.ims.u-tokyo.ac.jp/~mdehoon/software/cluster/software.htm) and Java Treeview (www.jtreeview.sourceforge.ne) were used to visualize the data and generate figures shown herein.

Previously Published ChIP-seq Datasets Used in this Study

H3K4me3, H3K79me2, and Oct4 occupancy in mES cells (Marson et al., 2008); Nanog and c-Myc occupancy in mES cells (Chen et al., 2008); and H3K27me3 occupancy in mES cells (Mikkelsen et al., 2007).

The Following ChIP-seq Datasets were Generated for this Work as Described Herein:

RNAPolII_Phosphorylation_Tracks.WIG.gz—contains three ChIP-seq datasets mapped to mouse genome mm8 using a +200 bp extension model that can be uploaded to the UCSC genome browser to view binding events (http://genome.ucsc.edu/). The datasets include Pol II Ser5P in wildtype V6.5 mES cells, Pol II Ser2P in wildtype V6.5 mES cells, and Pol II (all) in wildtype V6.5 mES cells+shControl. Enrichment is shown as counts per million reads in 25 bp genomic bins and the track floor is at 1 count per million reads. Additional tracks identify genomic regions that have been determined enriched above background at the given p value.

Factor_Tracks.WIG.gz—contains three ChIP-seq datasets mapped to mouse genome mm8 using a +200 bp extension model that can be uploaded to the UCSC genome browser to view binding events. The datasets include Spt5, NelfA, and Ctr9 in wildtype V6.5 mES cells. Enrichment is shown as counts per million reads in 25 bp genomic bins and the track floor is at 1 count per million reads. Additional tracks identify genomic regions that have been determined enriched above background at the given p value.

RNAPolII_PauseFactorKnockdown_Tracks.WIG.gz—contains three ChIP-seq datasets mapped to mouse genome mm8 using a +200 bp extension model that can be uploaded to the UCSC genome browser to view binding events. The ChIP experiments were done using the N20 Pol II antibody (sc-899).to determine total Pol II occupancy. The datasets include Pol II (all) mES V6.5+shSpt5, Pol II (all) in mES V6.5+shNelfA, and Pol II (all) mES V6.5+shControl. Binding enrichment tracks for all datasets are shown as rank normalized counts in 25 bp genomic bins and the track floor is at 2 count per million reads. Rank normalized data is indicated with the title of the track (title of the track is, for example, mES_Pol2_shControl_norm). Additional tracks identify genomic regions that have been determined enriched above background at the given p value.

RNAPolII_FlavopiridolTreated_Tracks.WIG.gz—contains two ChIP-seq datasets mapped to mouse genome mm8 using a +200 bp extension model that can be uploaded to the UCSC genome browser to view binding events. The ChIP experiments were done using the N20 Pol II antibody (sc-899) to determine total Pol II occupancy. The datasets include Pol II (all) in mES V6.5+DMSO control, and Pol II (all) in mES V6.5+flavopiridol (P-TEFb inhibitor). In these experiments, cells were treated with either flavopiridol (1 μM) or DMSO alone for 60 minutes prior to crosslinking and ChIP with Pol II antibody. Binding enrichment tracks for all datasets are shown as rank normalized counts in 25 bp genomic bins and the track floor is at 2 count per million reads. Rank normalized data is indicated with the title of the track (title of the track is, for example, mES_Pol2_Flavo_norm). Additional tracks identify genomic regions that have been determined enriched above background at the given p value.

RNAPolII_10058F4Treated_Tracks.WIG.gz—contains two ChIP-seq datasets mapped to mouse genome mm8 using a +200 bp extension model that can be uploaded to the UCSC genome browser to view binding events. The ChIP experiments were done using the N20 Pol II antibody (sc-899) to determined total Pol II occupancy. The datasets include Pol II (all) in mES V6.5+DMSO control, and Pol II (all) in mES V6.5+10058-F4 (c-Myc/Max inhibitor). In these experiments, cells were treated with either 10058-F4 (500M) or DMSO alone for 6 hours prior to crosslinking and ChIP with Pol II antibody. Binding enrichment tracks for all datasets are shown as rank normalized counts in 25 bp genomic bins and the track floor is at 2 count per million reads. Rank normalized data is indicated with the title of the track (title of the track is, for example, mES_DMSO_norm). Additional tracks identify genomic regions that have been determined enriched above background at the given p value.

RNAPolII_cMycKnockdown_Tracks.WIG.gz—contains two ChIP-seq datasets mapped to mouse genome mm8 using a +200 bp extension model that can be uploaded to the UCSC genome browser to view binding events. The ChIP experiments were done using the N20 Pol II antibody (sc-899) to determine total Pol II occupancy. The datasets include Pol II (all) mES V6.5+shc-Myc and Pol II (all) mES V6.5+shControl. Binding enrichment tracks for all datasets are shown as rank normalized counts in 25 bp genomic bins and the track floor is at 2 count per million reads. Rank normalized data is indicated with the title of the track (title of the track is, for example, mES_Pol2_shControl_norm). Additional tracks identify genomic regions that have been determined enriched above background at the given p value.

RNAPolII_Oct4Shutdown_Tracks.WIG.gz—contains two ChIP-seq datasets mapped to mouse genome mm8 using a +200 bp extension model that can be uploaded to the UCSC genome browser to view binding events. The ChIP experiments were done using the N20 Pol II antibody (sc-899) to determine total Pol II occupancy. The datasets include Pol II (all) mES ZHBTc4+doxycycline 0 hours, Pol II (all) mES ZHBTc4+doxycycline 12 hours, and Pol II (all) mES ZHBTc4+doxycycline 24 hours. Binding enrichment tracks for all datasets are shown as rank normalized counts in 25 bp genomic bins and the track floor is at 2 count per million reads. Rank normalized data is indicated with the title of the track (title of the track is, for example, mES_Pol2_Dox0 hr_norm). Additional tracks identify genomic regions that have been determined enriched above background at the given p value.

| Dataset | total number of unique reads used for analysis |
| --- | --- |
| Pol II Ser5P | 3543456 |
| Pol II Ser2P | 10231400 |
| Spt5 | 4639835 |
| NelfA | 3406514 |
| Ctr9 | 4672291 |
| Pol II (all) sh Control | 5156732 |
| Pol II (all) sh NelfA | 3785780 |
| Pol II (all) sh Spt5 | 3369501 |
| Pol II (all) DMSO control | 1991231 |
| Pol II (all) flavopiridol-treated | 3001750 |
| Pol II (all) DMSO control (for 10058-F4 experiment) | 6320713 |
| Pol II (all) 10058-F4-treated | 4429350 |
| Pol II (all) sh Control (for sh c-Myc) | 6027028 |
| Pol II (all) sh c-Myc | 7031951 |
| Pol II (all) 0 hr doxycyclin (ZHBTc4 cells) | 9820076 |
| Pol II (all) 12 hr doxycyclin (ZHBTc4 cells) | 9211878 |
| Pol II (all) 24 hr doxycyclin (ZHBTc4 cells) | 7392695 |

Table S1. Total number of reads for each chip-seq dataset. A list of the total number Of chip-seq mapped reads used from each dataset for analysis in this study.

| | Number of Genes | Number of Genes with TR > 2 | Number of Genes with TR < 2 |
| --- | --- | --- | --- |
| Pol II bound | 11456 | | |
| Pol II bound with H3K79me2 (active) | 6842 | 6252 | 590 |
| Pol II bound without H3K79me2 (non-productive) | 4614 | 4184 | 430 |
| Inactive | 10407 | NA | NA |

Table S2. Number of genes classified as active, non-productive and inactive. This table lists the number of genes in each gene class (active, non-productive and inactive). 21865 total RefSeq genes were used for this analysis. Active genes are bound by Pol II and H3K79me2 (marker of elongation), non-productive genes are bound by Pol II but not H3K79me2 and inactive genes are not bound by either. Binding is determined at p=1e-9, a stringent cutoff to minimize false positives. In FIG. 1c, we determine that approximately 91% of genes have a TR greater than 2 and 9% of genes had a TR less than or equal to 2. We list the number of genes in each of these classes as they fall into the active and non-productive gene classes.

Table s3 (data not shown). Enriched genes, at 1E-9, for each ChIP-seq dataset. Please see FIGS. 1, 2, 3, 4, 5, 6 and 7. List of the genes tested for enrichment for each ChIP-seq dataset. 1 denotes enriched over background and 0 denotes not enriched at 1e-9 over background. Binding is determined at p=1e-9, a stringent cutoff to minimize false positives. Enrichment was determined 1000 bp upstream or downstream of each transcriptional start site. The genomic coordinates refer to mouse genome build mm8 The minimum enrichment for calling a bound region is 5 fold enriched over background reads with a statistical significance of p=1e-9.

Table s4 (data not shown). ChIP-seq enriched regions, at 1e-9, for each factor. Please see FIGS. 1, 2, 3, and 4. List of the regions enriched above background for each factor where the enriched region start and enriched region end is listed. The genomic coordinates correspond to mouse genome build mm8. The minimum enrichment for calling an enriched region is 5 fold enriched over background at a statistical significance of p=1e-9, a stringent cutoff to minimize false positives. Additionally, the nearest transcript is listed, if it is within 1000 bp of the enriched region. The enriched region for each factor is represented as separate tabs in the excel file. See also, Rahl P B, et al., c-Myc regulates transcriptional pause release. *Cell.* 141(3):432-45, 2010, and its supplemental information and tables, incorporated herein by reference.

Supplemental Experimental Procedures mES Cell Culture

V6.5 (C57BL/6-129) murine ES cells were grown under typical mES conditions on irradiated mouse embryonic fibroblasts (MEFs). In summary, cells were grown on gelatinized tissue culture plates in Dulbecco's modified Eagle medium supplemented with 15% fetal bovine serum (characterized from Hyclone), 1000 U/ml leukemia inhibitory factor (LIF, Chemicon; ESGRO ESG1106), non-essential amino acids, L-glutamine, Penicillin/Streptomycin and β-mercaptoethanol. For location analysis, cells were grown for two passages off of MEFs, on gelatinized tissue-culture plates. Mouse embryonic fibroblasts were prepared and cultured from DR-4 strain mice.

For location analysis following Spt5 and NelfA knockdown, shRNA plasmids targeting the mouse Spt5 and NelfA mRNAs and an empty plasmid (control) (Open Biosystems, Huntsville, Ala. RMM4534-NM_013676, RMM4534-NM_011914, and RMM4534_NM_010849, RHS4080) were used. We purchased and tested each set of shRNA hairpins for ability of each hairpin to knockdown the mRNA of the factor of interest. We then selected the hairpin that performed the best for use in ChIP-seq analysis. For Spt5, hairpin TRCN0000092761 was used. For NelfA, hairpin TRCN0000124874 was used. For c-Myc, hairpin TRCN0000042516 was used. 293T cells were plated in 6-well dishes at 6×10^5 cells/well. The shRNA plasmids and lentiviral components were co-transfected into 293T cells. V6.5 mES cells were plated in T-75 flasks at 2×10^6 cells/flask. Viral media was collected 48 hours after co-transfection and the V6.5 mES cells were directly infected with the viral media 24 hours after initial plating of the mES cells. The infection media was 1:2 viral media:mES cell media with 2 mM polybrene. The efficiently infected cells were selected for 24 hours post infection with mES cell media containing 2 μM puromycin. V6.5 cells were cross-linked 72 hours post selection and frozen for ChIP-Seq experiments and western blotting. To assess mRNA knockdown a small fraction of cells were collected and mRNA was prepared (using a Qiagen RNeasy Mini Kit, Qiagen, Valencia, Calif.). RT-qPCR was used to determine relative gene expression between mock knockdown and shRNA knockdown samples. Taqman gene expression assays from Applied Biosystems, Foster City, Calif. were ordered for the Spt5, NelfA, and GAPDH (control) genes (Mm01217228_m1, Mm01170629_m1, Mm99999915_g1, Mm00487804_m1). Western blot analysis (described below) was done to assess knockdown at the protein level prior to ChIP-seq analysis. c-Myc knockdown was also assessed at the mRNA level (described below) using RT-PCR. For location analysis on mES cells following treatment with small molecule inhibitors, cells were grown two passages off feeders and prior to formaldehyde crosslinking, the cells were treated by addition of the indicated final concentration of flavopiridol (1 μM for 1 hour for ChIP-chip and ChIP-seq experiments, or the indicated concentration and time for Western blot analysis), or c-Myc/Max inhibitor 10058-F4 (50 μM for 6 hours for ChIP-seq experiments or the indicated time for Western blot analysis), both dissolved in DMSO, to the growth medium. 50 μM is within the concentration range commonly used for 10058-F4 in vivo to investigate c-Myc function (Arabi et al., 2005; Fang et al., 2008; Faumont et al., 2009; Follis et al., 2008; Hammoudeh et al., 2009; Khanna et al., 2009; Lee et al., 2009; Sampson et al., 2007; Wang et al., 2007). As a control, vehicle alone (DMSO) was added to the growth medium at the same final volume as with drug. Small molecule inhibitors used were: Flavopiridol (Sigma cat #F3055), and c-Myc inhibitor 10058-F4 (Sigma cat #F3680). For location analysis following Oct4 shutdown, ZHBTc4 mES cells (Niwa et al., 2000) were grown under standard mES cell culture conditions and expanded for two passages off MEF feeders. ES cell culture media with 2 µg/ml doxycycline was added to the cells for 0 hours, 12 hours and 24 hours prior to formaldehyde crosslinking Loss of Oct4 was assessed using Western Blot analysis (see below). Oct4 protein was essentially depleted at the 24 hour time point and we noticed that the cells appeared morphologically different from mES cells and the 0 hr and 12 hr time points. It is well established that loss of Oct4 causes ES cell differentiation. Therefore, in order to minimize measuring secondary effects, we performed our TR analysis on Oct4 targets and non-targets on the earliest time points: 0 hr and 12 hr following doxycycline treatment.

Chromatin Immunoprecipitation (ChIP)

ChIP was done following the Agilent Mammalian ChIP-on-chip protocol (version 9.1, November 2006). In summary, mES cells were grown as described above and cross-linked for 15 minutes at room temperature by the addition of one-tenth of the volume of 11% formaldehyde solution (11% formaldehyde, 50 mM Hepes pH 7.3, 100 mM NaCl, 1 mM EDTA pH 8.0, 0.5 mM EGTA pH 8.0) to the growth media followed by two washes with PBS. Cells were scraped and frozen in liquid nitrogen. 100u1 of Dynal magnetic beads (Sigma) were blocked with 0.5% BSA (w/v) in PBS. Magnetic beads were bound with 10 ug of the indicated antibody. Antibodies used are as follows: Pol II (all; Rpb1 N-terminus): Santa Cruz sc-899; Ser5P Pol II: Abcam ab5131; Ser2P Pol II: Abcam (H5 clone) ab24758 with Upstate IgG-IgM linker antibody 12-488; Spt5: gift from Yuki Yamaguchi and Hiroshi Handa (Wada et al., 1998); NelfA: Santa Cruz (A-20) sc-23599; Ctr9: Bethyl labs A301-395; and Max: Santa Cruz sc-197. For all of the experiments analyzing Pol II occupancy following shRNA-mediated knockdown, flavopiridol, or 10058-F4 treatment, the Pol II (all; Santa Cruz sc-899, Pol II N-20) antibody was used. Crosslinked cells were lysed with lysis buffer 1 (50 mM Hepes pH 7.3, 140 mM NaCl, 1 mM EDTA, 10% glycerol, 0.5% NP-40, and 0.25% Triton X-100) and washed with lysis buffer 2 (10 mM Tris-HCl pH 8.0, 200 mM NaCl, 1 mM EDTA pH 8.0 and 0.5 mM EGTA pH 8.0).

For Spt5 ChIPs, cells were resuspended and sonicated in lysis buffer 3 (10 mM Tris-HCl pH 8.0, 100 mM NaCl, 1 mM EDTA pH 8.0, 0.5 mM EGTA pH 8.0, 0.1% Na-Deoxycholate and 0.5% N-lauroylsarcosine) for 8 cycles at 30 seconds each on ice (18 watts) with 60 seconds on ice between cycles. Triton X-100 was added to a final concentration of 1% to the sonicated lysates. Sonicated lysates were cleared and incubated overnight at 4° C. with magnetic beads bound with antibody to enrich for DNA fragments bound by the indicated factor. Beads were washed four times with RIPA (50 mM Hepes pH 7.3, 500 mM LiCl, 1 mM EDTA, 1% NP-40 and 0.7% Na-Deoxycholate) and once with TE+50 mM NaCl. Bound complexes were eluted in elution buffer (50 mM Tris-HCl pH 8.0, mM EDTA pH 8.0, 1% SDS) at 65° C. for 15 minutes with occasional vortexing. Cross-links were reversed overnight at 65° C. RNA and protein were digested using RNAse A and Proteinase K, respectively and DNA was purified with phenol chloroform extraction and ethanol precipitation.

For Pol II Ser5P, Pol II (all), NelfA, Ctr9 and Max ChIPs, cells were resuspended and sonicated in sonication buffer (50 mM Tris-HCl pH 7.5, 140 mM NaCl, 1 mM EDTA, 1 mM EGTA, 1% Triton X-100, 0.1% Na-deoxycholate, 0.1% SDS) for 8 cycles at 30 seconds each on ice (18 watts) with 60 seconds on ice between cycles. Sonicated lysates were cleared and incubated overnight at 4° C. with magnetic beads bound with antibody to enrich for DNA fragments bound by the indicated factor. Beads were washed three times with sonication buffer, one time with sonication buffer with 500 mM NaCl, one time with LiCl wash buffer (20 mM Tris pH 8.0, 1 mM EDTA, 250 mM LiCl, 0.5% NP-40, 0.5% Na-deoxycholate) and one time with TE. DNA was eluted in elution buffer. Cross-links were reversed overnight. RNA and protein were digested using RNAse A and Proteinase K, respectively and DNA was purified with phenol chloroform extraction and ethanol precipitation.

For Pol II Ser2P ChIP, cells were resuspended and sonicated in sonication buffer II (50 mM Tris-HCl pH 7.5, 140 mM NaCl, 1 mM EDTA, 1 mM EGTA, 1% Triton X-100, 0.1% Na-deoxycholate, 0.1% SDS) for 8 cycles at 30 seconds each on ice, at 18 watts with 60 seconds on ice between cycles. Sonicated lysates were cleared and incubated overnight at 4° C. with magnetic beads bound with antibody to enrich for DNA fragments bound by Pol II Ser2P. Beads were washed two times with sonication buffer II, one time with LiCl wash buffer (2 mM Tris pH 8.0, 0.02 mM EDTA, 50 mM LiCl, 0.1% NP-40, 0.1% Na-deoxycholate) and one wash with TE. DNA was eluted in elution buffer. This protocol is similar to that used in (Stock et al., 2007). Cross-links were reversed overnight. RNA and protein were digested using RNAse A and Proteinase K, respectively and DNA was purified with phenol chloroform extraction and ethanol precipitation.

ChIP-PCR Analysis

Max ChIP DNA was analyzed using SYBR Green real-time PCR analysis (Applied Biosystems). Fold enrichment was determined from replicate PCR reactions at seven c-Myc binding sites (Prdx1, Josd3, Actb, Eef1g1, No15, Mat2a, Ybx1) and one non-c-Myc binding site (Gata1), as determined by previously published c-Myc ChIP-seq (Chen et al., 2008), over input DNA. The oligos used for this analysis are:

```
Prdx1 fwd:
ttagttcccggacctgttg

Prdx1 rev:
acaaactcgtcccaccaag

Josd3 fwd:
cctggagggcgtttttagt

Josd3 rev:
acccttcggaacgtaacc

Actb fwd:
gatcactcagaacggacacc

Actb rev:
acacgctaggcgtaaagttg

Eef1g1 fwd:
CTGGGTCTCCATTGTCTGG

Eef1g1 rev:
AGTTCCACCAACCTGCTCA

No15 fwd:
GGCTCCGAAAAGATGTGAA
```

-continued

```
No15 rev:
AGCAGAGGTCGCCCTAAAT

Mat2a fwd:
GTCTCCGAAGGTCCCATCT

Mat2a rev:
TGAAGGCTAAAGGGCATGT

Ybx1 fwd:
AGATCCTGGACCGACTTCC

Ybx1 rev:
GTTCCCAAAACCTTCGTTG

Gata1 fwd:
agagcctaaaaggtcctcca

Gata1 rev:
caccttctccctcctctttc
```

Hybridization to DNA Microarray

Purified immunoprecipitated DNA was amplified using two rounds of ligation mediated PCR (LM PCR), as described in (Lee et al., 2006b) and the Agilent Mammalian ChIP-on-chip protocol (version 9.1, November 2006). LM-PCR immunoprecipitated DNA was labeled with Cy5, LM-PCR input DNA was labeled with Cy3 using Invitrogen Bioprime random primer labeling kit. For microarray hybridization, the Agilent Mammalian ChIP-on-chip protocol (version 9.1, November 2006) was followed. In brief, mouse Cot1 DNA, Agilent blocking buffer (1× final conc.), Agilent hybridization buffer (1× final conc.), was added to Cy5- and Cy3-labeled DNA. The mixture was incubated at 95° C. for 3 minutes, followed by 37° C. for 30 minutes. Sample was centrifuged for 1 min and sample was hybridized to Agilent DNA microarray. For experiments testing effects of flavopiridol on NelfA and Spt5 occupancy, and NelfA or Spt5 occupancy following Spt5 or NelfA knockdown, respectively, ChIP samples were hybridized to Agilent arrays MTvB (44,000 features covering the promoter region, from approximately −6 kb to +2 kb, of approximately 10% of mouse genes—MTvB). DNA was hybridized to microarray for 40 hours at 65° C. Microarray was washed and scanned following the Agilent Mammalian ChIP-on-chip protocol. The Agilent DNA microarray scanner BA was used. PMT settings were set manually to normalize bulk signal in the Cy3 and Cy5 channel. Data was processed as described in (Lee et al., 2006a) to calculate enrichment ratios and determine bound regions. Figures presented in this application using ChIP-chip data display the chromosomal coordinates from mouse genome build mm6.

Solexa/Illumina Sequencing

All protocols used for Solexa/Illumina ChIP-seq analysis (sample preparation, polony generation on Solexa flow-cells, sequencing, and Solexa data analysis) are described in (Guenther et al., 2008; Marson et al., 2008). A summary of the protocol used is described below.

Sample preparation. Purified immunoprecipitated DNA was prepared for sequencing according to a modified version of the Illumina/Solexa Genomic DNA protocol. Fragmented DNA was prepared by repairing the ends and adding a single adenine nucleotide overhang to allow for directional ligation. A 1:100 dilution (in water) of the Adaptor Oligo Mix (Illumina) was used in the ligation step. A subsequent PCR step with limited (18) amplification cycles added additional linker sequence to the fragments to prepare them for annealing to the Genome Analyzer flow-cell. Following amplification, the library was size selected to a narrow range of fragment sizes by separation on a 2% agarose gel and a band between 150-300 bp (representing shear fragments between 50 and 200 nt in length and ~100 bp of primer sequence) was excised. The DNA was purified from the agarose and this DNA library was subsequently used for polony generation and sequencing.

Polony Generation and Sequencing. The DNA library (2-4 pM) was applied to the flow-cell (8 samples per flow-cell) using the Cluster Station device from Illumina. The concentration of library applied to the flow-cell was calibrated such that polonies generated in the bridge amplification step originate from single strands of DNA. Multiple rounds of amplification reagents were flowed across the cell in the bridge amplification step to generate polonies of approximately 1,000 strands in 1 μm diameter spots. Double stranded polonies were visually checked for density and morphology by staining with a 1:5000 dilution of SYBR Green I (Invitrogen) and visualizing with a microscope under fluorescent illumination. Validated flow-cells were stored at 4° C. until sequencing.

Flow-cells were removed from storage and subjected to linearization and annealing of sequencing primer on the Cluster Station. Primed flow-cells were loaded into the Illumina Genome Analyzer 1G. After the first base was incorporated in the Sequencing-by-Synthesis reaction the process was paused for a key quality control checkpoint. A small section of each lane was imaged and the average intensity value for all four bases was compared to minimum thresholds. Flow-cells with low first base intensities were re-primed and if signal was not recovered the flow-cell was aborted. Flow-cells with signal intensities meeting the minimum thresholds were resumed and sequenced for 26 or 32 cycles.

Solexa Data Analysis. Images acquired from the Illumina/Solexa sequencer were processed through the bundled Solexa image extraction pipeline, which identified polony positions, performed base-calling and generated QC statistics. Sequences were aligned using ELAND software to NCBI Build 36 (UCSC mm8) of the mouse genome. Only sequences that mapped uniquely to the genome with zero or one mismatch were used for further analysis. When multiple reads mapped to the same genomic position, a maximum of two reads mapping to the same position were used. Refer to Table S1 for a list of the total number of mapped reads used for analysis of each ChIP-seq dataset.

Analysis methods were derived from previously published methods (Johnson et al., 2007; Mikkelsen et al., 2007; Marson et al., 2008; Guenther et al., 2008). Sequence reads from multiple flow cell runs were combined for Pol II Ser2P ChIP-seq dataset. Each read was extended 100 bp, towards the interior of the sequenced fragment, based on the strand of the alignment. The number of ChIP-Seq reads across the genome, in 25 bp bins within a 1 kb window surrounding each bin (+/−500 bp) was tabulated. The 25 bp genomic bins that contained statistically significant ChIP-Seq enrichment was identified by comparison to a Poissonian background model. Assuming background reads are spread randomly throughout the genome, the probability of observing a given number of reads in a 1 kb window can be modeled as a Poisson process in which the expectation can be estimated as the number of mapped reads multiplied by the number of bins (40) into which each read maps, divided by the total number of bins available (we estimated 70%). Enriched bins within 1 kb of one another were combined into regions. The complete set of RefSeq genes was downloaded from the UCSC table browser (http://genome.ucsc.edu/cgi-bin/hgTables?command=start) on Dec. 20, 2008. Genes with enriched regions within 1 kb to their transcription start site to annotated stop site were called bound.

The Poissonian background model assumes a random distribution of background reads, however we have observed significant deviations from this expectation. Some of these non-random events can be detected as sites of apparent enrichment in negative control DNA samples and can create many false positives in ChIP-Seq experiments. To remove these regions, we compared genomic bins and regions that meet the statistical threshold for enrichment to a set of reads obtained from Solexa sequencing of DNA from whole cell extract (WCE) in matched cell samples. We required that enriched bins and enriched regions have five-fold greater ChIP-Seq density in the specific IP sample, compared with the control sample, normalized to the total number of reads in each dataset. This served to filter out genomic regions that are biased to having a greater than expected background density of ChIP-Seq reads. A summary of the bound regions and genes for each antibody is provided in Table S3 and Table S4.

For comparison of Pol II occupancy following either shRNA-mediated knockdown or small molecule inhibition with a control dataset, rank normalization was used to normalize the datasets to be compared. This normalization method is described in (Bilodeau et al., 2009). Briefly, a quantile normalization method was used for analysis. For each dataset compared, the genomic bin with the greatest ChIP-Seq density was identified. The average of these values was calculated and the highest signal bin in each dataset was assigned this average value. This was repeated for all genomic bins from the greatest signal to the least, assigning each the average ChIP-Seq signal for all bins of that rank across all datasets.

Active and Non-Productive Gene Classes in mES Cells

The active and non-productive genes were classified in mES cells using H3K4me3 (initiation-associated chromatin modification) and H3K79me2 (elongation-associated chromatin modification), as determined by ChIP-seq (Marson et al. 2008), as markers of transcriptional state. Active genes with both H3K4me3 and H3K79me2 chromatin modifications, non-productive genes had only H3K4me3 and inactive genes did not have H3K4me3 or H3K79me2 chromatin modifications. When showing Rpl3 as the example of the active gene and Surb 7 as the example of the non-productive gene in FIG. 1A and FIG. 3A, the Pol II (all) dataset used for generating the gene plots was Pol II (all) shControl (from shSpt5 and shNelfA experiment).

Traveling Ratio Calculation

Pol II levels peak in the 5' region of many genes. To quantify this effect, we have developed a measure called Traveling Ratio (TR) that compares the ratio between Pol II density in the promoter and in the gene region. We first defined the promoter region from −30 to +300 relative to the TSS and the gene body as the remaining length of the gene. We next calculated the average density/nt from rank normalized ChIP-seq density files (described in Bilodeau et al. 2009) for each region and computed the TR as the ratio between the two. Following perturbation from either shRNA knockdown or small molecule inhibition, TR can shift either through changes in the density of promoter proximal Pol II or changes in the gene body Pol II density. For example, FIG. 12 shows examples of genes where knockdown of Spt5 or NelfA cause a decrease in promoter proximal Pol II density while FIG. 4B shows examples where knockdown of Spt5 causes increases in Pol II density in gene bodies, sometimes accompanied by lower amounts of promoter proximal density.

Figure 15A:
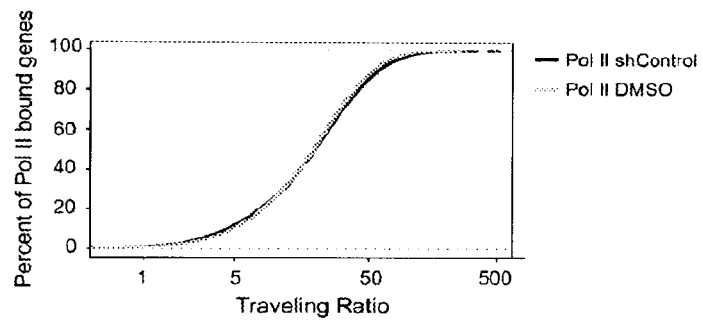
FIGS. 15A to 15C. Traveling ratio plots for Pol II in two different control ChIP-seq datasets. (A) Traveling ratios plots for Pol II occupancy in two mES control datasets (mES cells+shControl (from shNelfA and shSpt5 experiment) and mES cells+DMSO). (B) Traveling ratio as a function of gene expression, finding no statistically significant correlation between TR and gene expression. (C) Amount of Pol II Ser2P in the gene end region (+/−1 kb from the 3' end of gene) as a function of gene expression, finding a weak correlation between the two.

TR values were calculated for all Pol II bound genes. Pol II occupancy profiles and their corresponding TR value for several example genes are shown in FIG. 9. For this figure, the Pol II (all) shControl (from shNelfA and shSpt5 experiment) was used for the gene plots. TR values also show strong agreement between the two control datasets (Pol II shControl and Pol II DMSO), as distributions of TR values are not statistically different (p-Value <0.5) as determined by a Welch's T-Test (FIG. 15A).

Figure 15B:
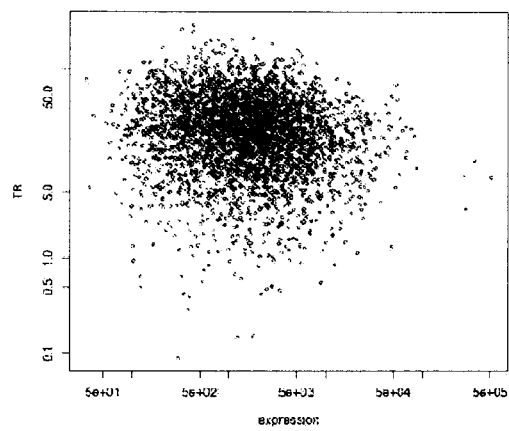
Figure 15C:
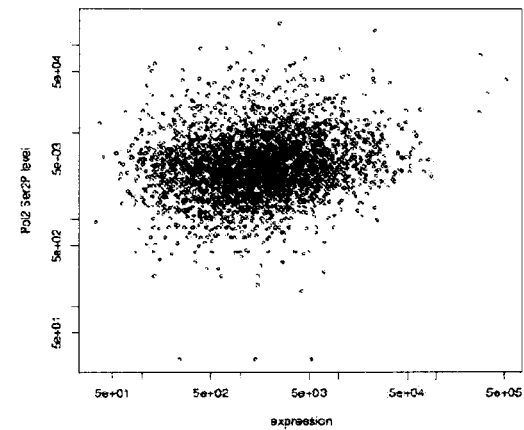

TR values were plotted as a function of gene expression in FIG. 15B. Expression data used was from (Hailesellasse Sene et al., 2007). No statistically significant correlation was found between TR and gene expression. In contrast, when Pol II Ser2P occupancy at the gene end (the region +/−1 kb from the 3' end of the gene) is plotted as a function of gene expression (FIG. 15C), we see a weak correlation between the two variables.

Mapping DSIF and NELF Peaks Relative to Pol II Peaks and Correlation Calculations We find that NelfA and Spt5 enrichment spatially overlaps distributions of Pol II near TSS. To determine the spatial relationships between Pol II, NELF, and DSIF, at individual genes, we mapped the location of significant peaks of Spt5 and NelfA relative to locations of downstream Pol II peaks, as determined by a high resolution peak finding algorithm. This algorithm is designed to operate on top of traditional bound region enrichment models—such as the one used in this study—to precisely map binding sites from ChIP-Seq data at higher resolution. The method operates on the assumption that broader "bound regions" of statistical enrichment have already been defined, and that within these "bound regions", exists one or more true binding events. Our method is similar to methods used to map ChIP-Seq peaks (Zhang et al., 2008, Marson et al. 2008) in that it primarily utilizes the requirement of a paired forward read and reverse read peak. We searched 500 nt upstream and downstream of the Pol II peak for the most significant peak in NelfA and Spt5 ChIP-Seq enrichment that was called enriched above 1e-9 threshold by our gene calling algorithm. If a gene was not enriched for NelfA or Spt5 at this threshold, then it was automatically determined as not co-localized with the Pol II peak.

88% of downstream Pol II peaks were co-localized by a corresponding peak of NelfA. Similarly, 61% of Pol II peaks were co-localized by a corresponding Spt5 peak. By visual inspection, we found a majority of Pol II peaks where the peak-finding algorithm failed to identify co-localized Spt5 and NelfA peaks to be co-occupied by NelfA or Spt5 peaks, just below cutoff thresholds for calling a bound gene. This suggests that the high threshold of the peak finding algorithm under reported the number of true instances of Pol II and NELF/DSIF co-localization, and indeed NelfA and Spt5 occupancy positively correlate with Pol II occupancy (FIG. 11A) further support for general co-localization of NELF and DSIF to Pol II. Almost all identified promoter proximal peaks of Spt5 and NelfA occurred within +/−50 nt of the Pol II peak. In contrast, when we applied the same analysis to nearest peaks of H3K4me3, the majority of peaks were found more than +/−50 nt from the Pol II peak.

Heatmap Analysis on ChIP-seq Occupancy

ChIP-seq enrichment for the indicated factor or modification was determined in 50 bp bins (enrichment in the bin as counts per million), centered on each transcriptional start site. Generally, the gene list for each representation was rank ordered based on the amount of Pol II (all) in mES cells, from most to least to correlate the enrichment of the given factor with the amount of Pol II at each gene. Cluster 3.0 (http://bonsai.ims.u-tokyo.ac.jp/~mdehoon/software/cluster/software.htm) and Java Treeview (www.jtreeview.sourceforge.ne) were used to visualize the data and generate figures shown herein.

To determine the transcriptional state of Oct4, Nanog and c-Myc target genes in mES cells, enriched genes were determined for each factor at p value 1e-8. Many studies have found that the distance between an Oct4 and Nanog binding site and the gene transcriptional start site can vary widely (Boyer et al., 2005; Chen et al., 2008; Kim et al., 2008; Marson et al., 2008). However, c-Myc binding is generally centered within 1 kb of the transcriptional start site (Chen et al., 2008; Kim et al., 2008). To take this into account Oct4 and Nanog target genes were determined +/−5 kb around each transcriptional start site and c-Myc target genes were determined +/−1 kb around each transcriptional start site. The transcriptional state was then determined for each bound gene set through determining the occupancy of Pol II Ser5P, H3K4me3 (initiation-associated chromatin modification), H3K79me2 (elongation-associated chromatin modification) and H3K27me3 (repression-associated chromatin modification). The data was displayed at each gene centered on the TSS from −2.5 kb to +3 kb, rank ordered based amount of Pol II Ser5P, using Cluster3.0 and Treeview (described above).

Determining Target and Non-Target Gene Sets

To determine c-Myc and Oct4 target and non-target genes for analysis on changes in Pol II ChIP-seq occupancy, we first ordered all active genes by c-Myc or Oct4 occupancy near the promoter (+/−1 kb for c-Myc and +/−5 kb for Oct4). For c-Myc genes, the top 1000 and lowest 1000 genes by c-Myc occupancy were demarcated as target and non-target genes respectively. For Oct4, we selected as targets the top 100 Oct4 bound genes that also showed at least a −0.2 fold change in expression following Oct4 shutdown (Matoba et al., 2006). The Oct4 non-targets were determined by taking the lowest 100 Oct4 bound genes for which expression data existed.

Global Analysis of Pol II Occupancy Changes Following cMyc/Max Inhibition

To determine the effect and significance of changes in Pol II occupancy at c-Myc target genes following treatment with 10058-F4, we first derived sets of actively elongating c-Myc targets and non-targets. Actively elongating genes were defined as those bound by Pol II within 1 kb of the TSS at a p-Value of 1e-9 and also bound by H3K79me3 in the first 5 kb of the gene, again at a p-Value of 1e-9.

Actively elongating genes were ranked by c-Myc levels within +/−1 kb of the TSS, as cMyc generally associates with its target genes close to the TSS (Chen et al., 2008; Kim et al., 2008). We analyzed the effects on transcription following c-Myc/Max inhibition by generating average Pol II occupancy in the promoter or the gene body region for the high confidence c-Myc targets using rank normalized datasets. For the average Pol II occupancy analysis shown in FIG. 6C, we used the high confidence set of c-Myc targets and non-c-Myc targets containing the top 100 c-Myc target genes and the bottom 100 genes from the rank ordering. This set of target genes and non-target genes were also used for the Pol II TR analysis following 10058-F4 treatment using rank normalized ChIP-seq density data (FIG. 6D).

In order to determine the significance of these changes, we calculated the Pol II density for each gene in the promoter, and the gene body plus gene end region, expanding the target genes to the top 1000 and bottom 1000 genes ranked by c-Myc levels were respectively used as a target and non-target set for further statistical analysis. Regions are delineated in FIG. 6. Averages of the Pol II occupancy at c-Myc targets show a loss of Pol II in the gene body and gene end following 10058-F4 treatment. No such loss is seen in non-target genes. Additionally, levels of Pol II at the promoter appear unchanged following 10058-F4 treatment in both target and non-target genes. We used a Welch's T-Test to determine whether distributions of gene densities in control versus 10058-F4 treated cells could be generated by the same distribution in each region for target and non-target genes. We found significant changes in Pol II occupancy only in the gene body of cMyc target genes (p=7.341e-06) but not the promoter region (p=0.4536) of c-Myc genes. Non c-Myc target genes did not have a statistically significant change in either gene region (p<0.001). These data suggest that 10058-F4 causes a loss in Pol II occupancy specifically at c-Myc target genes.

Co-Immunoprecipitation Analysis

Co-immunoprecipitation studies were done in mES cells using IgG: Upstate/Millipore, anti-c-Myc: Santa Cruz sc-764, anti-Max: Santa Cruz sc-197, anti-Cdk9 Santa Cruz sc-484, anti-CycT1: gift from David Price (Peng et al., 1998). Max was immunoprecipitated from mES cell lysates made in Lysis Buffer (20 mM Tris pH 8.0, 150 mM NaCl, 10% glycerol, 1% NP-40, 2 mM EDTA and protease inhibitors) using anti-IgG control, anti-c-Myc, anti-Max, anti-Cdk9 and anti-CycT1 and incubated overnight at 4° C. CycT1 and Cdk9 were immunoprecipitated with mES cell lysates made in Lysis Buffer using anti-IgG control, anti-c-Myc, anti-Max and anti-Cdk9 and incubated for 3 hours at 4° C. Immunoprecipitates were washed three times with lysis buffer and proteins were analyzed by SDS-PAGE gel electrophoresis followed by Western blot analysis.

Western Blots

Western blots were done following standard protocols. Antibodies used for Western blots were as follows: Spt5: gift of Yuki Yamaguchi and Hiroshi Handa (Wada et al., 1998); NelfA: gift of Yuki Yamaguchi and Hiroshi Handa; Cdk9: Santa Cruz sc-484 and sc-8338, Ser2P Pol II: Abcam (H5 clone) ab24758; Ser5P Pol II: Abcam ab5131; Brg1: Santa Cruz sc-10768; Max: Santa Cruz sc-197; c-Myc: Santa Cruz-764; Cyclin T1: gift of David Price; Oct4: Santa Cruz sc-5279; and TBP: Abcam ab818. Secondary antibodies used were anti-rabbit IgG (HRP-conjugated; GE Healthcare—NA934V), anti-mouse IgG (HRP-conjugated; GE Healthcare—NA931V), anti-Protein A (HRP-conjugated; GE Healthcare—NA9120V), anti-sheep (HRP-conjugated; Santa Cruz—sc2770) and anti-mouse IgG+IgM (HRP-conjugated; Jackson ImmunoResearch—115-035-044).

Expression Analysis

RNA was extracted from mES cells treated with 10058-F4 or DMSO alone with biological replicates using Qiagen Qiashredder and RNeasy kits. Residual DNA was degraded using DNA-free kit for DNAse treatment (Ambion). cDNA was generated from the DNA-free RNA using Superscript III First Strand reverse transcriptase PCR kits. Expression was determined using quantitative PCR analysis using Taqman assays in triplicate against Gapdh (Mm99999915_g1), Rnf2 (Mm00803321_m1), Brg1 (Mm01151944_m1), Atic (Mm00546566_m1), Bax (Mm00432050_m1), Nol5 (Mm00479705_m1), Brca2 (Mm00464784_m1), and Zfp451 (Mm00659728_m1). Expression was normalized against Gapdh internal control and displayed as a percentage of expression in the DMSO alone control. c-Myc mRNA levels were quantitated following sh c-Myc knockdown analysis using duplicate Taqman assays for c-Myc (Mm00487804_m1) and normalized against Gapdh.

SUPPLEMENTAL REFERENCES

Arabi, A., Wu, S., Ridderstrale, K., Bierhoff, H., Shiue, C., Fatyol, K., Fahlen, S., Hydbring, P., Soderberg, O., Grummt, I., et al. (2005). c-Myc associates with ribosomal DNA and activates RNA polymerase I transcription. Nat Cell Biol 7, 303-310.

Bilodeau, S., Kagey, M.H., Frampton, G.M., Rahl, P.B., and Young, R.A. (2009). SetDB1 contributes to repression of genes encoding developmental regulators and maintenance of ES cell state. Genes Dev 23, 2484-2489.

Boyer, L. A., Lee, T. I., Cole, M. F., Johnstone, S. E., Levine, S. S., Zucker, J. P., Guenther, M. G., Kumar, R. M., Murray, H. L., Jenner, R. G., et al. (2005). Core transcriptional regulatory circuitry in human embryonic stem cells. Cell 122, 947-956.

Chen, X., Xu, H., Yuan, P., Fang, F., Huss, M., Vega, V. B., Wong, E., Orlov, Y. L., Zhang, W., Jiang, J., et al. (2008). Integration of external signaling pathways with the core transcriptional network in embryonic stem cells. Cell 133, 1106-1117.

Fang, Z. H., Dong, C. L., Chen, Z., Zhou, B., Liu, N., Lan, H.F., Liang, L., Liao, W. B., Zhang, L., and Han, Z.C. (2008). Transcriptional regulation of survivin by c-Myc in BCR/ABL-transformed cells: implications in antileukemic strategy. J Cell Mol Med.

Faumont, N., Durand-Panteix, S., Schlee, M., Gromminger, S., Schuhmacher, M., Holzel, M., Laux, G., Mailhammer, R., Rosenwald, A., Staudt, L. M., et al. (2009). c-Myc and Rel/NF-kappaB are the two master transcriptional systems activated in the latency III program of Epstein-Barr virus-immortalized B cells. J Virol 83, 5014-5027.

Follis, A. V., Hammoudeh, D. I., Wang, H., Prochownik, E. V., and Metallo, S. J. (2008). Structural rationale for the coupled binding and unfolding of the c-Myc oncoprotein by small molecules. Chem Biol 15, 1149-1155.

Guenther, M. G., Lawton, L. N., Rozovskaia, T., Frampton, G. M., Levine, S. S., Volkert, T. L., Croce, C. M., Nakamura, T., Canaani, E., and Young, R. A. (2008). Aberrant chromatin at genes encoding stem cell regulators in human mixed-lineage leukemia. Genes Dev 22, 3403-3408.

Hailesellasse Sene, K., Porter, C. J., Palidwor, G., Perez-Iratxeta, C., Muro, E. M., Campbell, P. A., Rudnicki, M. A., and Andrade-Navarro, M. A. (2007). Gene function in early mouse embryonic stem cell differentiation. BMC Genomics 8, 85.

Hammoudeh, D. I., Follis, A. V., Prochownik, E. V., and Metallo, S. J. (2009). Multiple independent binding sites for small-molecule inhibitors on the oncoprotein c-Myc. J Am Chem Soc 131, 7390-7401.

Khanna, A., Bockelman, C., Hemmes, A., Junttila, M. R., Wiksten, J. P., Lundin, M., Junnila, S., Murphy, D. J., Evan, G. I., Haglund, C., et al. (2009). MYC-dependent regulation and prognostic role of CIP2A in gastric cancer. J Natl Cancer Inst 101, 793-805.

Kim, J., Chu, J., Shen, X., Wang, J., and Orkin, S. H. (2008). An extended transcriptional network for pluripotency of embryonic stem cells. Cell 132, 1049-1061.

Lee, T. I., Jenner, R. G., Boyer, L. A., Guenther, M. G., Levine, S. S., Kumar, R. M., Chevalier, B., Johnstone, S. E., Cole, M. F., Isono, K., et al. (2006a). Control of developmental regulators by Polycomb in human embryonic stem cells. Cell 125, 301-313.

Lee, T. I., Johnstone, S. E., and Young, R. A. (2006b). Chromatin immunoprecipitation and microarray-based analysis of protein location. Nat Protoc 1, 729-748.

Lee, W. H., Liu, F. H., Lin, J. Y., Huang, S. Y., Lin, H., Liao, W. J., and Huang, H. M. (2009). JAK pathway induction of c-Myc critical to IL-5 stimulation of cell proliferation and inhibition of apoptosis. J Cell Biochem 106, 929-936.

Marson, A., Levine, S. S., Cole, M. F., Frampton, G. M., Brambrink, T., Johnstone, S., Guenther, M. G., Johnston, W. K., Wernig, M., Newman, J., et al. (2008). Connecting microRNA genes to the core transcriptional regulatory circuitry of embryonic stem cells. Cell 134, 521-533.

Matoba, R., Niwa, H., Masui, S., Ohtsuka, S., Carter, M. G., Sharov, A. A., and Ko, M. S. (2006). Dissecting Oct3/4-regulated gene networks in embryonic stem cells by expression profiling. PLoS One 1, e26.

Mikkelsen, T. S., Ku, M., Jaffe, D. B., Issac, B., Lieberman, E., Giannoukos, G., Alvarez, P., Brockman, W., Kim, T. K., Koche, R. P., et al. (2007). Genome-wide maps of chromatin state in pluripotent and lineage-committed cells. Nature 448, 553-560.

Niwa, H., Miyazaki, J., and Smith, A. G. (2000). Quantitative expression of Oct-3/4 defines differentiation, dedifferentiation or self-renewal of ES cells. Nat Genet 24, 372-376.

Peng, J., Zhu, Y., Milton, J. T., and Price, D. H. (1998). Identification of multiple cyclin subunits of human P-TEFb. Genes Dev 12, 755-762.

Sampson, V. B., Rong, N. H., Han, J., Yang, Q., Aris, V., Soteropoulos, P., Petrelli, N. J., Dunn, S. P., and Krueger, L. J. (2007). MicroRNA let-7a down-regulates MYC and reverts MYC-induced growth in Burkitt lymphoma cells. Cancer Res 67, 9762-9770.

Stock, J. K., Giadrossi, S., Casanova, M., Brookes, E., Vidal, M., Koseki, H., Brockdorff, N., Fisher, A. G., and Pombo, A. (2007). Ringl-mediated ubiquitination of H2A restrains poised RNA polymerase II at bivalent genes in mouse ES cells. Nat Cell Biol 9, 1428-1435.

Wada, T., Takagi, T., Yamaguchi, Y., Ferdous, A., Imai, T., Hirose, S., Sugimoto, S., Yano, K., Hartzog, G. A., Winston, F., et al. (1998). DSIF, a novel transcription elongation factor that regulates RNA polymerase II processivity, is composed of human Spt4 and Spt5 homologs. Genes Dev 12, 343-356.

Wang, H., Hammoudeh, D. I., Follis, A. V., Reese, B. E., Lazo, J. S., Metallo, S. J., and Prochownik, E. V. (2007). Improved low molecular weight Myc-Max inhibitors. Mol Cancer Ther 6, 2399-2408.

Yamada, T., Yamaguchi, Y., Inukai, N., Okamoto, S., Mura, T., and Handa, H. (2006). P-TEFb-mediated phosphorylation of hSpt5 C-terminal repeats is critical for processive transcription elongation. Mol Cell 21, 227-237.

Example 7

Effect of Combined Flavopiridol and 10058-F4 on Pol II Density in Transcribed Regions of c-Myc Target Genes and non-c-Myc Target Genes Tumor cells and normal cells are treated with flavopiridol and 10058-F4 at a range of different concentrations. The effect of the compound combination of Pol II occupancy is assessed using ChIP-seq. The ability of 10058-F4 to augment the effect due to flavopiridol at c-Myc target genes versus non-c-Myc target genes, e.g., when flavopiridol is used at doses lower than those described in the preceding Examples, is assessed. The ability of flavopiridol at low concentrations to augment the effect of 10058-F4 at c-Myc target genes versus non c-Myc target genes is assessed. The effects of the combination on proliferation of normal cells versus tumor cells is assessed.

Example 8

Effect of Combined Administration of Flavopiridol and 10058-F4

Flavopiridol is administered at different doses either alone or in combination with a c-Myc inhibitor, e.g., 10058-F4 to groups of mice bearing tumor xenografts. The effect of the flavopiridol and the compound combinations on tumor growth are assessed at various time points after administration. Reduced tumor growth in animals receiving the combination relative to animals receiving the same amount of flavopiridol as a single agent evidences the enhanced efficacy of the compound combination.

REFERENCES

Adelman, K., Wei, W., Ardehali, M. B., Werner, J., Zhu, B., Reinberg, D., and L is, J. T. (2006). Drosophila Paf1 modulates chromatin structure at actively transcribed genes. Mol Cell Biol 26, 250-260.

Ahn, S. H., Kim, M., and Buratowski, S. (2004). Phosphorylation of serine 2 within the RNA polymerase II C-terminal domain couples transcription and 3' end processing. Mol Cell 13, 67-76.

Andrulis, E. D., Guzman, E., Doring, P., Werner, J., and L is, J. T. (2000). High-resolution localization of Drosophila Spt5 and Spt6 at heat shock genes in vivo: roles in promoter proximal pausing and transcription elongation. Genes Dev 14, 2635-2649.

Barboric, M., Lenasi, T., Chen, H., Johansen, E. B., Guo, S., and Peterlin, B. M. (2009). 7SK snRNP/P-TEFb couples transcription elongation with alternative splicing and is essential for vertebrate development. Proc Natl Acad Sci USA 106, 7798-7803.

Barboric, M., Nissen, R. M., Kanazawa, S., Jabrane-Ferrat, N., and Peterlin, B. M. (2001). NF-kappaB binds P-TEFb to stimulate transcriptional elongation by RNA polymerase II. Mol Cell 8, 327-337.

Barboric, M., and Peterlin, B. M. (2005). A new paradigm in eukaryotic biology: HIV Tat and the control of transcriptional elongation. PLoS Biol 3, e76.

Barski, A., Cuddapah, S., Cui, K., Roh, T.Y., Schones, D.E., Wang, Z., Wei, G., Chepelev, I., and Zhao, K. (2007). High-resolution profiling of histone methylations in the human genome. Cell 129, 823-837.

Baugh, L. R., Demodena, J., and Sternberg, P. W. (2009). RNA Pol II accumulates at promoters of growth genes during developmental arrest. Science 324, 92-94.

Bentley, D. L., and Groudine, M. (1986). A block to elongation is largely responsible for decreased transcription of c-myc in differentiated HL60 cells. Nature 321, 702-706.

Boettiger, A. N., and Levine, M. (2009). Synchronous and stochastic patterns of gene activation in the Drosophila embryo. Science 325, 471-473.

Cartwright, P., McLean, C., Sheppard, A., Rivett, D., Jones, K., and Dalton, S. (2005). LIF/STAT3 controls ES cell self-renewal and pluripotency by a Myc-dependent mechanism. Development 132, 885-896.

Chao, S. H., Fujinaga, K., Marion, J. E., Taube, R., Sausville, E. A., Senderowicz, A. M., Peterlin, B. M., and Price, D. H. (2000). Flavopiridol inhibits P-TEFb and blocks HIV-1 replication. J Biol Chem 275, 28345-28348.

Chao, S. H., and Price, D. H. (2001). Flavopiridol inactivates P-TEFb and blocks most RNA polymerase II transcription in vivo. J Biol Chem 276, 31793-31799.

Chen, X., Xu, H., Yuan, P., Fang, F., Huss, M., Vega, V. B., Wong, E., Orlov, Y. L., Zhang, W., Jiang, J., et al. (2008). Integration of external signaling pathways with the core transcriptional network in embryonic stem cells. Cell 133, 1106-1117.

Cheng, B., and Price, D.H. (2007). Properties of RNA polymerase II elongation complexes before and after the P-TEFb-mediated transition into productive elongation. J Biol Chem 282, 21901-21912.

Cho, W. K., Zhou, M., Jang, M. K., Huang, K., Jeong, S. J., Ozato, K., and Brady, J. N. (2007). Modulation of the Brd4/P-TEFb interaction by the human T-lymphotropic virus type 1 tax protein. J Virol 81, 11179-11186.

Chopra, V. S., Hong, J. W., and Levine, M. (2009). Regulation of Hox gene activity by transcriptional elongation in Drosophila. Curr Biol 19, 688-693.

Christian, B. A., Greyer, M. R., Byrd, J. C., and Lin, T. S. (2007). Flavopiridol in the treatment of chronic lymphocytic leukemia. Curr Opin Oncol 19, 573-578.

Core, L. J., and L is, J. T. (2008). Transcription regulation through promoter-proximal pausing of RNA polymerase II. Science 319, 1791-1792.

Core, L. J., Waterfall, J. J., and L is, J. T. (2008). Nascent RNA sequencing reveals widespread pausing and divergent initiation at human promoters. Science 322, 1845-1848.

Eberhardy, S. R., and Farnham, P. J. (2001). c-Myc mediates activation of the cad promoter via a post-RNA polymerase II recruitment mechanism. J Biol Chem 276, 48562-48571.

Eberhardy, S. R., and Farnham, P. J. (2002). Myc recruits P-TEFb to mediate the final step in the transcriptional activation of the cad promoter. J Biol Chem 277, 40156-40162.

Eilers, M., and Eisenman, R. N. (2008). Myc's broad reach. Genes Dev 22, 2755-2766.

Espinosa, J. M., Verdun, R. E., and Emerson, B. M. (2003). p53 functions through stress- and promoter-specific recruitment of transcription initiation components before and after DNA damage. Mol Cell 12, 1015-1027.

Fuda, N. J., Ardehali, M. B., and L is, J. T. (2009). Defining mechanisms that regulate RNA polymerase II transcription in vivo. Nature 461, 186-192.

Gargano, B., Amente, S., Majello, B., and Lania, L. (2007). P-TEFb is a crucial co-factor for Myc transactivation. Cell Cycle 6, 2031-2037.

Ghosh, D., and Seydoux, G. (2008) Inhibition of transcription by the Caenorhabditis elegans germline protein PIE-1: genetic evidence for distinct mechanisms targeting initiation and elongation. Genetics 178, 235-243.

Gilmour, D. S., and L is, J. T. (1986). RNA polymerase II interacts with the promoter region of the noninduced hsp70 gene in Drosophila melanogaster cells. Mol Cell Biol 6, 3984-3989.

Glover-Cutter, K., Kim, S., Espinosa, J., and Bentley, D. L. (2008). RNA polymerase II pauses and associates with pre-mRNA processing factors at both ends of genes. Nat Struct Mol Biol 15, 71-78.

Guenther, M. G., Levine, S. S., Boyer, L. A., Jaenisch, R., and Young, R. A. (2007). A chromatin landmark and transcription initiation at most promoters in human cells. Cell 130, 77-88.

Hall, J., Guo, G., Wray, J., Eyres, I., Nichols, J., Grotewold, L., Morfopoulou, S., Humphreys, P., Mansfield, W., Walker, R., et al. (2009). Oct4 and LIF/Stat3 additively induce Kruppel factors to sustain embryonic stem cell self-renewal. Cell Stem Cell 5, 597-609.

Hammoudeh, D. I., Follis, A. V., Prochownik, E. V., and Metallo, S. J. (2009). Multiple independent binding sites for small-molecule inhibitors on the oncoprotein c-Myc. J Am Chem Soc 131, 7390-7401.

Hanyu-Nakamura, K., Sonobe-Nojima, H., Tanigawa, A., Lasko, P., and Nakamura, A. (2008). *Drosophila* Pgc protein inhibits P-TEFb recruitment to chromatin in primordial germ cells. Nature 451, 730-733.

Hochheimer, A., and Tjian, R. (2003). Diversified transcription initiation complexes expand promoter selectivity and tissue-specific gene expression. Genes Dev 17, 1309-1320.

Kadonaga, J. T. (2004). Regulation of RNA polymerase II transcription by sequence-specific DNA binding factors. Cell 116, 247-257.

Kanazawa, S., Soucek, L., Evan, G., Okamoto, T., and Peterlin, B. M. (2003). c-Myc recruits P-TEFb for transcription, cellular proliferation and apoptosis. Oncogene 22, 5707-5711.

Kidder, B. L., Yang, J., and Palmer, S. (2008). Stat3 and c-Myc genome-wide promoter occupancy in embryonic stem cells. PLoS One 3, e3932.

Kim, J., Chu, J., Shen, X., Wang, J., and Orkin, S.H. (2008). An extended transcriptional network for pluripotency of embryonic stem cells. Cell 132, 1049-1061.

Kim, J. B., and Sharp, P. A. (2001). Positive transcription elongation factor B phosphorylates hSPT5 and RNA polymerase II carboxyl-terminal domain independently of cyclin-dependent kinase-activating kinase. J Biol Chem 276, 12317-12323.

Kim, M., Ahn, S. H., Krogan, N. J., Greenblatt, J. F., and Buratowski, S. (2004). Transitions in RNA polymerase II elongation complexes at the 3' ends of genes. Embo J 23, 354-364.

Kim, T. H., Barrera, L. O., Zheng, M., Qu, C., Singer, M. A., Richmond, T. A., Wu, Y., Green, R. D., and Ren, B. (2005). A high-resolution map of active promoters in the human genome. Nature 436, 876-880.

Komarnitsky, P., Cho, E. J., and Buratowski, S. (2000). Different phosphorylated forms of RNA polymerase II and associated mRNA processing factors during transcription. Genes Dev 14, 2452-2460.

Krogan, N. J., Dover, J., Wood, A., Schneider, J., Heidt, J., Boateng, M. A., Dean, K., Ryan, O. W., Golshani, A., Johnston, M., et al. (2003). The Paf1 complex is required for histone H3 methylation by COMPASS and Dot1p: linking transcriptional elongation to histone methylation. Mol Cell 11, 721-729.

Lis, J. T., Mason, P., Peng, J., Price, D. H., and Werner, J. (2000). P-TEFb kinase recruitment and function at heat shock loci. Genes Dev 14, 792-803.

Maherali, N., Sridharan, R., Xie, W., Utikal, J., Eminli, S., Arnold, K., Stadtfeld, M., Yachechko, R., Tchieu, J., Jaenisch, R., et al. (2007). Directly reprogrammed fibroblasts show global epigenetic remodeling and widespread tissue contribution. Cell Stem Cell 1, 55-70.

Mandal, S. S., Chu, C., Wada, T., Handa, H., Shatkin, A. J., and Reinberg, D. (2004). Functional interactions of RNA-capping enzyme with factors that positively and negatively regulate promoter escape by RNA polymerase II. Proc Natl Acad Sci U S A 101, 7572-7577.

Margaritis, T., and Holstege, F. C. (2008). Poised RNA polymerase II gives pause for thought. Cell 133, 581-584.

Marshall, N. F., Peng, J., Xie, Z., and Price, D. H. (1996). Control of RNA polymerase II elongation potential by a novel carboxyl-terminal domain kinase. J Biol Chem 271, 27176-27183.

Marshall, N. F., and Price, D. H. (1995). Purification of P-TEFb, a transcription factor required for the transition into productive elongation. J Biol Chem 270, 12335-12338.

Marson, A., Levine, S. S., Cole, M. F., Frampton, G. M., Brambrink, T., Johnstone, S., Guenther, M. G., Johnston, W. K., Wernig, M., Newman, J., et al. (2008). Connecting microRNA genes to the core transcriptional regulatory circuitry of embryonic stem cells. Cell 134, 521-533.

Matoba, R., Niwa, H., Masui, S., Ohtsuka, S., Carter, M. G., Sharov, A. A., and Ko, M. S. (2006). Dissecting Oct3/4-regulated gene networks in embryonic stem cells by expression profiling. PLoS One 1, e26.

McCracken, S., Fong, N., Rosonina, E., Yankulov, K., Brothers, G., Siderovski, D., Hessel, A., Foster, S., Shuman, S., and Bentley, D. L. (1997a). 5'-Capping enzymes are targeted to pre-mRNA by binding to the phosphorylated carboxy-terminal domain of RNA polymerase II. Genes Dev 11, 3306-3318.

McCracken, S., Fong, N., Yankulov, K., Ballantyne, S., Pan, G., Greenblatt, J., Patterson, S. D., Wickens, M., and Bentley, D. L. (1997b). The C-terminal domain of RNA polymerase II couples mRNA processing to transcription. Nature 385, 357-361.

Meyer, N., and Penn, L.Z. (2008). Reflecting on 25 years with MYC. Nat Rev Cancer 8, 976-990.

Mikkelsen, T. S., Ku, M., Jaffe, D. B., Issac, B., Lieberman, E., Giannoukos, G., Alvarez, P., Brockman, W., Kim, T. K., Koche, R. P., et al. (2007). Genome-wide maps of chromatin state in pluripotent and lineage-committed cells. Nature 448, 553-560.

Moore, M. J., and Proudfoot, N. J. (2009). Pre-mRNA processing reaches back to transcription and ahead to translation. Cell 136, 688-700.

Morillon, A., Karabetsou, N., Nair, A., and Mellor, J. (2005). Dynamic lysine methylation on histone H3 defines the regulatory phase of gene transcription. Mol Cell 18, 723-734.

Muse, G. W., Gilchrist, D. A., Nechaev, S., Shah, R., Parker, J. S., Grissom, S. F., Zeitlinger, J., and Adelman, K. (2007). RNA polymerase is poised for activation across the genome. Nat Genet 39, 1507-1511.

Neil, H., Malabat, C., d'Aubenton-Carafa, Y., Xu, Z., Steinmetz, L. M., and Jacquier, A. (2009). Widespread bidirectional promoters are the major source of cryptic transcripts in yeast. Nature 457, 1038-1042.

Ni, Z., Saunders, A., Fuda, N. J., Yao, J., Suarez, J. R., Webb, W. W., and Lis, J. T. (2008). P-TEFb is critical for the maturation of RNA polymerase II into productive elongation in vivo. Mol Cell Biol 28, 1161-1170.

Ni, Z., Schwartz, B. E., Werner, J., Suarez, J. R., and Lis, J. T. (2004). Coordination of transcription, RNA processing, and surveillance by P-TEFb kinase on heat shock genes. Mol Cell 13, 55-65.

Niwa, H., Miyazaki, J., and Smith, A. G. (2000). Quantitative expression of Oct-3/4 defines differentiation, dedifferentiation or self-renewal of ES cells. Nat Genet 24, 372-376.

O'Brien, T., and Lis, J. T. (1991). RNA polymerase II pauses at the 5' end of the transcriptionally induced *Drosophila* hsp70 gene. Mol Cell Biol 11, 5285-5290.

Peterlin, B. M., and Price, D. H. (2006). Controlling the elongation phase of transcription with P-TEFb. Mol Cell 23, 297-305.

Pokholok, D. K., Hannett, N. M., and Young, R. A. (2002). Exchange of RNA polymerase II initiation and elongation factors during gene expression in vivo. Mol Cell 9, 799-809.

Pokholok, D. K., Harbison, C. T., Levine, S., Cole, M., Hannett, N. M., Lee, T. I., Bell, G. W., Walker, K., Rolfe, P. A., Herbolsheimer, E., et al. (2005). Genome-wide map of nucleosome acetylation and methylation in yeast. Cell 122, 517-527.

Price, D. H. (2008). Poised polymerases: on your mark . . . get set . . . go! Mol Cell 30, 7-10.

Ptashne, M., and Gann, A. (1997). Transcriptional activation by recruitment. Nature 386, 569-577.

Ptashne, M., and Gann, A. (2002). Genes & signals (Cold Spring Harbor, N.Y., Cold Spring Harbor Laboratory Press).

Reppas, N. B., Wade, J. T., Church, G. M., and Struhl, K. (2006). The transition between transcriptional initiation and elongation in E. coli is highly variable and often rate limiting. Mol Cell 24, 747-757.

Roeder, R. G. (2005). Transcriptional regulation and the role of diverse coactivators in animal cells. FEBS Lett 579, 909-915.

Rougvie, A. E., and Lis, J. T. (1988). The RNA polymerase II molecule at the 5' end of the uninduced hsp70 gene of D. melanogaster is transcriptionally engaged. Cell 54, 795-804.

Saunders, A., Core, L. J., and Lis, J. T. (2006). Breaking barriers to transcription elongation. Nat Rev Mol Cell Biol 7, 557-567.

Sawado, T., Halow, J., Bender, M. A., and Groudine, M. (2003). The beta-globin locus control region (LCR) functions primarily by enhancing the transition from transcription initiation to elongation. Genes Dev 17, 1009-1018.

Schones, D. E., Cui, K., Cuddapah, S., Roh, T. Y., Barski, A., Wang, Z., Wei, G., and Zhao, K. (2008). Dynamic regulation of nucleosome positioning in the human genome. Cell 132, 887-898.

Schubeler, D., MacAlpine, D. M., Scalzo, D., Wirbelauer, C., Kooperberg, C., van Leeuwen, F., Gottschling, D. E., O'Neill, L. P., Turner, B. M., Delrow, J., et al. (2004). The histone modification pattern of active genes revealed through genome-wide chromatin analysis of a higher eukaryote. Genes Dev 18, 1263-1271.

Seila, A. C., Calabrese, J. M., Levine, S. S., Yeo, G. W., Rahl, P. B., Flynn, R. A., Young, R. A., and Sharp, P. A. (2008). Divergent transcription from active promoters. Science 322, 1849-1851.

Seydoux, G., and Dunn, M. A. (1997). Transcriptionally repressed germ cells lack a subpopulation of phosphorylated RNA polymerase II in early embryos of Caenorhabditis elegans and Drosophila melanogaster. Development 124, 2191-2201.

Sharova, L. V., Sharov, A. A., Nedorezov, T., Piao, Y., Shaik, N., and Ko, M. S. (2009). Database for mRNA half-life of 19 977 genes obtained by DNA microarray analysis of pluripotent and differentiating mouse embryonic stem cells. DNA Res 16, 45-58.

Sims, R. J., 3rd, Belotserkovskaya, R., and Reinberg, D. (2004). Elongation by RNA polymerase II: the short and long of it. Genes Dev 18, 2437-2468.

Soucek, L., Whitfield, J., Martins, C. P., Finch, A. J., Murphy, D. J., Sodir, N. M., Karnezis, A. N., Swigart, L. B., Nasi, S., and Evan, G. I. (2008). Modelling Myc inhibition as a cancer therapy. Nature 455, 679-683.

Takahashi, K., Tanabe, K., Ohnuki, M., Narita, M., Ichisaka, T., Tomoda, K., and Yamanaka, S. (2007). Induction of pluripotent stem cells from adult human fibroblasts by defined factors. Cell 131, 861-872.

Takahashi, K., and Yamanaka, S. (2006). Induction of pluripotent stem cells from mouse embryonic and adult fibroblast cultures by defined factors. Cell 126, 663-676.

Wada, T., Takagi, T., Yamaguchi, Y., Ferdous, A., Imai, T., Hirose, S., Sugimoto, S., Yano, K., Hartzog, G. A., Winston, F., et al. (1998a). DSIF, a novel transcription elongation factor that regulates RNA polymerase II processivity, is composed of human Spt4 and Spt5 homologs. Genes Dev 12, 343-356.

Wada, T., Takagi, T., Yamaguchi, Y., Watanabe, D., and Handa, H. (1998b). Evidence that P-TEFb alleviates the negative effect of DSIF on RNA polymerase II-dependent transcription in vitro. Embo J 17, 7395-7403.

Wade, J. T., and Struhl, K. (2008). The transition from transcriptional initiation to elongation. Curr Opin Genet Dev 18, 130-136.

Wang, H., Hammoudeh, D. I., Follis, A. V., Reese, B. E., Lazo, J. S., Metallo, S. J., and Prochownik, E. V. (2007). Improved low molecular weight Myc-Max inhibitors. Mol Cancer Ther 6, 2399-2408.

Wei, P., Garber, M. E., Fang, S. M., Fischer, W. H., and Jones, K. A. (1998). A novel CDK9-associated C-type cyclin interacts directly with HIV-1 Tat and mediates its high-affinity, loop-specific binding to TAR RNA. Cell 92, 451-462.

Wen, Y., and Shatkin, A. J. (1999). Transcription elongation factor hSPT5 stimulates mRNA capping. Genes Dev 13, 1774-1779.

Wernig, M., Meissner, A., Foreman, R., Brambrink, T., Ku, M., Hochedlinger, K., Bernstein, B. E., and Jaenisch, R. (2007). In vitro reprogramming of fibroblasts into a pluripotent ES-cell-like state. Nature 448, 318-324.

Wu, C. H., Yamaguchi, Y., Benjamin, L. R., Horvat-Gordon, M., Washinsky, J., Enerly, E., Larsson, J., Lambertsson, A., Handa, H., and Gilmour, D. (2003). NELF and DSIF cause promoter proximal pausing on the hsp70 promoter in Drosophila. Genes Dev 17, 1402-1414.

Xu, Z., Wei, W., Gagneur, J., Perocchi, F., Clauder-Munster, S., Camblong, J., Guffanti, E., Stutz, F., Huber, W., and Steinmetz, L. M. (2009). Bidirectional promoters generate pervasive transcription in yeast. Nature 457, 1033-1037.

Yamada, T., Yamaguchi, Y., Inukai, N., Okamoto, S., Mura, T., and Handa, H. (2006). P-TEFb-mediated phosphorylation of hSpt5 C-terminal repeats is critical for processive transcription elongation. Mol Cell 21, 227-237.

Yamaguchi, Y., Takagi, T., Wada, T., Yano, K., Furuya, A., Sugimoto, S., Hasegawa, J., and Handa, H. (1999). NELF, a multisubunit complex containing RD, cooperates with DSIF to repress RNA polymerase II elongation. Cell 97, 41-51.

Yin, X., Giap, C., Lazo, J. S., and Prochownik, E. V. (2003). Low molecular weight inhibitors of Myc-Max interaction and function. Oncogene 22, 6151-6159.

Yoshida, M. (2001). Multiple viral strategies of HTLV-1 for dysregulation of cell growth control. Annu Rev Immunol 19, 475-496.

Zeitlinger, J., Stark, A., Kellis, M., Hong, J. W., Nechaev, S., Adelman, K., Levine, M., and Young, R. A. (2007). RNA polymerase stalling at developmental control genes in the Drosophila melanogaster embryo. Nat Genet 39, 1512-1516.

Zhang, F., Barboric, M., Blackwell, T. K., and Peterlin, B. M. (2003). A model of repression: CTD analogs and PIE-1 inhibit transcriptional elongation by P-TEFb. Genes Dev 17, 748-758.

Zhou, M., Lu, H., Park, H., Wilson-Chiru, J., Linton, R., and Brady, J. N. (2006). Tax interacts with P-TEFb in a novel manner to stimulate human T-lymphotropic virus type 1 transcription. J Virol 80, 4781-4791.

Zhu, B., Mandal, S. S., Pham, A. D., Zheng, Y., Erdjument-Bromage, H., Batra, S. K., Tempst, P., and Reinberg, D. (2005). The human PAF complex coordinates transcription with events downstream of RNA synthesis. Genes Dev 19, 1668-1673.

* * *

Those skilled in the art will recognize, or be able to ascertain using no more than routine experimentation, many equivalents to the specific embodiments of the invention described herein. The scope of the present invention is not intended to be limited to the embodiments described above. The invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

Articles such as "a" and "an", and the like, may mean one or more than one unless indicated to the contrary or otherwise evident from the context.

The phrase "and/or" as used herein in the specification and in the claims, should be understood to mean "either or both" of the elements so conjoined. Multiple elements listed with "and/or" should be construed in the same fashion, i.e., "one or more" of the elements so conjoined. Other elements may optionally be present other than the elements specifically identified by the "and/or" clause. As used herein in the specification and in the claims, "or" should be understood to have the same meaning as "and/or" as defined above. For example, when used in a list of elements, "or" or "and/or" shall be interpreted as being inclusive, i.e., the inclusion of at least one, but optionally more than one, of list of elements, and, optionally, additional unlisted elements. Only terms clearly indicative to the contrary, such as "only one of" or "exactly one of" will refer to the inclusion of exactly one element of a number or list of elements. Thus claims that include "or" between one or more members of a group are considered satisfied if one, more than one, or all of the group members are present, employed in, or otherwise relevant to a given product or process unless indicated to the contrary. The invention provides embodiments in which exactly one member of the group is present, employed in, or otherwise relevant to a given product or process. The invention also provides embodiments in which more than one, or all of the group members are present, employed in, or otherwise relevant to a given product or process. It is to be understood that the invention encompasses embodiments in which one or more limitations, elements, clauses, descriptive terms, etc., of a claim is introduced into another claim. For example, a claim that is dependent on another claim can be modified to include one or more elements or limitations found in any other claim that is dependent on the same base claim.

Where the claims recite a composition, it is understood that methods of using the composition as disclosed herein are provided, and methods of making the composition according to any of the methods of making disclosed herein are provided. Where the claims recite a method, it is understood that a composition for performing the method is provided. Where elements are presented as lists or groups, each subgroup is also disclosed. It should also be understood that, in general, where the invention, or aspects of the invention, is/are referred to as comprising particular elements, features, etc., certain embodiments of the invention or aspects of the invention consist of, or consist essentially of, such elements, features, etc.

It should also be understood that, unless clearly indicated to the contrary, in any methods claimed herein that include more than one step or act, the order of the steps or acts of the method is not necessarily limited to the order in which the steps or acts of the method are recited.

Where ranges are given herein, the invention provides embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. "About" in reference to a numerical value generally refers to a range of values that fall within ±10%, in some embodiments ±5%, in some embodiments ±1%, in some embodiments ±0.5% of the value unless otherwise stated or otherwise evident from the context. In any embodiment of the invention in which a numerical value is prefaced by "about", the invention provides an embodiment in which the exact value is recited. In any embodiment of the invention in which a numerical value is not prefaced by "about", the invention provides an embodiment in which the value is prefaced by "about". Where the phrase "at least" precedes a series of numbers, it is to be understood that the phrase applies to each number in the list (it being understood that, depending on the context, 100% of a value may be an upper limit). It is also understood that any particular embodiment, feature, or aspect of the present invention may be explicitly excluded from any one or more of the claims. For example, any compound, compound combination, transcriptional modulator, cell type, cell state, or therapeutic indication may be excluded.

We claim:

1. A method of inhibiting proliferation or survival of a cell comprising contacting the cell with a positive transcription elongation factor b (P-TEFb) inhibitor and a c-Myc inhibitor.

2. The method of claim 1, wherein the P-TEFb inhibitor is a CDK9 inhibitor.

3. The method of claim 1, wherein the P-TEFb inhibitor is flavopiridol or a flavopiridol analog.

4. The method of claim 1, wherein the c-Myc inhibitor is a compound that inhibits interaction between c-Myc and Max.

5. The method of claim 1, wherein the cell is a human cell.

6. The method of claim 1, wherein the cell is a tumor cell.

7. The method of claim 1, wherein the cell is a stem cell.

8. A method of inhibiting pause release at a plurality of Myc target genes in a cell comprising contacting the cell with a positive transcription elongation factor b (P-TEFb) inhibitor and a c-Myc inhibitor.

9. The method of claim 8, wherein the cell is contacted with a P-TEFb inhibitor at a concentration that does not substantially inhibit pause release at non-c-Myc target genes when contacted with the cell in the absence of a c-Myc inhibitor.

10. A method of treating a subject suffering from a proliferative disease comprising administering therapeutically effective amounts of a positive transcription elongation factor b (P-TEFb) inhibitor and a c-Myc inhibitor to the subject.

11. The method of claim 10, wherein the proliferative disease is a tumor.

12. The method of claim 10, wherein the P-TEFb inhibitor is administered at a reduced dose relative to a standard dosing regimen.

13. The method of claim 10, wherein the subject is a human.

14. A composition comprising a positive transcription elongation factor b (P-TEFb) inhibitor and a c-Myc inhibitor.

15. A method for testing the ability of a compound combination to inhibit cell survival or proliferation, comprising (a) contacting one or more test cells with a positive transcription elongation factor b (P-TEFb) inhibitor and a c-Myc inhibitor; and (b) assessing survival or proliferation of the one or more test cells.

16. A method of modifying cell state or cell type comprising contacting the cell with a c-Myc inhibitor and a modulator of a second transcription modulator.

17. The method of claim 16, wherein cell state is proliferation state.

18. The method of claim 16, comprising inhibiting proliferation or survival of a cell.

19. The method of claim 16, comprising contacting the cell with a P-TEFb inhibitor and a c-Myc inhibitor, whereby cell proliferation or survival is inhibited.

20. A method of modulating pause release at a plurality of c-Myc target genes in a cell comprising contacting the cell with a c-Myc modulator and a modifier of a second transcriptional modulator.

21. A method of treating a subject suffering from a proliferative disease comprising administering therapeutically effective amounts of a positive transcription elongation factor b (P-TEFb) inhibitor and an NF-kB inhibitor to the subject.

22. A method of modulating pause release at a plurality of NF-kB target genes in a cell comprising contacting the cell with an NF-kB modulator and a modifier of a second transcriptional modulator.

23. The method of claim 8, wherein the P-TEFb inhibitor is a CDK9 inhibitor.

24. The method of claim 8, wherein the P-TEFb inhibitor is flavopiridol or a flavopiridol analog.

25. The method of claim 8, wherein the cell is a human cell.

26. The method of claim 8, wherein the cell is a tumor cell.

27. The method of claim 8, wherein the cell is a stem cell.

28. The method of claim 10, wherein the P-TEFb inhibitor is a CDK9 inhibitor.

29. The method of claim 10, wherein the P-TEFb inhibitor is flavopiridol or a flavopiridol analog.

30. The composition of claim 14, wherein the P-TEFb inhibitor is a CDK9 inhibitor.

31. The composition of claim 14, wherein the P-TEFb inhibitor is flavopiridol or a flavopiridol analog.

32. The method of claim 20, wherein the second transcriptional modulator is P-TEFb.

33. The method of claim 22, wherein the second transcriptional modulator is P-TEFb.

* * * * *